United States Patent
Maltz

(10) Patent No.: US 10,028,664 B2
(45) Date of Patent: *Jul. 24, 2018

(54) ASSESSING ENDOTHELIAL FUNCTION AND PROVIDING CALIBRATED UFMD DATA USING A BLOOD PRESSURE CUFF

(71) Applicant: The Regents of The University of California, Oakland, CA (US)

(72) Inventor: Jonathan S. Maltz, Oakland, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/680,082

(22) Filed: Aug. 17, 2017

(65) Prior Publication Data
US 2017/0367592 A1    Dec. 28, 2017

Related U.S. Application Data

(63) Continuation of application No. 15/236,250, filed on Aug. 12, 2016, now Pat. No. 9,737,217.
(Continued)

(51) Int. Cl.
*A61B 5/02* (2006.01)
*A61B 5/022* (2006.01)
(Continued)

(52) U.S. Cl.
CPC ........ *A61B 5/02021* (2013.01); *A61B 5/0225* (2013.01); *A61B 5/02116* (2013.01);
(Continued)

(58) Field of Classification Search
CPC ............ A61B 5/02021; A61B 5/02225; A61B 5/02233; A61B 5/0225; A61B 5/7225; A61B 5/7278; A61B 8/06; A61B 8/58
See application file for complete search history.

(56) References Cited

U.S. PATENT DOCUMENTS 3,994,284 A    11/1976   Voelker et al.
4,016,868 A    4/1977    Allison et al.
(Continued)

FOREIGN PATENT DOCUMENTS

CN    101288586 A    10/2008
CN    101843478 A    9/2010
(Continued)

OTHER PUBLICATIONS

U.S. Office Action dated Sep. 20, 2016 issued in U.S. Appl. No. 14/008,299.
(Continued)

*Primary Examiner* — Jacqueline Cheng
*Assistant Examiner* — Eric Messersmith
(74) *Attorney, Agent, or Firm* — Tom Hunter; Weaver Austin Villeneuve & Sampson LLP

(57) ABSTRACT

Methods and apparatus are provided for assessing endothelial function in a mammal. In certain embodiments the methods involve using a cuff to apply pressure to an artery in a subject to determine a plurality of baseline values for a parameter related to endothelial function as a function of applied pressure ($P_m$); b) applying a stimulus to the subject; and applying external pressure $P_m$ to the artery to determine a plurality of stimulus-effected values for the parameter related to endothelial function as a function of applied pressure ($P_m$); where the baseline values are determined from measurements made when said mammal is not substantially effected by said stimulus and differences in said baseline values and said stimulus-effected values provide a measure of endothelial function in said mammal.

30 Claims, 27 Drawing Sheets

Related U.S. Application Data

(60) Provisional application No. 62/205,470, filed on Aug. 14, 2015.

(51) Int. Cl.

| | | |
|---|---|---|
| *A61B 5/00* | (2006.01) | |
| *A61B 5/0225* | (2006.01) | |
| *A61B 8/06* | (2006.01) | |
| *A61B 8/00* | (2006.01) | |
| *A61B 5/021* | (2006.01) | |
| *A61B 17/135* | (2006.01) | |
| *A61B 5/107* | (2006.01) | |

(52) U.S. Cl.
CPC ...... *A61B 5/02208* (2013.01); *A61B 5/02225* (2013.01); *A61B 5/02233* (2013.01); *A61B 5/1075* (2013.01); *A61B 5/7225* (2013.01); *A61B 5/7278* (2013.01); *A61B 8/06* (2013.01); *A61B 8/58* (2013.01); *A61B 17/1355* (2013.01)

(56) References Cited

U.S. PATENT DOCUMENTS

| | | | |
|---|---|---|---|
| 4,141,346 | A | 2/1979 | Dean, Jr. et al. |
| 4,157,708 | A | 6/1979 | Imura |
| RE30,101 | E | 9/1979 | Kubicek et al. |
| 4,258,720 | A | 3/1981 | Flowers |
| 4,280,506 | A | 7/1981 | Zurcher |
| 4,305,401 | A | 12/1981 | Reissmueller et al. |
| 4,510,940 | A | 4/1985 | Wesseling |
| 4,539,997 | A | 9/1985 | Wesseling et al. |
| 4,548,211 | A | 10/1985 | Marks |
| 4,593,692 | A | 6/1986 | Flowers |
| 5,048,536 | A | 9/1991 | McEwen |
| 5,088,498 | A | 2/1992 | Beach et al. |
| 5,089,961 | A | 2/1992 | Coble et al. |
| 5,183,046 | A | 2/1993 | Beach et al. |
| 5,269,310 | A | 12/1993 | Jones et al. |
| 5,289,820 | A | 3/1994 | Beach et al. |
| 5,308,310 | A | 5/1994 | Roff et al. |
| 5,379,777 | A | 1/1995 | Lomask |
| 5,417,220 | A | 5/1995 | Apple |
| 5,513,648 | A | 5/1996 | Jackson |
| 5,579,776 | A | 12/1996 | Medero |
| 5,620,005 | A | 4/1997 | Ganshorn |
| 5,680,871 | A | 10/1997 | Ganshorn |
| 6,113,550 | A | 9/2000 | Wilson |
| 6,152,881 | A | 11/2000 | Raines et al. |
| 6,309,359 | B1 | 10/2001 | Whitt et al. |
| 6,338,719 | B1 | 1/2002 | Drzewiecki et al. |
| 6,463,311 | B1 | 10/2002 | Diab |
| 6,475,157 | B2 | 11/2002 | Wilson |
| 6,511,436 | B1 | 1/2003 | Asmar |
| 6,626,840 | B2 | 9/2003 | Drzewiecki et al. |
| 6,719,704 | B2 | 4/2004 | Narimatsu et al. |
| 6,816,741 | B2 | 11/2004 | Diab |
| 6,902,532 | B2 | 6/2005 | Lomask |
| 6,908,436 | B2 | 6/2005 | Chowienczyk et al. |
| 6,939,304 | B2 | 9/2005 | Schnall et al. |
| 7,044,918 | B2 | 5/2006 | Diab |
| 7,300,404 | B1 | 11/2007 | Kolluri et al. |
| 7,390,302 | B2 | 6/2008 | Friedman et al. |
| 7,390,303 | B2 | 6/2008 | Dafni et al. |
| 7,402,137 | B2 | 7/2008 | Lomask et al. |
| 7,407,486 | B2 | 8/2008 | Huiku et al. |
| 7,462,152 | B2 | 12/2008 | Kolluri et al. |
| 8,827,911 | B2 | 9/2014 | Tsuji et al. |
| 9,161,695 | B2 | 10/2015 | Tsuji et al. |
| 9,445,727 | B2 | 9/2016 | Tsuji et al. |
| 9,737,217 | B2 | 8/2017 | Maltz |
| 2002/0107461 | A1 | 8/2002 | Hui et al. |
| 2002/0111554 | A1 | 8/2002 | Drzewiecki et al. |
| 2002/0133082 | A1 | 9/2002 | Ogura |
| 2002/0138016 | A1 | 9/2002 | Wilson |
| 2003/0032873 | A1 | 2/2003 | Diab |
| 2003/0065270 | A1 | 4/2003 | Raines et al. |
| 2004/0158162 | A1 | 8/2004 | Narimatsu et al. |
| 2004/0254489 | A1 | 12/2004 | Lomask |
| 2005/0070805 | A1 | 3/2005 | Dafni |
| 2005/0085702 | A1 | 4/2005 | Diab |
| 2005/0143665 | A1 | 6/2005 | Huiku et al. |
| 2005/0228303 | A1 | 10/2005 | Hayano et al. |
| 2005/0251053 | A1 | 11/2005 | Lomask et al. |
| 2006/0206021 | A1 | 9/2006 | Diab |
| 2006/0258946 | A1 | 11/2006 | Hayano et al. |
| 2006/0264755 | A1 | 11/2006 | Maltz et al. |
| 2007/0113857 | A1 | 5/2007 | Weiss et al. |
| 2007/0179394 | A1 | 8/2007 | Sheehan et al. |
| 2007/0225606 | A1 | 9/2007 | Naghavi et al. |
| 2007/0225614 | A1 | 9/2007 | Naghavi et al. |
| 2007/0287923 | A1 | 12/2007 | Adkins et al. |
| 2008/0027330 | A1 | 1/2008 | Naghavi et al. |
| 2008/0045846 | A1 | 2/2008 | Friedman et al. |
| 2008/0081963 | A1 | 4/2008 | Naghavi et al. |
| 2008/0082006 | A1 | 4/2008 | Kolluri et al. |
| 2008/0119741 | A1 | 5/2008 | Friedman et al. |
| 2008/0188760 | A1 | 8/2008 | Al-Ali et al. |
| 2008/0255471 | A1 | 10/2008 | Naghavi et al. |
| 2008/0262362 | A1 | 10/2008 | Kolluri et al. |
| 2009/0012395 | A1 | 1/2009 | Reynolds et al. |
| 2009/0259131 | A1 | 10/2009 | Tsuji et al. |
| 2010/0081941 | A1 | 4/2010 | Naghavi et al. |
| 2010/0292592 | A1 | 11/2010 | Parfenov et al. |
| 2010/0305459 | A1 | 12/2010 | Whitt et al. |
| 2011/0066048 | A1 | 3/2011 | Tsuji et al. |
| 2011/0077486 | A1 | 3/2011 | Watson et al. |
| 2013/0158418 | A1 | 6/2013 | Mizukami |
| 2014/0114117 | A1 | 4/2014 | Naghavi et al. |
| 2014/0128747 | A1 | 5/2014 | Maltz |
| 2014/0276144 | A1 | 9/2014 | Whitt et al. |
| 2015/0359437 | A1 | 12/2015 | Maltz |
| 2017/0042431 | A1 | 2/2017 | Maltz |

FOREIGN PATENT DOCUMENTS

| | | |
|---|---|---|
| WO | WO 2012/149209 A1 | 11/2012 |
| WO | WO 2017/031005 A1 | 2/2017 |

OTHER PUBLICATIONS

U.S. Final Office Action dated Jul. 11, 2017 issued in U.S. Appl. No. 14/008,299.
U.S. Office Action dated Dec. 1, 2016 issued in U.S. Appl. No. 15/236,250.
U.S. Notice of Allowance dated Apr. 3, 2017 issued in U.S. Appl. No. 15/236,250.
PCT International Search Report and Written Opinion dated Jul. 26, 2012 issued in PCT/US2012/035285.
PCT International Preliminary Report on Patentability dated Oct. 29, 2013 issued in PCT/US2012/035285.
PCT International Search Report and Written Opinion dated Nov. 16, 2016 issued in PCT/US2016/046910.
CN 1st Office Action dated Mar. 3, 2015 issued in CN201280020509.1.
CN 2nd Office Action dated Jan. 5, 2016 issued in CN201280020509.1.
CN 3rd Office Action dated Sep. 5, 2016 issued in CN201280020509.1.
Axtell, et al. (2010) "Assessing Endothelial Vasodilator Function with the Endo-PAT 2000" *J. Visualized Exp.*, DOI: 10-.3791/2167, pp. 1-5.
Brunner, et al. (Feb. 2005) "Endothelial function and dysfunction. Part II: Association with cardiovascular risk factors and diseases. A statement by the Working Group on Endothelins and Endothelial Factors of the European Society of Hypertension.," *J Hypertens*, 23(2): 233-246.
Celermajer et al. (1992) "Non-invasive detection of endothelial dysfunction in children and adults at risk of atherosclerosis." *The Lancet*, 340: 1111-1115.

(56) References Cited

OTHER PUBLICATIONS

Deanfield, et al. (Jan 2005) "Endothelial function and dysfunction. Part I: Methodological issues for assessment in the different vascular beds: a statement by the Working Group on Endothelin and Endothelial Factors of the European Society of Hypertension.," *J Hypertens*, 23: 7-17.

Hamburg et al. (2008) "Cross-sectional relations of digital vascular function to cardiovascular risk factors in The Framingham Heart Study" *Circulation*, 117(19): 2467-2474.

Huang, et al. (2007) "Assessment of Endothelial Function in the Radial Artery Using Inhaled Albuterol." *Conf Proc IEEE Eng Med Bioi Soc. 2007*, 3629-3631.

Iida, et al. (Aug. 1, 2006) "Noninvasive low-frequency ultrasound energy causes vasodilation in humans." *J Am Coli Cardiol.* 48(3):532-7. Epub Jul. 12, 2006.

Lerman, et al. (2005) "Endothelial Function—Cardiac Events" *Circulation*, 111(3): 363-368.

Mangoni, et al. (1995) "Radial Artery Compliance in Young, Obese, Normotensive Subjects," *Hypertension* 26:984-988.

Naghavi, (2016) "Endothelial Functional Testing; A Missed Opportunity in Most Physicians' Offices: A review of State-of-the-Art in ASCVD Risk Assessment—Risk Factors vs. Structural vs. Functional Tests," *Presentation for Endothelix Company*, 125 pages.

Nohria, et al. (2006) "Role of nitric oxide in the regulation of digital pulse volume amplitude in humans," *J Appl Physiol*, 101(2): 545-548.

Takase et al. (1998) "Endothelium-dependent flow-mediated vasodilation in coronary and brachial arteries in suspected coronary artery disease" *Am J Cardiol*, 82(12): 1535-1539.

U.S. Office Action dated Oct. 5, 2017 issued in U.S. Appl. No. 14/678,642.

Ukawa et al. (Dec. 2012) "Novel non-invasive method of measurement of endothelial function: enclosed-zone flow-mediated dilatation (ezFMD)" *Medical & Biological Engineering & Computing*, 50(12): 1239-1247.

ASSESSING ENDOTHELIAL FUNCTION AND PROVIDING CALIBRATED UFMD DATA USING A BLOOD PRESSURE CUFF

CROSS-REFERENCE TO RELATED APPLICATIONS

This application is a Continuation of U.S. Ser. No. 15/236,250, filed on Aug. 12, 2016, now U.S. Pat. No: 9,737,217, which claims priority to and benefit of U.S. Ser. No. 62/205,470, filed on Aug. 14, 2015, both of which are incorporated herein by reference in their entirety for all purposes.

STATEMENT OF GOVERNMENTAL SUPPORT

This invention was made with government support under Contract No. DE-AC02-05CH11231, awarded by the U.S. Department of Energy. The government has certain rights in the invention.

BACKGROUND

Impairment of arterial endothelial function is an early event in atherosclerosis and correlates with all of the major risk factors for cardiovascular disease (CVD). The most widely employed noninvasive measure of endothelial function involves brachial artery (BA) diameter measurement using ultrasound imaging before and after several minutes of blood flow occlusion (Celermajer et al. (1992) *The Lancet*, 340: 1111-1115). The change in arterial diameter is a measure of flow-mediated vasodilation (FMD). This peripheral measurement correlates strongly with coronary artery endothelial function, a fact that strongly supports its clinical value. However, the high between-laboratory variability of results and cost of instrumentation render this technique unsuitable for routine clinical use.

Endothelial function is both acutely and chronically affected by lifestyle factors that influence CVD risk (Brunner et al. (2005) *J. Hypertens.*, 23: 233-246). Consequently, measures of endothelial function are useful in monitoring response to medication, dietary changes and exercise regimens. Unfortunately, very little work has focused on determining the clinical value of endothelial function measurements for individual patients or on developing measurement methods suitable for routine or continuous monitoring of endothelial function. There are compelling reasons to believe that knowledge of acute variation in endothelial function in an individual is important. Since NO released by the endothelium is a potent inhibitor of leukocyte and monocyte adhesion to the endothelial cell surface, and since adhesion of these cells is widely believed to be a necessary initiating event in atherogenesis (Deanfield et al. (2005) *J. Hypertens.*, 23: 7-17), it is reasonable to infer that the proportion of time that the endothelium is dysfunctional constitutes an important indicator of disease risk. This is the rationale for the development of techniques that are simple and cheap enough to enable regular or continuous measurement of endothelial function.

The two FDA-approved commercially available systems for measuring endothelial function perform measurements that are based on the flow and pulse pressure in resistance vessels (rather than in conduit arteries). The Endo-PAT2000 system from Itamar Medical analyzes the pulse amplitude in the finger before and after application on endothelial stimulus. While about 46% of the observed changes in pulse amplitude are blocked by NO synthase inhibitors, mechanisms other than those mediated by NO significantly contribute towards the response (Nohria et al. (2006) *J Appl Physiol*, 101(2): 545-548). This is most probably a consequence of the different mechanisms involved in arterial and arteriolar/microvascular vasodilation. Also, the measurement is made in vessels that experience ischemia and the many non-NO-mediated vasodilatory processes that occur under ischemic conditions. It is clinically preferable to perform measurements on arteries such as the brachial artery, the endothelial response of which is highly correlated with that of the coronary arteries (r=0.78, p<0.001, Takase et al. (1998) *Am. J Cardiol.*, 82(12): 1535-1539). In addition, a review of close to 2,500 studies found that brachial and coronary artery EF have similar power to predict serious cardiovascular events over a follow-up period of 1-92 months (Lerman and Zeiher (2005) *Circulation*, 111(3): 363-368). The authors of the review assert that "the similar power of coronary and peripheral endothelial dysfunction to predict cardiovascular events and the observation that the cardiovascular events may occur remotely from the site in which the endothelial dysfunction was detected underscore the systemic nature of endothelial dysfunction and its pivotal role in prediction of cardiovascular events." It is not currently possible to make such strong statements regarding the significance of microvascular endothelial function.

Two large (>1800 subject) cross-sectional studies found an association between EndoPAT measurements and accepted cardiovascular risk factors (Palmisano et al. (2011) *Hypertension*, 57(3): 390-396; Schnabel et al. (2011) *Circulation: Cardiovascular Imaging*, 4(4): 371-380). However, the correlations between EndoPAT and FMD were low in the respective studies: r=0.094 (N=1843), and r=0.19 (N=5000). Correlations decreased further when adjusted for age and sex. Also, some of the results suggest the influence of potentially serious confounding factors. For example, while it is well known that endothelial function tends to decrease with age, older subjects exhibited better endothelial response according to Endo-PAT (Hamburg et al. (2008) *Circulation*, 117(19): 2467-2474).

A second approved device is the Vendys system developed by Endothelix, Inc. of Houston Tex. This system measures the cutaneous reactive hyperemic response using hand skin temperature measurement during two minutes of brachial artery occlusion and ensuing RH. During occlusion, skin temperature drops in the distal hand. As blood flow is restored, the temperature increases. Studies indicate that the recovery of skin temperature is slowed in subjects having higher Framingham risk scores and other metrics of CVD and CVD risk. Interestingly, substantial temperature changes are also observed in the contralateral hand that experiences no reactive hyperemic episode. This suggests significant neural involvement in the response. For this reason and the results of Wong et al. (2003)*J. Appl. Physiol.*, 95: 504-510 it is reasonable to predict that this response cannot be blocked by NOS inhibitors.

There is no doubt that these systems provide clinical value and can identify patients with pooled cardiovascular risk factors. However, it is not clear that these systems can do this better than paper-based scoring methods such as the Framingham risk in general populations. It is also highly probable that sympathetic nervous activation is a significant confounding factor in endothelial function measurements based on arteriolar and microvascular responses.

Much stronger evidence exists that peripheral artery endothelial function provides more than simply a correlate of CVD risk factors. Few clinicians would disagree with the statement that evaluation of EF in conduit arteries has more proven clinical value.

SUMMARY

Conventional flow mediated dilation (FMD) studies measure arterial diameter before and after the application of an endothelial stimulus. In the methods and apparatus described herein the cross sectional area of the artery rather than the diameter is measured. Rather than employing B-mode ultrasound to image the arterial lumen, a simple inexpensive blood pressure cuff is utilized.

Throughout this document, the term "area" measurement is not necessarily taken to mean an actual calibrated measurement of area, but rather a quantity proportional to, or representative of, arterial luminal area. In most embodiments, this area measure is obtained from the amplitude of the pulse waveform, sensed as pressure changes in a cuff. The reason a calibrated measure of area is not required for the methods taught here, is that key calculations involve the ratio of "areas" measured before and after application of a stimulus, and these ratios are independent of absolute calibration factors. Measures such as the ratio of post- to pre-stimulus pressure waveform amplitudes constitute "measured areas" for this purpose.

Various embodiments contemplated herein may include, but need not be limited to, one or more of the following:

Embodiment 1: A method of assessing endothelial function in a mammal, said method comprising: a) applying external pressure $P_m$ to an artery for a period of time $T_m$, and determining, over the course of one or more cardiac cycles in said period $T_m$, changes in pressure in a cuff resulting from cardiac activity of said mammal, or an artificially induced arterial pulse, to determine values for a baseline parameter related to endothelial function in said mammal, where said baseline parameter is determined for at least three different external pressure points ($P_m$) by varying the external pressure $P_m$ during period of time $T_m$, and/or by determining said baseline parameter over a plurality of time periods $T_m$ having different external pressure points ($P_m$), to provide a plurality of baseline values for said parameter related to endothelial function as a function of applied pressure ($P_m$); b) applying a stimulus to said mammal; and c) applying external pressure $P_m$ to an said artery for a period of time T, and determining over the course of one or more cardiac cycles in said period $T_m$, changes in pressure in said cuff resulting from cardiac activity of said mammal, or an artificially induced arterial pulse, to determine values for a stimulus-effected parameter related to endothelial function in said mammal, where said stimulus-effected parameter is determined for at least three different external pressure points ($P_m$) by varying the external pressure $P_m$ during period of time $T_m$, and/or by determining said parameter over a plurality of time periods $T_m$ having different external pressure points ($P_m$), to provide a plurality of stimulus-effected values for said parameter related to endothelial function as a function of applied pressure ($P_m$); wherein said baseline values are determined from measurements made when said mammal is not substantially effected by said stimulus and differences in said baseline values and said stimulus-effected values provide a measure of endothelial function in said mammal.

Embodiment 2: The method of embodiment 1, wherein said method further comprises: determining the area (e.g., a measure proportional to the area) of the arterial lumen calculated from the baseline pressure measurements as a function of transmural pressure $P_{tm}$, where transmural pressure is determined as the difference between the baseline measured pressures and the external cuff pressure $P_m$ and fitting these data with a first non-linear model to provide a first function describing baseline arterial lumen area as function of transmural pressure; determining the area (e.g., a measure proportional to the area) of the arterial lumen calculated from the stimulus-effected pressure measurements as a function of transmural pressure $P_{tm}$, where transmural pressure is determined as the difference between the measured stimulus-effected pressures and the external cuff pressure $P_m$ and fitting these data with a second non-linear model to provide a second function describing stimulus-effected arterial lumen area as function of transmural pressure; using said first function to calculate baseline arterial lumen area ($A_b$) (e.g., a measure proportional to the area $A_b$) at a transmural pressure substantially equal to the systolic blood pressure; using said second function to calculate stimulus-effected arterial lumen area ($A_r$) (e.g., a measure proportional to the area $A_r$) at a transmural pressure substantially equal to the systolic blood pressure; and determining the equivalent ultrasound-based FMD (uFMD) measure where uFMD is proportional to the square root of the ratio $A_r/A_b$.

Embodiment 3: The method of embodiment 2, comprising outputting said measure to a display, printer, or computer readable medium.

Embodiment 4: The method according to any one of embodiments 2-3, wherein the equivalent ultrasound-based FMD is given as $$uFMD\% = [\sqrt{(A_r/A_b)} - 1] \times 100$$

Embodiment 5: The method according to any one of embodiments 2-4, wherein said first non-linear model and/or said second non-linear model are the same type of function.

Embodiment 6: The method according to any one of embodiments 2-5, wherein said first non-linear model and/or said second non-linear model are selected from the group consisting of a 2 parameter model, a 3 parameter model, a four parameter model, a 5 parameter model, and a six parameter model.

Embodiment 7: The method according to any one of embodiments 2-5, wherein said first non-linear model and said second non-linear model are three parameter models.

Embodiment 8: The method of embodiment 7, wherein said first non-linear model and said second non-linear model are arctangent models.

Embodiment 9: The method according to any one of embodiments 1-8, wherein baseline values and stimulus effected values are determined for the same limb or region.

Embodiment 10: The method according to any one of embodiments 1-8, wherein baseline values are determined for a limb or region contralateral to a limb or region used for determining the stimulus effected values.

Embodiment 11: The method of embodiment 10, wherein said contralateral limb or region is used for monitoring blood pressure during measurement.

Embodiment 12: The method of embodiment 11, wherein the monitored blood pressure is used to adjust the measurement pressure if blood pressure changes during the measurement.

Embodiment 13: The method according to any one of embodiments 1-12, wherein said applying external pressure $P_m$ to an said artery for a period of time $T_m$ comprises applying a substantially constant external pressure $P_m$ for a period of time $T_m$.

Embodiment 14: The method according to any one of embodiments 1-12, wherein said applying external pressure $P_m$ to an said artery for a period of time $T_m$, comprises applying a continuously varying external pressure $P_m$ for a period of time $T_m$.

Embodiment 15: The method according to any one of embodiments 1-14, wherein step (a) and/or step (b) comprises determining said values for a baseline parameter and/or said values for a stimulus-effected parameter for at least 3 different pressures ($P_m$), or for at least 4 different pressures ($P_m$), or for at least 5 different pressures ($P_m$), or for at least 6 different pressures ($P_m$), or for at least 7 different pressures ($P_m$), or for at least 8 different pressures ($P_m$), or for at least 9 different pressures ($P_m$), or for at least 10 different pressures ($P_m$), or during a continuous pressure variation.

Embodiment 16: The method according to any one of embodiments 1-15, wherein said external pressure is less than the mean arterial pressure.

Embodiment 17: The method according to any one of embodiments 1-15, wherein said external pressure is less than the mean diastolic pressure.

Embodiment 18: The method according to any one of embodiments 1-17, wherein said external pressure ($P_m$) ranges from about 20 mmHg up to about 80 mmHg.

Embodiment 19: The method according to any one of embodiments 1-18, wherein the external pressure points ($P_m$) used to determine said baseline values are substantially the same as the external pressure points (PM) used to determine the stimulus-effected values.

Embodiment 20: The method according to any one of embodiments 1-18, wherein the external pressure points ($P_m$) used to determine said baseline values are different than the external pressure points (PM) used to determine the stimulus-effected values.

Embodiment 21: The method according to any one of embodiments 1-20, wherein said baseline parameter is determined for at least three different external pressure points ($P_m$) by varying the external pressure $P_m$ during period of time $T_m$.

Embodiment 22: The method according to any one of embodiments 1-21, wherein said baseline parameter is determined for at least three different external pressure points ($P_m$) by determining said baseline parameter over a plurality of time periods $T_m$ having different external pressure points ($P_m$).

Embodiment 23: The method according to any one of embodiments 1-22, wherein said stimulus-effected parameter is determined for at least three different external pressure points ($P_m$) by varying the external pressure $P_m$ during period of time $T_m$.

Embodiment 24: The method according to any one of embodiments 1-23, wherein said stimulus-effected parameter is determined for at least three different external pressure points ($P_m$) by determining said parameter over a plurality of time periods $T_m$ having different external pressure points ($P_m$).

Embodiment 25: The method according to any one of embodiments 1-24, wherein the step (a) is repeated at least twice, or at least 3 times, or at least 5 times, or at least about 10 times.

Embodiment 26: The method according to any one of embodiments 1-25, wherein the step (c) is repeated at least twice, or at least 3 times, or at least 5 times, or at least about 10 times.

Embodiment 27: The method according to any one of embodiments 1-26, wherein the duration of said time interval(s) ($T_m$) used to determine said baseline values and/or said stimulus-effected values ranges from about 1 sec, or from about 2 sec, or from about 3 sec, or from about 4 sec, or from about 5 sec, or from about 6 sec, or from about 7 sec, or from about 8 sec, or from about 9 sec, or from about 10 sec, or from about 15 sec up to about 20 sec, or up to about 30 sec or up to about 40 sec or up to about 50 sec, or up to about 1 min, or up to about 2 min, or up to about 3 min, or up to about 4 min, or up to about 5 min, or up to about 6 min, or up to about 7 min, or up to about 8 min, or up to about 9 min, or up to about 10 min, or up to about 15 min, or up to about 20 min, or up to about 25 min, or up to about 30 min.

Embodiment 28: The method according to any one of embodiments 1-26, wherein the duration of said time interval(s) ($T_m$) used to determine said baseline values and/or said stimulus-effected values is about 30 seconds.

Embodiment 29: The method according to any one of embodiments 1-28, wherein there are a plurality of measurement periods ($T_m$) with a waiting period of at least 30 seconds between cuff inflations.

Embodiment 30: The method according to any one of embodiments 1-29, wherein during said time interval(s) said external pressure is maintained substantially constant and held at different levels in different time intervals.

Embodiment 31: The method according to any one of embodiments 1-29, wherein said pressure is adjusted to different levels during a single time period ($T_m$).

Embodiment 32: The method according to any one of embodiments 1-31, wherein said establishing baseline values and/or determining stimulus-effected values comprises determining values for changes in pressure resulting from an artificially induced arterial pulse.

Embodiment 33: The method according to any one of embodiments 1-31, wherein said establishing baseline values and/or determining stimulus-effected values comprises determining values for changes in pressure resulting from cardiac activity of said mammal.

Embodiment 34: The method according to any one of embodiments 1-33, wherein said cuff is disposed around an arm or leg of said mammal.

Embodiment 35: The method according to any one of embodiments 1-34, wherein said cuff is pressurized by a gas or gas mixture.

Embodiment 36: The method according to any one of embodiments 1-34, wherein said cuff is pressurized by a liquid or gel.

Embodiment 37: The method according to any one of embodiments 1-36, wherein said mammal is a human.

Embodiment 38: The method according to any one of embodiments 1-36, wherein said mammal is a non-human mammal.

Embodiment 39: The method according to any one of embodiments 1-38, wherein said external pressure is maintained by a system that monitors and adjusts the pressure in said cuff and whose response time is sufficiently slow so that the changes in pressure resulting from said cardiac activity are not substantially attenuated by said system.

Embodiment 40: The method of embodiment 39, wherein said response time is sufficiently slow so that said pressure changes resulting from said cardiac activity are attenuated by less than 10%.

Embodiment 41: The method according to any one of embodiments 1-40, wherein said external pressure is maintained by setting the pressure in said cuff to a value and not altering external pressure applied to said cuff during the measurements of pressure variations due to said cardiac activity.

Embodiment 42: The method according to any one of embodiments 1-41, wherein applying the pressure to the artery comprises applying a local pressure that does not substantially affect other blood vessels in a same limb as the artery.

Embodiment 43: The method according to any one of embodiments 1-41, wherein applying the external pressure to the artery comprises applying a pressure that affects an entire cross-section of a limb including the artery.

Embodiment 44: The method according to any one of embodiments 1-43, wherein said external pressure is equivalent to or below the average diastolic pressure measured for said subject.

Embodiment 45: The method of embodiment 44, wherein said substantially external pressure is below the average diastolic pressure measured for said subject or below an expected diastolic pressure for said subject.

Embodiment 46: The method according to any one of embodiments 1-45, wherein said substantially constant external pressure is set to predetermined pressures.

Embodiment 47: The method according to any one of embodiments 1-46, wherein the baseline values are determined before applying the stimulus.

Embodiment 48: The method according to any one of embodiments 1-47, wherein the determining stimulus-effected values is performed at least about 30 seconds after stimulus, or at least about 45 seconds after said stimulus, or at least about 6o seconds after said stimulus, or at least about 90 seconds after said stimulus.

Embodiment 49: The method according to any one of embodiments 1-48, wherein the determining stimulus-effected values is performed up to about 5 minutes after said stimulus, or up to about 4 minutes, or up to about 3 minutes, or up to about 2 minutes or up to about 90 seconds after said stimulus.

Embodiment 50: The method according to any one of embodiments 1-46, wherein the baseline values are determined after applying the stimulus.

Embodiment 51: The method according to any one of embodiments 1-50, wherein said determining, over the course of one or more cardiac cycles, changes in pressure in said cuff resulting from cardiac activity of said mammal comprises determining the pressure in said cuff as a function of time.

Embodiment 52: The method of embodiment 51, wherein said determining comprises integrating the value of a pressure change over time (calculating the area under a pressure/time curve) for one or for a plurality of cardiac cycles to determine an integrated pressure value.

Embodiment 53: The method according to any one of embodiments 51-52, wherein said determining comprises determining the maximum, or a certain percentile rank of the derivative of the pressure versus time wave form on the rising edge of a pressure pulse for one or for a plurality of cardiac cycles to determine a compliance value.

Embodiment 54: The method according to any one of embodiments 52-53, wherein said integrated pressure value and/or said compliance value is averaged over a plurality of cardiac cycles.

Embodiment 55: The method according to any one of embodiments 52-53, wherein said integrated pressure value and/or said compliance value is determined for a single cardiac cycle.

Embodiment 56: The method of embodiment 55, wherein said single cardiac cycle is a cardiac cycle selected for the maximum change in said value in a plurality of cardiac cycles.

Embodiment 57: The method of embodiment 55, wherein said single cardiac cycle is a cardiac cycle selected for the maximum change in said value between a baseline measurement and a stimulus-effected measurement.

Embodiment 58: The method of embodiment 51, wherein said determining, over the course of one or more cardiac cycles, changes in pressure in said cuff resulting from cardiac activity of said mammal comprises determining the pressure in said cuff as a function of time to provide a cardiac pulse waveform.

Embodiment 59: The method of embodiment 58, wherein said determining, over the course of one or more cardiac cycles, changes in pressure in said cuff resulting from cardiac activity of said mammal comprises determining the pressure in said cuff as a function of time to provide a cardiac pulse waveform while the cuff inflates and/or while said cuff deflates.

Embodiment 60: The method of embodiment 59, wherein said determining is while said cuff inflates and/or deflates as a rate of about 3 to 6 mmHg/s.

Embodiment 61: The method according to any one of embodiments 59-60, wherein the cardiac pulse waveforms are compared between baseline and post-stimulus conditions by direct comparison of pulse characteristics at corresponding pressure levels.

Embodiment 62: The method according to any one of embodiments 59-60, wherein the cardiac pulse waveforms are compared between baseline and post-stimulus conditions by first fitting models to the set of baseline cardiac pulse waver forms and to the set of post-stimulus cardiac pulse waveforms and comparing parameters generated by the two models.

Embodiment 63: The method according to any one of embodiments 59-62, wherein blood pressure and cFMD are measured simultaneously.

Embodiment 64: The method according to any one of embodiments 59-63, wherein said cuff is inflated to a pressure in excess of the peak of the cardiac pulse waveform (oscillometric waveform).

Embodiment 65: The method according to any one of embodiments 59-64, wherein the systolic BP and MAP are measured and the diastolic blood pressure (DBP) is calculated using an oscillometric analysis.

Embodiment 66: The method according to any one of embodiments 59-65, wherein the systolic BP and MAP are measured and the DBP is determined by analyzing Korotkoff sounds obtained using an audio sensor (e.g., stethoscope, phonocadiogram) or ultrasound probe.

Embodiment 67: The method according to any one of embodiments 59-66, wherein measurements to calculate cFMD and/or MAP, and/or DBP are obtained during cuff inflation.

Embodiment 68: The method according to any one of embodiments 59-67, wherein measurements to calculate cFMD and/or MAP, and/or DBP are obtained during cuff deflation.

Embodiment 69: The method according to any one of embodiments 59-68, wherein systolic BP and/or diastolic BP is determined and for cFMD determination, comparison of pulse waveform characteristics between baseline and post-stimulus intervals at corresponding pressures is a comparison made where the corresponding pressures are transmural pressures calculated using the determined systolic and/or diastolic BP values.

Embodiment 70: The method of embodiment 62, wherein comparison of pulse waveform characteristics between baseline and post-stimulus intervals at corresponding pressures is a comparison made based on the transmural pressure determined by the models.

Embodiment 71: The method according to any one of embodiments 59-70, wherein: measurements are made of the same mammal at a plurality of different times; and measurement(s) made at earlier times in said plurality are used to determine the tone sate of the vessel at the current measurement time.

Embodiment 72: The method of embodiment 71, wherein the degree of dilation (tone state) at baseline is used to adjust the cFMD and BP measurement s to the current vessel tone state.

Embodiment 73: The method according to any one of embodiments 71-72, wherein the maximal dilated state is measured by stimulating the vessel with an NO donor such as nitroglycerin.

Embodiment 74: The method according to any one of embodiments 71-73, wherein a constricted state is measured by stimulating the vessel with a vasoconstrictive sub stance.

Embodiment 75: The method according to any one of embodiments 71-72, wherein which the dilatory and constrictory potential of the vessel and tone state are inferred by measurements obtained with the cuff elevated at different vertical levels with respect to the heart.

Embodiment 76: The method according to any one of embodiments 71-75, wherein a model describing the dependence of the oscillometric characteristic on vessel tone is used to define thresholds for oscillometric determination of DBP.

Embodiment 77: The method according to any one of embodiments 1-76, wherein during said time intervals pressure is applied to said cuff using a control feedback system to adjust a pump or other pressure source and/or a proportional release valve to alter the applied pressure.

Embodiment 78: The method according to any one of embodiments 1-76, wherein during said time intervals said pressure is periodically adjusted using an on-off control system.

Embodiment 79: The method according to any one of embodiments 1-76, wherein during said time intervals adjustment of said pressure is by a pump and a proportional valve that operate simultaneously to maintain pressure where pump remains on while the valve is adjusted to maintain a constant pressure, this system being characterized by a time constant such that a cardiac pulse signal is not appreciably attenuated by the servo mechanism.

Embodiment 80: The method according to any one of embodiments 1-79, wherein applying the stimulus comprises restricting flow of blood to the limb by occlusion of a blood vessel.

Embodiment 81: The method of embodiment 80, wherein restricting the flow of blood is accomplished using a cuff and/or a tourniquet.

Embodiment 82: The method of embodiment 80, wherein restricting the flow of blood and applying the pressure on the artery are performed using separate cuffs.

Embodiment 83: The method of embodiment 80, wherein the same cuff is used to occlude the blood vessel and to apply the pressure on the artery.

Embodiment 84: The method according to any one of embodiments 82-83, wherein restricting flow of blood through the artery comprises inflating the restricting cuff to a pressure at least 10 mm Hg above measured systolic blood pressure for said mammal.

Embodiment 85: The method according to any one of embodiments 80-84, wherein restricting flow of blood through the artery comprises restricting for at least 1 minute.

Embodiment 86: The method according to any one of embodiments 1-57, wherein applying the stimulus comprises administering a drug to said mammal.

Embodiment 87: The method of embodiment 86, wherein said drug is not an NO agonist.

Embodiment 88: The method according to any one of embodiments 86-87, wherein said drug is a β-adrenergic agonist.

Embodiment 89: The method of embodiment 86, wherein said drug is an NO donor.

Embodiment 90: The method of embodiment 89, wherein said drug comprises nitroglycerin or sodium nitroprusside.

Embodiment 91: The method according to any one of embodiments 1-57, wherein said stimulus does not comprise occlusion of an artery and/or does not comprise administration of a drug.

Embodiment 92: The method of embodiment 91, wherein said stimulus comprises low intensity ultrasound.

Embodiment 93: The method of embodiment 91, wherein said stimulus comprises acoustic/mechanical tissue vibration.

Embodiment 94: The method according to any one of embodiments 1-91, wherein said measure of endothelial function, in the context of differential diagnosis, is an indicator of a cardiovascular pathology.

Embodiment 95: The method of embodiment 94, wherein said cardiovascular pathology is a condition selected from the group consisting of Atherosclerosis, hypercholesterolemia, high LDL-C, low HDL-C, high lipoprotein (a), small dense LDL-C, oxidized LDL-C, hypertension, high homocysteine, aging, vasculitis, preeclampsia, metabolic syndrome, variant angina, diabetes, active smoking, passive smoking, ischemia-reperfusion, transplant atherosclerosis, cardiopulmonary bypass, postmenopausal, Kawasaki's disease, Chagas' disease, family history CAD, infections, depression, inactivity, obesity, renal failure, increased CRP, congestive heart failure, and left ventricular hypertrophy.

Embodiment 96: The method according to any one of embodiments 1-95, wherein said measure of endothelial function in said mammal is printed out and/or stored on a tangible medium.

Embodiment 97: The method of embodiment 96, wherein said tangible medium comprises a medical record.

Embodiment 98: The method of embodiment 96, wherein said medical record is a computerized medical record.

Embodiment 99: An apparatus for assessment endothelial function in a mammal comprising: a measurement cuff adapted to apply a substantially pressure to an artery in said mammal; a measurement unit adapted to detect and quantify over one or more cardiac cycles, pressure pulses in said cuff while said pressure is applied; a controller that is adapted to apply to the cuff different pressures within a single time period (Tm), and/or to apply substantially constant pressures that differ in different time periods ($T_m$) where said controller monitors and adjusts the pressure in said cuff and whose response time is sufficient slow so that the changes in pressure resulting from said cardiac cycles are not substantially attenuated by said system, and/or that is adapted to control a pressure source and a valve to provide on-off control of the pressure in said cuff; and a processor adapted to determine a plurality of baseline values for a parameter related to endothelial function as a function of applied pressure ($P_m$) and to determine a plurality of stimulus-effected values for a parameter related to endothelial function as a function of applied pressure ($P_m$).

Embodiment 100: The apparatus of embodiment 99, wherein said processor is adapted to: determine the area (e.g., a measure proportional to the area) of the arterial lumen calculated from the baseline pressure measurements as a function of transmural pressure $P_{tm}$, where transmural pressure is determined as the difference between the baseline measured pressures and the external cuff pressure $P_m$ and fitting these data with a first non-linear model to provide a first function describing baseline arterial lumen area as function of transmural pressure; to determine the area (e.g., a measure proportional to the area) of the arterial lumen calculated from the stimulus-effected pressure measurements as a function of transmural pressure $P_{tm}$, where transmural pressure is determined as the difference between the measured stimulus-effected pressures and the external cuff pressure $P_m$ and fitting these data with a second non-linear model to provide a second function describing stimulus-effected arterial lumen area as function of transmural pressure; to use said first function to calculate baseline arterial lumen area ($A_b$) (e.g., a measure proportional to the area $A_b$) at a transmural pressure substantially equal to the systolic blood pressure; and to use said second function to calculate stimulus-effected arterial lumen area ($A_r$) (e.g., a measure proportional to the area $A_r$) at a transmural pressure substantially equal to the systolic blood pressure.

Embodiment 101: The apparatus of embodiment 100, wherein said processor is configured to determine the equivalent ultrasound-based FMD (uFMD) where uFMD is proportional to the square root of the ratio $A_r/A_b$.

Embodiment 102: The apparatus of embodiment 101, wherein said processor is configured to determine the equivalent ultrasound-based FMD is given as $$uFMD\% = [\sqrt{(A_r/A_b)} - 1] \times 100$$

Embodiment 103: The apparatus according to any one of embodiments 99-102, wherein said apparatus is configured to perform the method according to any one of embodiments 1-79, except application of said stimulus.

Embodiment 104: The apparatus according to any one of embodiments 99-102, wherein said apparatus is configured to perform the method according to any one of embodiments 1-79, including application of said stimulus.

Embodiment 105: The apparatus according to any one of embodiments 99-102, wherein said apparatus is configured to perform the method according to any one of embodiments 1-79, including application of said stimulus where said stimulus comprises restricting flow of blood to a limb by occlusion of a blood vessel.

Embodiment 106: The apparatus of embodiment 105, wherein said apparatus is configured to restrict the flow of blood using a cuff Embodiment 107: The apparatus of embodiment 106, wherein said apparatus is configured to restrict the flow of blood and apply the pressure on the artery using separate cuffs.

Embodiment 108: The apparatus of embodiment 106, wherein said apparatus is configured to use the same cuff to occlude the blood vessel and to apply the pressure on the artery.

Embodiment 109: The apparatus according to any one of embodiments 82-83, wherein said apparatus is configured to restrict flow of blood through the artery by inflating the restricting cuff to a pressure at least 10 mm Hg above measured systolic blood pressure for said mammal.

Embodiment 110: The apparatus according to any one of embodiments 105-109, wherein said apparatus is configured to restrict flow of blood through the artery for at least 1 minute.

Embodiment 111: The apparatus according to any one of embodiments 99-110, wherein said controller is configured to apply pressure to said cuff during one or more time periods ($T_m$) by adjusting a pump or other pressure source and/or a proportional release valve to maintain a desired pressure.

Embodiment 112: The apparatus according to any one of embodiments 99-111, said controller is configured to stop adjustment of said pressure during said time period(s).

Embodiment 113: The apparatus according to any one of embodiments 99-111, wherein said controller is configured to periodically adjust said pressure using an on-off control system during said time period(s).

Embodiment 114: The apparatus according to any one of embodiments 99-111, wherein said controller is configured to continuously increase or decrease said pressure during said time period(s).

Embodiment 115: The apparatus according to any one of embodiments 99-111, wherein said controller is configured to maintain pressure within a pressure range (ΔP) around said measurement set point during said time period(s).

Embodiment 116: The apparatus of embodiment 115, wherein said pressure range (ΔP) ranges from about 1 mm Hg to about 6 mm Hg, or from about 1 mm Hg to about 4 mm Hg, or from about 1 mm Hg to about 3 mm Hg, or from about 1 mm Hg to about 2 mm Hg.

Embodiment 117: The apparatus of embodiment 116, wherein said pressure range (ΔP) is about 2 mm Hg.

Embodiment 118: The apparatus according to any one of embodiments 99-117, wherein apparatus is configured to provide a time interval duration ranging from about 1 sec, or from about 2 sec, or from about 3 sec, or from about 4 sec, or from about 5 sec, or from about 6 sec, or from about 7 sec, or from about 8 sec, or from about 9 sec, or from about 10 sec, or from about 15 sec up to about 20 sec, or up to about 30 sec or up to about 40 sec or up to about 50 sec, or up to about 1 min, or up to about 2 min, or up to about 3 min, or up to about 4 min, or up to about 5 min, or up to about 6 min, or up to about 7 min, or up to about 8 min, or up to about 9 min, or up to about 10 min, or up to about 15 min, or up to about 20 min, or up to about 25 min, or up to about 30 min.

Embodiment 119: The apparatus according to any one of embodiments 99-118, wherein said controller is configured to monitor and adjust said pressure at a response time sufficiently slow so that said pressure changes resulting from said cardiac activity are attenuated by less than 10%.

Embodiment 120: The apparatus according to any one of embodiments 99-119, wherein said controller is configured to maintain said external pressure by setting the pressure in said cuff to a value and not altering external pressure applied to said cuff during the measurements of pressure variations due to said cardiac activity.

Embodiment 121: The apparatus according to any one of embodiments 99-120, wherein said controller is configured to apply an external pressure equivalent to or below a diastolic pressure determined for said subject.

Embodiment 122: The apparatus according to any one of embodiments 99-120, wherein said controller is configured to apply an external pressure below the average diastolic pressure measured for said subject or below an expected diastolic pressure for said subject.

Embodiment 123: The apparatus according to any one of embodiments 99-120, wherein said controller is configured to apply an external pressure below the average diastolic pressure measured for said mammal, but no less than about 10 mmHg below said average diastolic pressure.

Embodiment 124: The apparatus according to any one of embodiments 99-123, wherein said controller is configured to apply a constant pressure at different levels during different measurement intervals.

Embodiment 125: The apparatus according to any one of embodiments 99-124, wherein the measurement apparatus comprises a hydraulic or pneumatic pump adapted to apply the pressure to said cuff.

Embodiment 126: The apparatus according to any one of embodiments 99-125, wherein said response time is reduced by disposing a narrow pressure line between hydraulic or pneumatic pump and said cuff.

Embodiment 127: The apparatus according to any one of embodiments 99-126, wherein said apparatus comprises a valve and a pump configured to provide on-off control of the pressure in said cuff.

Embodiment 128: The apparatus according to any one of embodiments 99-127, wherein said apparatus further comprises an accelerometer disposed to detect movement or vibrations in said cuff or apparatus.

Embodiment 129: The apparatus according to any one of embodiments 99-128, wherein said cuff is pressurized with a material selected from the group consisting of a gas, a fluid, and a gel.

Embodiment 130: The apparatus according to any one of embodiments 99-129, wherein said cuff is adapted to apply pressure substantially around an entire circumference of a limb including the artery.

Embodiment 131: The apparatus according to any one of embodiments 99-129, wherein said cuff is adapted to apply a local pressure that does not substantially affect other blood vessels in a same limb as the artery.

Embodiment 132: The apparatus according to any one of embodiments 99-131, wherein said processor is configured to determine a blood pressure.

Embodiment 133: The apparatus of embodiment 132, wherein said processor is configured to calculate said external pressure based on one or more blood pressure measurements and to direct said controller to apply the calculated external pressure.

Embodiment 134: The apparatus according to any one of embodiments 99-133, wherein the controller is configured to induce at least one of measurement round responsive to an indication that a stimulus was administered to the artery and at least one of the measurement rounds before the indication that the stimulus was administered to the artery is received.

Embodiment 135: The apparatus according to any one of embodiments 99-134, wherein the controller is adapted to apply the pressure continuously over at least five cardiac cycles of the patient.

Embodiment 136: The apparatus according to any one of embodiments 99-135, wherein the controller is configured to store over the course of one or more cardiac cycles, changes in pressure in said cuff resulting from cardiac activity of said mammal as a function of time.

Embodiment 137: The apparatus according to any one of embodiments 99-136, wherein said processor is configured to integrate the value of a pressure change over time (calculate the area under a pressure/time curve) for one or for a plurality of cardiac cycles to determine an integrated pressure value.

Embodiment 138: The apparatus according to any one of embodiments 99-137, wherein said processor is configured to determine the maximum of the derivative of the pressure versus time wave form on the rising edge of a pressure pulse for one or for a plurality of cardiac cycles to determine a compliance value.

Embodiment 139: The apparatus according to any one of embodiments 137-138, wherein said processor is configured to average said integrated pressure value and/or said compliance value over a plurality of cardiac cycles.

Embodiment 140: The apparatus according to any one of embodiments 137-138, wherein said processor is configured to determine said integrated pressure value and/or said compliance value a single cardiac cycle.

Embodiment 141: The apparatus according to any one of embodiments 137-138, wherein said processor is configured to determine said integrated pressure value and/or said compliance value and identify a maximum change in said value between a baseline measurement and a stimulus-effected measurement.

Embodiment 142: A method of treating a subject for a cardiovascular pathology, said method comprising: assessing endothelial function in said subject using the method according to any one of embodiments 1-98; and where said method produces a measure indicating impaired endothelial function, evaluating said measure in the context of a differential diagnosis for a cardiovascular pathology and, where indicated, performing one or more interventions for the treatment of a cardiovascular pathology.

Embodiment 143: The method of embodiment 142, wherein said assessing endothelial function is performed using an apparatus according to any one of embodiments 99-141.

Embodiment 144: The method according to any one of embodiments 142-143, wherein said cardiovascular pathology comprises a pathology selected from the group consisting of atherosclerosis, hypercholesterolemia, high LDL-C, low HDL-C, high lipoprotein (a), small dense LDL-C, oxidized LDL-C, hypertension, high homocysteine, aging, vasculitis, preeclampsia, metabolic syndrome, variant angina, diabetes, active smoking, passive smoking, ischemia-reperfusion, transplant atherosclerosis, cardiopulmonary bypass, postmenopausal, Kawasaki's disease, Chagas' disease, family history CAD, infections, depression, inactivity, obesity, renal failure, increased CRP, congestive heart failure, and left ventricular hypertrophy.

Embodiment 145: The method according to any one of embodiments 142-143, wherein said cardiovascular pathology comprises atherosclerosis.

Embodiment 146: The method according to any one of embodiments 142-145, wherein said intervention is selected from the group consisting of prescribing and/or administering ACE inhibitors, prescribing and/or administering angiotensin receptor blockers, prescribing and/or administering endothelin blockers, prescribing and/or administering statins, prescribing and/or administering tetrahydrobiopterin, prescribing and/or administering folates, improving insulin sensitivity, LDL reduction, HDL augmentation, prescribing and/or administering antioxidants, prescribing and/or administering estrogen, prescribing and/or administering L-arginine, prescribing and/or administering desferoxamine, prescribing and/or administering glutathione, homocysteine reduction, lowering CRP, and reducing free fatty acid flux.

DETAILED DESCRIPTION

In various embodiments, methods and devices are provided for non-invasively assessing arterial endothelial function in a mammal (e.g., a human or a non-human mammal), particularly in response to a stimulus. The change in endothelial function (or lack of change) in response to particular stimuli provides a measure of the vascular health of the subject.

In certain embodiments the method and devices are configured to provide cuff-based flow-mediated vasodilation (cFMD) measurements, however, in various embodiments, methods and apparatus are provided to convert cFMD measurements to equivalent ultrasound-based flow-mediated FMD (uFMD) measurements, where ultrasound imaging or vessel wall tracking are used to determine the diameter of an artery before and after the delivery of endothelial stimulus.

Determination of cFMD Measurements and Conversion of uFMD Measurements.

Figure 1:
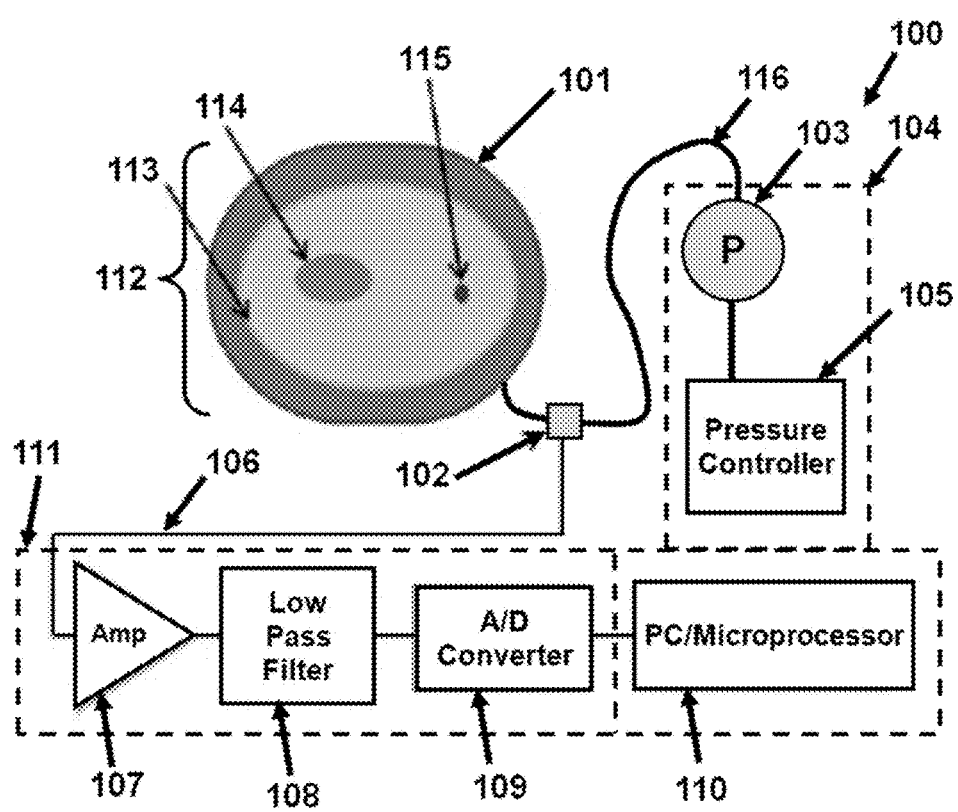
FIG. 1 provides a schematic illustration of a system 100 for assessing arterial endothelial function in a mammal.

Consider FIG. 1 which provides a schematic representation of the cross section of the human upper arm 112 enclosed in an inflated blood pressure cuff 101. In conventional blood pressure measurement, the cuff is initially inflated above the systolic blood pressure. This applies pressure to the skin surface 113 which compresses the arm and the contents thereof (e.g., humerus 114, brachial artery 115, etc.) causing the underlying arteries 115 to collapse. The pressure in the cuff in this case is purely determined by the external pressure applied by the air in the cuff.

Consider the case where the cuff is inflated to a pressure below diastolic pressure. This distorts the shape of the artery causing the artery to partially collapse. As the pressure in the artery increases during the course of the natural blood pressure pulse (i.e., exceeds the diastolic pressure), the flattened artery expands. As a consequence of the near incompressibility of human tissue and body fluids, the pressure in the cuff increases in proportion to the increase in arterial cross sectional area. By measuring the pressure in the cuff, it is thus possible to obtain a measure of arterial caliber.

Consider an illustrative example, where 70 mm Hg pressure is applied to the cuff when the subject's diastolic pressure is 80 mm Hg. In certain embodiments this is accomplished by attaching a constant pressure source 103 to the cuff that provides the 70 mm Hg pressure. In various embodiments the constant pressure source 103 utilizes a hydraulic or pneumatic pump or pressurized gas, or a fluid reservoir. Such sources typically utilize a servo/valve mechanism to maintain the pressure set point, and this servo can be under control of a pressure controller 105. In some embodiments, a pump and valve are actuated by a control system in order to keep the pressure within an acceptable range (e.g. ±5 mm Hg) about the set point.

To preserve pressure signals resulting from cardiac activity (i.e., cardiac cycle(s)) it is desirable that the pressure source not substantially cancel out the changes in cuff pressure due to the increase in area of the flattened vessel. This may be achieved by increasing the time constant of the system response of the servo/pressure controller system and/or more simply by placing a flow resistor 116 between the pressure source and the cuff. In the simplest implementation, a long thin tube (e.g., 1 m (or other) length of thin intervening tubing that serves as a pneumatic low pass filter) can provide this resistance. Another option is to decouple the constant pressure source from the cuff once the cuff has reached its target pressure.

In various illustrative embodiments, the time constant of the pressure system is sufficiently slow relative to pressure changes introduced by the cardiac cycle that pressure changes resulting from cardiac activity (e.g., pulse-associated pressure changes) are attenuated by less than 20%, or less than about 15%, or less than about 10%, or less than about 5%, or less than about 1% of the maximum pressure change. Similarly a substantially constant pressure is a pressure that when averaged over a sufficiently long time period that pulse-induced pressure changes are averaged out, the average pressure applied to the cuff over the desired time period various by less than 20%, more preferably less than about 15%, or less than about 10%, most preferably less than about 5%, 3%, 2%, or 1% of the applied pressure.

In various embodiments the pressure in the cuff is measured using a pressure transducer (pressure sensor) 102. One illustrative suitable pressure sensor is the Millar catheter pressure sensor (Mikro-tip, Millar Instruments, Houston, Tex.). The output signal of transducer can be amplified (e.g., using an instrumentation amplifier such as AD627, Analog Devices, Inc., Norwood Mass.), optionally low-pass filtered (e.g., using 8th Order elliptic Filter, LTC-1069-6, Linear Technology Corp., Milpitas, Calif.), and then digitized (e.g., at 1 kHz using a A/D converter PCI card (NI-6035, National Instruments, Austin, Tex.).

The digitized signal can be directly interpreted as a quantity proportional to the area of the arterial lumen as long as the pressure in the cuff is less than the systolic pressure of the subject, and as long as the pressure at the outlet of the pressure source is held substantially constant. The pressure source we used in one prototype (Hokanson E20, Bellevue, Wash.) provides servo regulation that is too fast to allow its direct application to the cuff without attenuating the signal due to the expansion of the arterial lumen. Consequently, we employed a 1 m length of thin intervening tubing to serves as a pneumatic low pass filter.

An illustrative, but non-limiting, protocol can involve the following steps (see also flow chart in FIG. 9):

1. The subject is seated or lies supine and rests briefly, e.g., for five minutes.
2. The subject's blood pressure is measured.
3. The cuff is inflated to at or, somewhat below, the diastolic pressure (e.g., 10 mm Hg below the diastolic blood pressure) and the pressure signal is recorded to determine a baseline value for a parameter related to endothelial function in said mammal (e.g. integrated pressure as a function of time).
4. A stimulus is applied to the subject.
5. A pressure signal is recorded with the cuff inflated to at or, preferably somewhat below, the diastolic pressure (e.g., 10 mm Hg below the diastolic blood pressure) and the pressure signal is recorded to determine a stimulus-effected value for a parameter related to endothelial function in said mammal (e.g. integrated pressure as a function of time).
6. The stimulus-effected value of the parameter is compared to the baseline value of the parameter to determine presence, absence, and/or degree of endothelial response to said stimulus.

Any of a number of different types of stimuli can be used. Typically, however, the stimulus is one expected to have an effect on endothelial function in a mammal. Such stimuli include, but are not limited to occlusion of blood flow, application of drugs (e.g., NO agonists, $\beta_2$-adrenergic agonists such as albuterol, acoustic/mechanical tissue vibration, ultrasound stimulus, and the like).

One illustrative non-limiting protocol where the stimulus comprises occlusion of blood flow can involve the following steps:

1. Subject is seated or lies supine and rests, e.g., for five minutes.

2. The subject's blood pressure is measured.

3. The cuff is inflated to 10 mm Hg below the diastolic blood pressure for one minute. During this time, the pressure signal is recorded to determine a baseline value for a parameter related to endothelial function in said mammal.

4. The cuff is deflated for 30 seconds to allow blood flow to return toward normal.

5. The cuff is inflated to, e.g., 40 mm Hg above systolic pressure for five minutes.

6. The cuff is released to allow reactive hyperemia to ensue, e.g., a release for 35 seconds.

7. The cuff is inflated to, e.g., 10 mm Hg below the diastolic blood pressure for three minutes. During this time, the pressure signal is recorded to determine a stimulus-effected value for a parameter related to endothelial function in said mammal.

8. The stimulus-effected value of the parameter is compared to the baseline value of the parameter to determine presence, absence, and/or degree of endothelial response to said stimulus.

A second illustrative non-limiting protocol where the stimulus comprises occlusion of blood flow can involve the following steps:

1. Subject is seated or lies supine and rests for five minutes.

2. The cuff begins inflating rapidly to, e.g., 20 mmHg.

3. The cuff is inflated at a rate of 3-6 mmHg/s and the pulse waveform is monitored and recorded throughout.

4. The maximum amplitude of the pulse waveform is detected as the cuff pressure becomes close to mean arterial pressure (MAP).

5. Cuff inflation continues until the amplitude of the pulse waveform is attenuated below a certain threshold (usually a fraction of the maximum amplitude obtained near MAP).

6. The cuff is deflated suddenly. Alternatively, the cuff is deflated slowly, e.g., at a rate of 3-6mmHg/s.

7. After a rest period of 30 seconds, the blood flow in the limb is occluded, e.g., for 60-300 s.

8. The occlusion is released. A rest period of, e.g., 45 seconds follows.

9. Steps 2-6 are repeated to obtain a post stimulus measurement.

10. The stimulus-effected value of the parameter is compared to the baseline value of the parameter to determine presence, absence, and/or degree of endothelial response to said stimulus. The analysis of the waveforms recorded yields systolic blood pressure (SBP), diastolic blood pressure (DBP), an estimate of MAP (the maximum amplitude of the oscillometric waveform). Comparison of the waveforms to estimate endothelial function are referenced to the values of SBP, DBP and MAP obtained.

Calculation of uFMD from cFMD.

In various embodiments the methods described above can be performed in a manner that facilitates conversion of cFMD measurements to equivalent ultrasound-based flow-mediated FMD (uFMD) measurements, e.g., uFMD measurement where ultrasound imaging or vessel wall tracking are used to determine the diameter of an artery before and after the delivery of endothelial stimulus. Thus, methods and devices are provided that permit measurement and conversion of cFMD measurement to equivalent uFMD measurements, e.g., as described in Example 3.

Accordingly in various embodiments the methods described above can comprise:

a) applying external pressure $P_m$ to an artery for a period of time $T_m$, and determining, over the course of one or more cardiac cycles in period $T_m$, changes in pressure in a cuff resulting from cardiac activity of the mammal, or an artificially induced arterial pulse, to determine values for a baseline parameter related to endothelial function in the mammal, where said baseline parameter is determined for at least three different external pressure points ($P_m$) (or at least 3 different external pressure points during a continuous pressure variation) by varying the external pressure $P_m$ during period of time $T_m$, and/or by determining said baseline parameter over a plurality of time periods $T_m$ having different external pressure points ($P_m$), to provide a plurality of baseline values for said parameter related to endothelial function as a function of applied pressure ($P_m$);

b) applying a stimulus to the mammal; and c) applying external pressure $P_m$ to an said artery for a period of time $T_m$, and determining over the course of one or more cardiac cycles in period $T_m$, changes in pressure in the cuff resulting from cardiac activity of the mammal, or an artificially induced arterial pulse, to determine values for a stimulus-effected parameter related to endothelial function in said mammal, where said stimulus-effected parameter is determined for at least three different external pressure points ($P_m$) (or at least 3 different external pressure points during a continuous pressure variation) by varying the external pressure $P_m$ during period of time $T_m$, and/or by determining said parameter over a plurality of time periods $T_m$ having different external pressure points ($P_m$), to provide a plurality of stimulus-effected values for the parameter related to endothelial function as a function of applied pressure ($P_m$); wherein the baseline values are determined from measurements made when said mammal is not substantially effected by the stimulus and differences in said baseline values and said stimulus-effected values provide a measure of endothelial function in said mammal.

It will be recognized that in certain embodiments the variations in pressure (e.g., varying external pressures) can be a multiple discrete pressures permitting measurements to be made at those multiple discrete pressures. In certain other embodiments the variations in pressure can be continuous variations in pressure, and the measurements are made during the continuously varying pressure. Where the pressure is varied (e.g., continuously varied) the variation can be monotonic or non-monotonic.

In certain embodiments the methods described above (and in the examples) can comprise:

d) determining the area of the arterial lumen calculated from the baseline pressure measurements as a function of transmural pressure $P_{tm}$, where transmural pressure is determined as the difference between the baseline measured pressures and the external cuff pressure $P_m$ and fitting these data with a first non-linear model to provide a first function describing baseline arterial lumen area as function of transmural pressure;

e) determining the area of the arterial lumen calculated from the stimulus-effected pressure measurements as a function of transmural pressure $P_{tm}$, where transmural pressure is determined as the difference between the measured stimulus-effected pressures and the external cuff pressure $P_m$ and fitting these data with a second non-linear model to provide a second function describing stimulus-effected arterial lumen area as function of transmural pressure;

f) using said the function to calculate baseline arterial lumen area ($A_b$) at a transmural pressure substantially equal to the systolic blood pressure;

g) using said second function to calculate stimulus-effected arterial lumen area ($A_r$) at a transmural pressure substantially equal to the systolic blood pressure; and h) determining the equivalent ultrasound-based FMD (uFMD) measure where uFMD is proportional to the square root of the ratio $A_r/A_b$.

In certain embodiments the cuff is fully calibrated so that luminal area can be calculated. However, in various embodiments, this is not required since the ratio of uncalibrated area estimates is independent of this calibration. Thus, in various embodiments, the term "area" refers to a quantity proportional area even if it is not an absolutely calibrated area.

In certain embodiments, the equivalent ultrasound-based FMD is given as:

$$uFMD\% = [\sqrt{(A_r/A_b)} - 1] \times 100$$

In various embodiments the first non-linear model and/or the second non-linear model are the same type of function. In certain embodiments the first non-linear model and/or the second non-linear model are selected from the group consisting of a 2-parameter model, a 3 parameter model, a four parameter model, a 5 parameter model, and a six parameter model. In certain embodiments the first non-linear model and/or the second non-linear model are three parameter models. In various embodiments the first non-linear model and/or the second non-linear model are arctangent models.

In various embodiments step (a) and/or step (b) of the method comprises determining values for a baseline parameter and/or values for a stimulus-effected parameter for at least 3 different pressure points ($P_m$), or for at least 4 different pressure points ($P_m$), or for at least 5 different pressure points ($P_m$), or for at least 6 different pressure points ($P_m$), or for at least 7 different pressure points ($P_m$), or for at least 8 different pressure points ($P_m$), or for at least 9 different pressure points ($P_m$), or for at least 10 different pressure points ($P_m$).

In various embodiments step (a) and/or step (b) of the method comprises determining values for a baseline parameter and/or values for a stimulus-effected parameter for at least 3 different pressure points ($P_m$) during a continuous pressure variation, or for at least 4 different pressure points ($P_m$) during a continuous pressure variation, or for at least 5 different pressure points ($P_m$) during a continuous pressure variation, or for at least 6 different pressure points ($P_m$) during a continuous pressure variation, or for at least 7 different pressure points ($P_m$) during a continuous pressure variation, or for at least 8 different pressure points ($P_m$) during a continuous pressure variation, or for at least 9 different pressure points ($P_m$) during a continuous pressure variation, or for at least 10 different pressure points ($P_m$) during a continuous pressure variation.

In various embodiments the external pressure is less than the mean arterial pressure. In certain embodiments external pressure is less than the mean diastolic pressure.

In certain embodiments the external pressure (Pm) ranges from about 20 mmHg up to about 80 mmHg.

In certain embodiments the external pressure points ($P_m$) used to determine the baseline values are substantially the same as the external pressure points (PM) used to determine the stimulus-effected values or the external pressure points ($P_m$) used to determine the baseline values are different than the external pressure points (PM) used to determine the stimulus-effected values.

In various embodiments the baseline parameter is determined for at least three different external pressure points ($P_m$) by varying the external pressure $P_m$ during period of time $T_m$, and/or by determining said baseline parameter over a plurality of time periods $T_m$ having different external pressure points ($P_m$).

As noted above, in various embodiments, the pulse waveform is determined throughout the cuff inflation and/or deflation. In certain embodiments the cuff inflation and/or deflation is at a rate of about 3-6 mm Hg per second. Analysis of the pulse waveform yields systolic blood pressure (SBP), diastolic blood pressure (DBP), an estimate of MAP (the maximum amplitude of the oscillometric waveform). Comparisons of the waveforms to estimate endothelial function are referenced to the values of SBP, DBP and MAP obtained. In certain embodiments the pulse waveforms obtained in this way can be compared between baseline and post-stimulus conditions, either by direct comparison of pulse characteristics at corresponding pressure levels, or by first fitting models (e.g. a non-linear model such as a 2 parameter model, a 3 parameter model, a four parameter model, a 5 parameter model, and a six parameter model, etc.) to each set and comparing the parameters obtained from the fitted models those models. Illustrative pulse characteristics (parameters) related to endothelial function include, but are not limited to the peak value of a pressure pulse or the maximum peak value of a number of pressure pulses, or the average or median peak value of a number of pressure pulses. Other illustrative parameters include, but are not limited to the area under a pulse in a pressure versus time plot (i.e., the integrated value of pressure as a function of time) for a pulse, the peak integrated value of a series of pulses, or the average or median integrated value of a series of pulses. Another useful parameter is the derivative of the area vs. time waveform, e.g., the maximum of this derivative on the rising edge of the pulse. If the endothelial stimulus does not affect systemic systolic or diastolic blood pressure (which is a very reasonable assumption), we can assume that the pressure at the point at which the slope of the area versus time curve is maximal is approximately the same before and after endothelial stimulus. In this case, this slope is an approximately proportional to dA/dP, which is the compliance of the vessel (A and P represent area and pressure, respectively). Compliance is the fundamental quantity reduced by the smooth muscle relaxation that is a consequence of healthy endothelial response. It constitutes a extremely valuable "root cause" metric.

In various embodiments blood pressure (BP) and cFMD can be measured in one set of readings. The advantage of this approach is that the features related to BP are provided in the same continuous measurement as the features used for cFMD determination. If BP varies between baseline and post-stimulus intervals, this can be detected and the measurement can be disqualified or compensated for, since the baseline and post-stimulus data sets can be compared as a function of transmural pressure, not measurement pressure.

Accordingly, in one illustrative, but non-limiting approach, the cuff is inflated (perhaps slowly, e.g., at 3-6 mm Hg/s) to a pressure in excess of the peak of the oscillometric waveform. When inflation is to a pressure in excess of the systolic pressure, this pressure may be identified as a certain level of diminution of the amplitude of the waveform, as in the standard oscillometric methods. Typically inflation will be to a pressure that identifies the peak of the oscillometric waveform, which is generally taken to represent the mean arterial pressure (MAP). After identifying the systolic BP and MAP, the diastolic BP may be calculated according to standard methods used to implement oscillometric determination of BP (e.g., as reviewed and discussed by Babbs (2012) *BioMedical Engineering OnLine,* 11:56 DOI: 10.1186/1475-925X-11-56i.). Additionally, or alternatively, in certain embodiments, the diastolic blood pressure (DBP) can be identified by analyzing Korotkoff sounds obtained using an audio sensor (stethoscope, phonocadiogram), or ultrasound probe. In certain embodiments after reaching the inflation pressure, the presser can be slowly released and one or more sets of measurements can be made to calculate cFMD and/or MAP, and/or DBP during cuff deflation. Alternatively, the cuff can simply be deflated, having obtained all measurements determined during slow inflation.

In certain embodiments for cFMD determination, a comparison of pulse waveform characteristics between baseline and post-stimulus intervals at "corresponding pressures" can be a comparison made where the corresponding pressures are transmural pressures calculated using the BP values obtained as described above, rather than comparisons based on corresponding measurement (cuff) pressures. In certain embodiments, when two fitted models are compared, the comparisons can be based on transmural pressure as the pressure variable.

In certain embodiments measurements of the same mammal are obtained several times. Then previous measurements can be used to establish the tone state of the vessel at the current time at baseline and the degree of current dilation (tone state) at baseline can be used to adjust the cFMD and BP measurements to the current vessel tone state, in a manner suggested by Babbs (2012), supra. In certain embodiments the maximal dilated state is measured by stimulating the vessel with an NO donor such as nitroglycerin and/or the constricted state is measured by stimulating the vessel with a vasoconstrictive substance such as phenylephrine. In certain embodiments the dilatory and constrictory potential of the vessel and tone state are inferred by measurements obtained with the cuff elevated at different vertical levels with respect to the heart. This varies the hydrostatic pressure on the wall and enables characterization of vessel mechanics.

In view of the foregoing, it will be recognized that cFMD determinations, using a comparison of pulse waveform characteristics between baseline and post-stimulus intervals at corresponding transmural pressures calculated using the determined BP values can be used to calibrate the threshold points used for oscillometric determination of the DBP, as may be understood from Babbs (2012), *supra.*

The oscillometric method has been relatively well validated as a measure of mean arterial pressure, which is indicated by the peak of the oscillation amplitude envelope. Use of the oscillometric method in screening for high blood pressure has proven problematic, because the accuracy of systolic and diastolic end points has been questioned and doubted. However, in certain embodiments, a model describing the dependence of the oscillometric characteristic on vessel tone can be used to refine thresholds for oscillometric determination of DBP. One illustrative such model is described by Babbs (2012) *BioMedical Engineering OnLine,* 11:56 DOI: 10.1186/1475-925X-11-56i. Determinations of vessel tone using the methdos and devices described herein can be used to change the calibration of the thresholds used for DBP determination by the oscillometric method and provide accurate systolic and diastolic end points. In cases where maximally-dilating stimuli such as nitroglycerin (NG) are used, subsequent studies without NG may use the NG study as reference of maximum dilation. The endothelium-mediated dilation measurements calibrated for the maximum attainable dilation. In cases where NG is employed at a similar time to the endothelial function study, the baseline tone, and tone after endothelial stimulus, may be assessed by comparison to the maximally dilated state.

As noted above, amount of FMD measured by any method is dependent on the initial vessel tone (tension state of the arterial vascular smooth muscle). A fully dilated vessel cannot, by definition, exhibit additional dilation in response to a stimulus. Ideally, a stimulus such as nitroglycerin can be applied to assess the maximum dilation capacity of the vessel. However, when multiple measurements are performed on an individual over time, the natural variation of these states can be "learned" by an algorithm. This may be used to obtain refined estimates of not only endothelial function, but also DBP and MAP, which are also substantially dependent on arterial tone, and, to a lesser extent, heart rate. By repeatedly applying protocols described above, a large portion of the characteristic curve: (luminal area change as a function of pulse pressure, as represented by the distension waveform recorded as pressure changes in the cuff) versus transmural pressure, is acquired under several different natural conditions. This enables an algorithm to learn this characteristic, which as Bank et al. (1999) *Circulation,* 100: 41-47, have proven, is dependent on vessel tone. Specifically, the data obtained from the baseline recordings can improve measurements of SBP, DBP and MAP, regardless of the intactness of endothelial function in the mammal. The major effect of prevailing tone at the time of BP measurement, on values of DBP obtained via the oscillometric method, has been demonstrated by Babbs, and others. It is also known that these estimates are also dependent on pulse shape and heart rate. All of this information can be recorded in the baseline and post-stimulus pressure waveforms acquired by various embodiments of the invention described herein, and enables an algorithm to more accurately estimate both BP and endothelial function based on estimating the tone state of the vessel.

Figure 2:
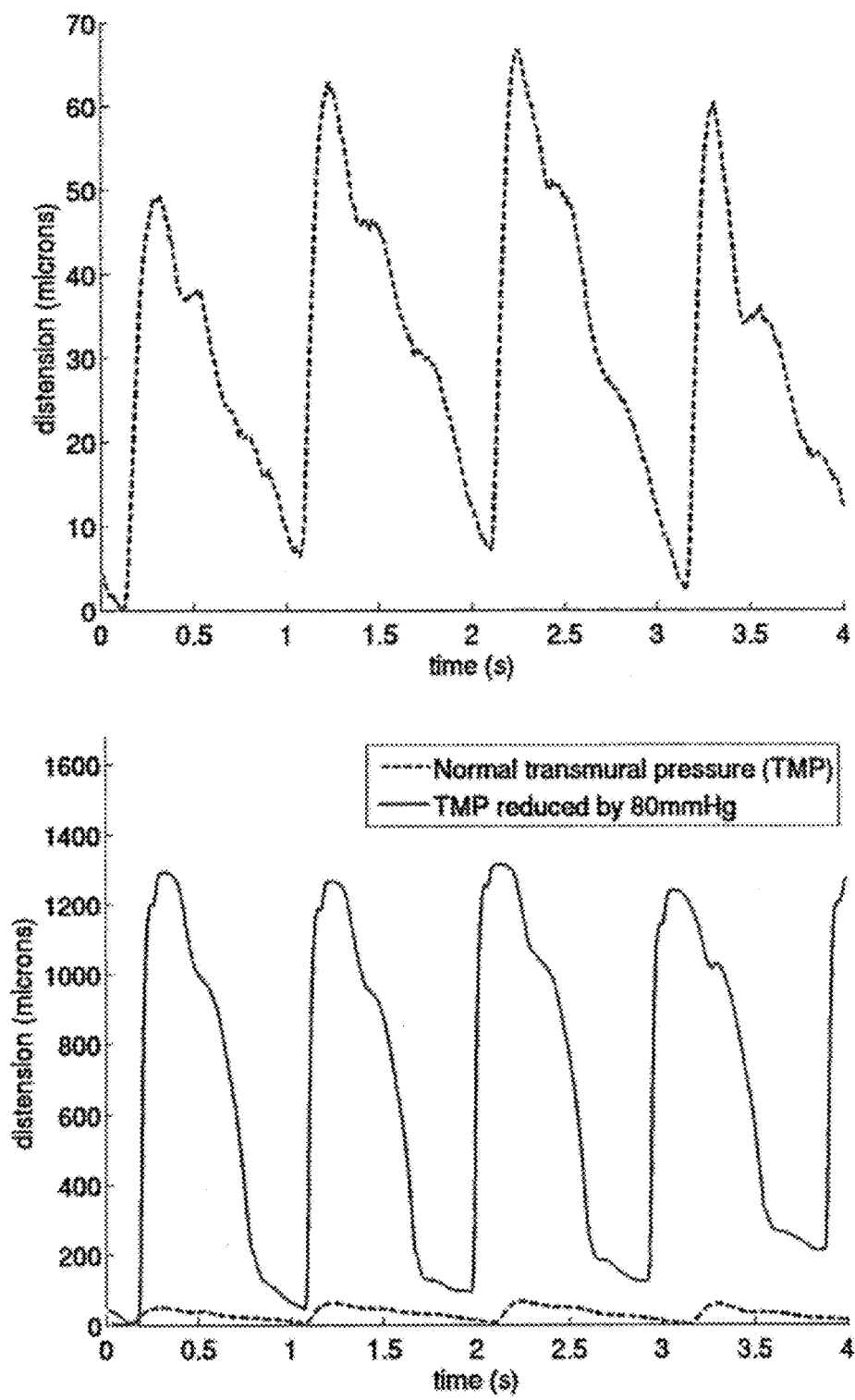
FIG. 2 shows distension of the brachial artery recorded by M-mode wall tracking. Top: Distension waveform under normal conditions. Bottom: When the transmural pressure is decreased by 80 mm Hg using an external cuff, the maximum distention of the artery increases more than twentyfold over baseline conditions.

A fundamental advantage of the present methods over traditional measures of flow-mediated vasodilation (FMD) is the increased sensitivity that comes from measuring parameters related to arterial cross-sectional area rather than radius, since area is approximately proportional to the square of the radius. Also, by decreasing the transmural pressure on the artery using an external cuff inflated just below diastolic levels, the distensibility of the artery is increased by more than an order of magnitude (Bank et al. (1995) Circ. Res., 77(5): 1008-1016; Bank et al. (1999) *Circulation,* 100: 41-47; Kim et al. (2004) *Ultrasound in Medicine & Biology,* 30: 761-771). As FIG. 2 illustrates, we have observed this effect in our laboratory using M-mode ultrasound to track the arterial wall. These two factors combined lead impart exceptionally high sensitivity to the methods and devices described herein.

In various embodiments, the R-wave of the patient ECG can be used as a timing reference to facilitate the analysis of individual pulses. In certain embodiments it is possible, however, to perform such analysis using the pressure waveform alone.

Figure 3:
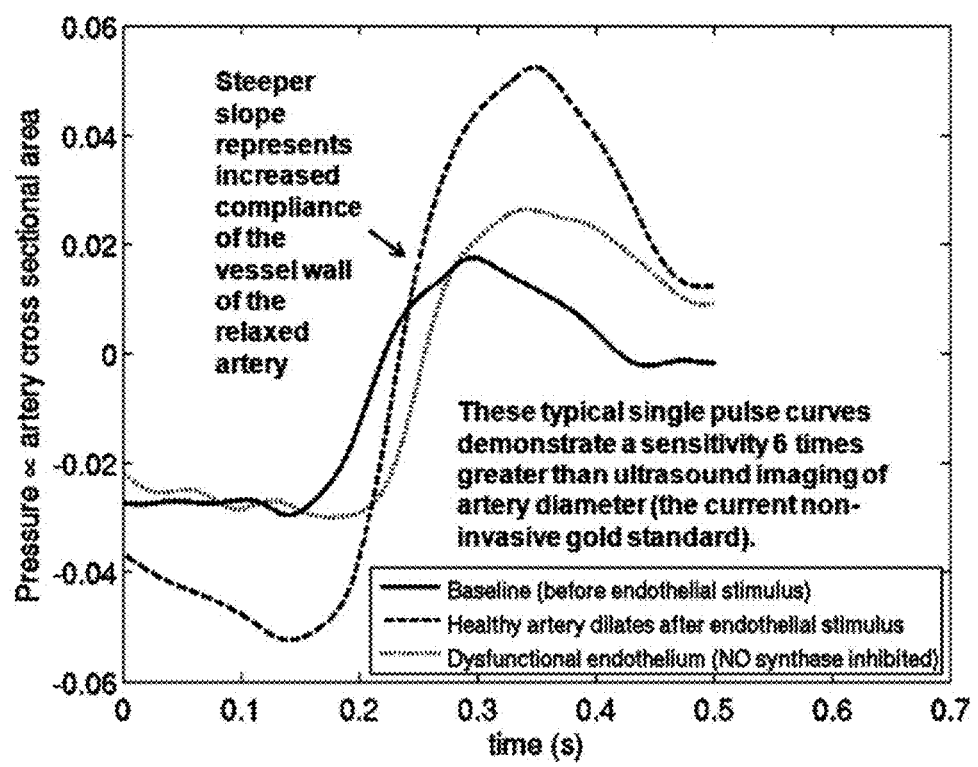
FIG. 3 shows typical single pulse waveforms obtained from the pressure cuff when inflated to 70 mm Hg. Both the amplitude and slope of the rising edge of the pulse increase markedly after endothelial stimulation. This individual thus exhibits intact endothelial response. Administration of the NO synthase inhibitor L-NAME greatly attenuates this response, suggesting that the measurement is primarily sensitive to NO-mediated vasodilation.
Figure 4:
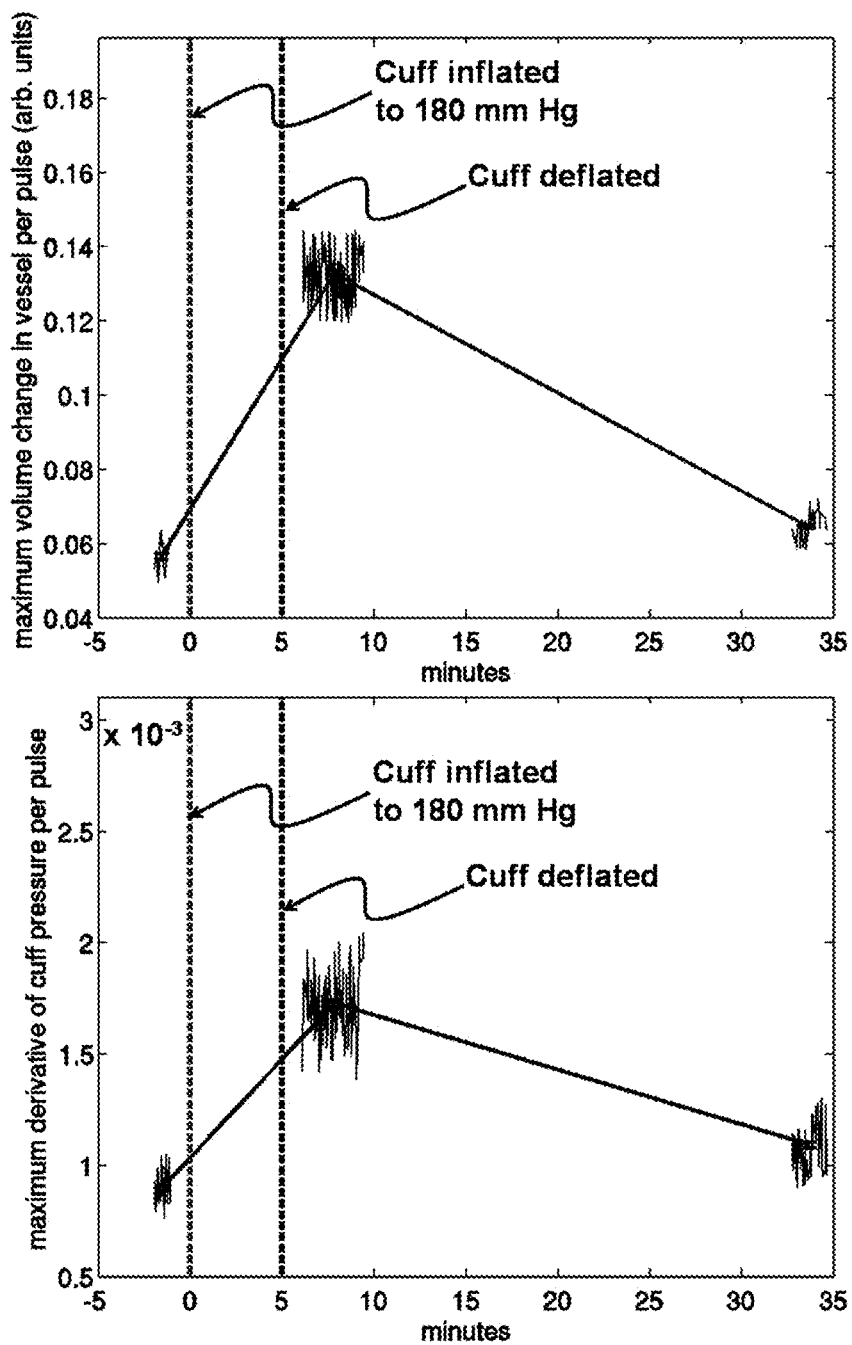
FIG. 4 shows results of a study of the effects of a five minute cuff occlusion on the area (upper panel) and maximum derivative of the area vs. time curve (lower panel). Both quantities increase markedly after cuff release but have returned to baseline levels after 25 minutes.
Figure 5:
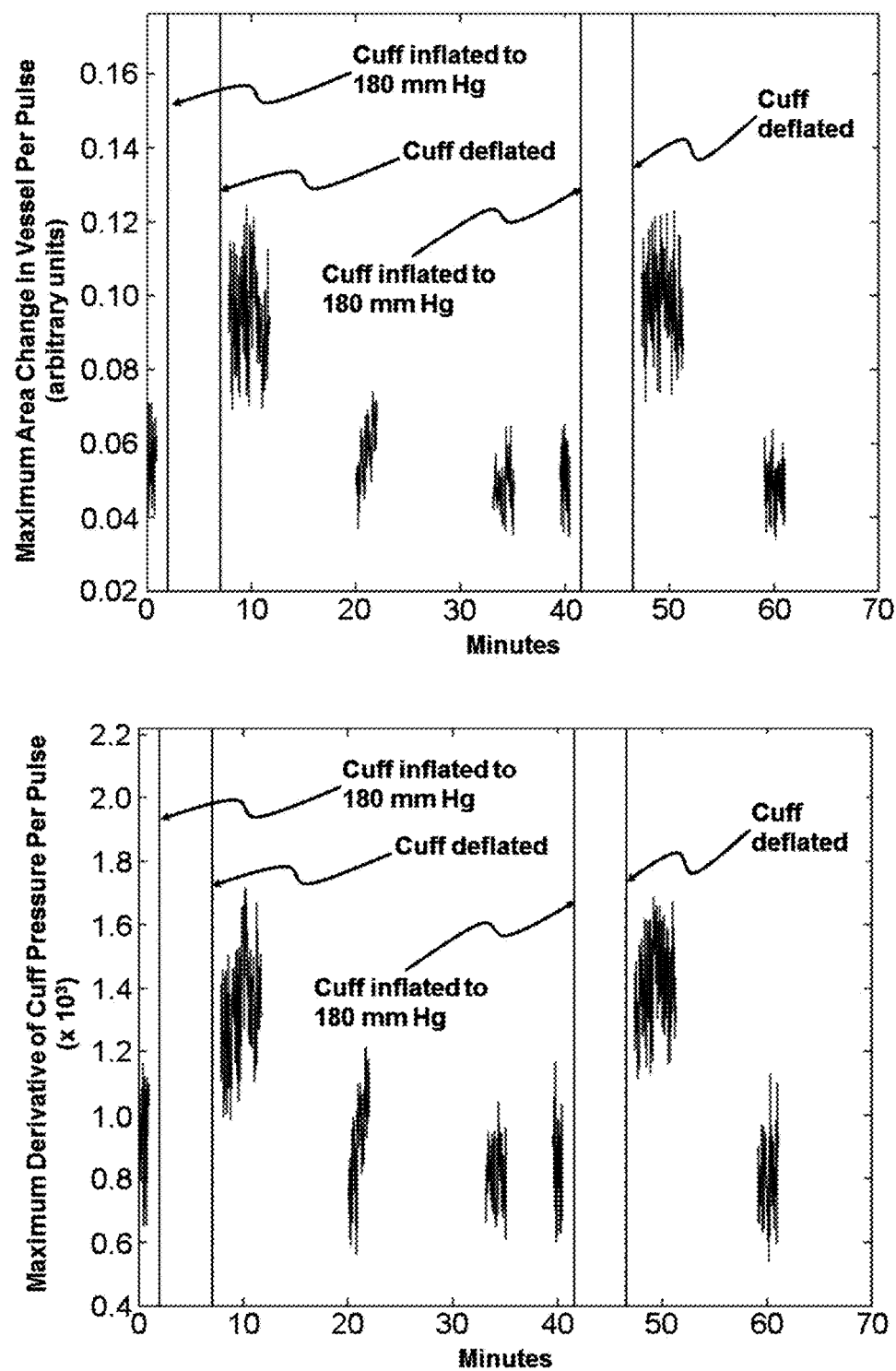
FIG. 5 shows results of a study of the effects of two serial five minute cuff occlusions on the area (upper panel) and maximum derivative of the area vs. time curve (lower panel). Both quantities increase markedly after cuff release but have returned to baseline levels after approximately 10 minutes.

FIG. 3 shows typical single pulse waveforms obtained by measuring pressure changes in the cuff In an artery with intact endothelial function, both pulse height (maximal cross-sectional arterial area) and compliance (maximum slope of the rising edge) increase markedly over baseline. When NO synthase is blocked via the inhibitor L-NAME, both pulse height and slope increases are greatly attenuated. FIG. 4 illustrates how a five minute cuff occlusion and the ensuring reactive hyperemia lead to major increases in area change per pulse and the maximum derivative of the area per pulse. Both metrics return to baseline levels after 20 minutes. FIG. 5 confirms the repeatability of the protocol by illustrating the effects of a series of two cuff occlusion periods. We see from FIG. 6 that only a small slow drift in the measured quantities occurs when no reactive hyperemic stimulus is applied.

Two Cuff Method

In certain embodiments, it may be preferred to obtain endothelial function measurements in segments of arteries that are not subject to ischemia during cuff occlusion. To allow such studies to be performed, two cuffs, or a single cuff that is segmented into two bladders may be used. The proximal cuff is used for measurement and is inflated to a pressure that does not fully occlude the vessel. The distal bladder is inflated to suprasystolic pressure during the stimulus interval in order to create downstream ischemia.

In another embodiment, two cuffs are used on the same limb and inflated to some substantially constant pressure. Pressure pulses resulting from cardiac activity (cardiac cycles) are detected in each cuff. The metric of vasorelaxation used is the transit time of the pulse between the two cuffs. When the vessel is dilated, the transit time decreases. Again the transit time measurement can be initially made to establish a baseline value. The subject can be administered a stimulus, and the transit time determined again to determine a stimulus-effected transit time.

An illustrative, but non-limiting, protocol can involve the following steps:

1. The subject is seated or lies supine and rests briefly, e.g., for five minutes.
2. The subject's blood pressure is measured.
3. Both cuffs are inflated to at or, preferably somewhat below, the diastolic pressure (e.g., 10 mm Hg below the diastolic blood pressure) and the pressure signal in each cuff is record to calculate a baseline transit time for a pressure pulse from the medial cuff to the distal cuff.
4. A stimulus is applied to the subject.
5. A pressure signal is recorded with both cuffs inflated to at or, preferably somewhat below, the diastolic pressure (e.g., 10 mm Hg below the diastolic blood pressure) and the pressure signal in each cuff is record a stimulus-effected transit time for a pressure pulse from the medial cuff to the distal cuff.
6. The stimulus-effected value of the transit time is compared to the baseline value of the transit time to determine presence, absence, and/or degree of endothelial response to said stimulus.

In various embodiments the systems and methods described herein are suitable for ambulatory use. Inflation of the cuff, for example, can be performed using a battery powered pump, or using replaceable/refillable gas cartridges. The subject can be alerted before a scheduled measurement commences and instructed to remain still and sit or lie down.

The foregoing protocols are intended to be illustrative and not limiting. For example, while the foregoing methods are described with respect to measurement of pressure pulses in the cuff resulting from cardiac activity in the subject, they need not be sol limited. Thus, in certain embodiments, the methods involve recording artificially induced arterial pressure pulses. Methods of artificially inducing arterial pressure pulses are known to those of skill in the art. For example, Maltz and Budinger (2005) *Physiol. Meas.* 26: 293-307 describe the use a linear actuator to induce an artificial arterial pressure pulse (see also U.S. Pat. No: 8,666,472). The actuator described herein employed a linear motor (from Baldor Electric Co., Fort Smith, Ark.), the actuating stem of which was adapted to make contact with the skin to introduce an artificial pulse. An applanation tonometer (SPT301, Millar Instruments, Inc., Houston, Tex.) at the free end of the stem sensed the applied force and allowed for closed-loop control of the force waveform.

In another embodiment, a cuff attached to a high bandwidth electropneumatic converter can be used to induce an artificial arterial pressure pulse. One illustrative electropneumatic converter is described by Tanaka et al. (2003) *Engineering in Medicine and Biology Society, Proceedings of the 25th Annual International Conference of the IEEE*, 4: 3149-3152. Tanaka et al. a disk-type cuff for local pressurization and a nozzle-flapper type electro-pneumatic converter (EPC) for the cuff-pressure control.

These embodiments are illustrative and not limiting. In view of the teachings provided herein, numerous methods to induce an artificial arterial pressure pulse are available to one of skill in the art. In certain embodiments even a standard cuff can be sufficient to induce a suitable pressure disturbance.

The systems described herein can be applied to arteries in the upper arms (or forelegs), forearms, the wrist, the thighs (hind legs), calves, ankles, and possibly even the neck (carotid arteries). In certain embodiments during the protocol, a second cuff may be applied to the contralateral limb (to which no endothelial stimulus is applied, or to which some other stimulus is applied) to serve as reference or to obtain differential measurements that elucidate the relative contributions of various vascular response mechanisms mediated by different biochemical pathways.

In various embodiments the system can be used to evaluate the effects of other stimuli including, but not limited to the influence of smooth muscle relaxation agents such as nitroglycerin, the influence of mental or physical stress, low intensity ultrasound $\beta_2$-adrenergic agonists such as albuterol, acoustic/mechanical tissue vibration, and the like. In various embodiments the cuff pressure may be set at different levels (during the measurement phase) to achieve different degrees of mechanical unloading. This can help to reduce the number of assumptions required for the interpretation of dA/dt as a measure of dA/dP. A ramping of the cuff pressure can also help to characterize the vessel more thoroughly. In various embodiments to improve signal quality, the cuff may be filled with a liquid or a gel rather than a gas.

In one particular illustrative application, the device, systems, and methods described herein are well suited for evaluation of subjects diagnosed with or at risk for sickle cell disease. In this context it is noted that the methods are highly suited to children relative to ultrasound as they are not very motion sensitive and young children are often difficult subjects. There is severe disruption of endothelial response in sickle cell disease and monitoring this can aid disease management.

FIG. 1 which provides a schematic illustration of a system 100 for assessing endothelial function in accordance with an illustrative embodiment of the methods and devices described herein. The system comprises a measurement cuff (e.g., blood pressure cuff) 112 that is configured for attachment to (around) a limb of a mammal (e.g., an arm, wrist, a leg, an ankle, etc.). The cuff can be fastened by any convenient method including, but not limited to a strap, a clip, a Velcro closure and the like. The cuff is used to administer a substantially constant pressure to the limb.

One or more bladders comprising the cuff are connected to a constant pressure source 103 that applies the constant pressure to the cuff. The pressure in the cuff in this case is purely determined by the external pressure applied by the air in the cuff. The pressure source can be coupled to a pressure controller 105 that regulates a valve or other actuator on the pressure source to regulate the substantially constant pressure applied to the cuff.

A pressure transducer (pressure sensor) 102 is disposed to monitor the pressure in the cuff. The output signal of the pressure sensor is read by a control unit 111 that comprises the circuitry necessary to read and, if necessary, to drive, the pressure sensor. In one illustrative embodiment, the control unit 111 comprises an amplifier 107 (e.g., instrumentation amplifier AD627, Analog Devices, Inc., Norwood Mass.) that amplifies the output signal of the pressure transducer, an optional low pass filter 108 (e.g., 8th Order elliptic Filter, LTC-1069-6, Linear Technology Corp., Milpitas, Calif.) and a digitizer 109 (e.g., an A/D converter PCI card (NI-6035, National Instruments, Austin, Tex.). Another tested embodiment employed a 0.6×0.6 in$^2$ MEMS pressure sensor (NPC-1210, GE Novasensor, Fremont, Calif.). The control unit 111 is configured to read the pressure from the pressure transducer.

In various embodiments the control unit 111 can be coupled to the pressure controller (e.g., via a signal cable) and thereby regulate the pressure applied to the cuff. As indicated by the dashed lines, in various embodiments, the controller 111 and pressure controller 105 can be integrated into a single control unit that both regulates the constant pressure source and reads the pressure fluctuations resulting from cardiac activity. In other embodiments, the controller 111 and pressure controller 105 can be separate units that communication (e.g., via a signal cable) or that, in certain embodiments, are independently controlled.

In certain embodiments the controller 111 as illustrated in FIG. 1, further comprises a microprocessor 110 (e.g., for signal processing and/or operating the pressure controller). The microprocessor 110 however need not be integrated into the controller, but may be a "separate" computer e.g., as described below. In certain embodiments the controller comprises a microprocessor that is itself connected to an external processor/computer. Thus, in some embodiments, the control unit may be connected to a computer via a cable for configuration and/or data download and/or for communication with an external computer, and/or for operation of the system.

Figure 7:
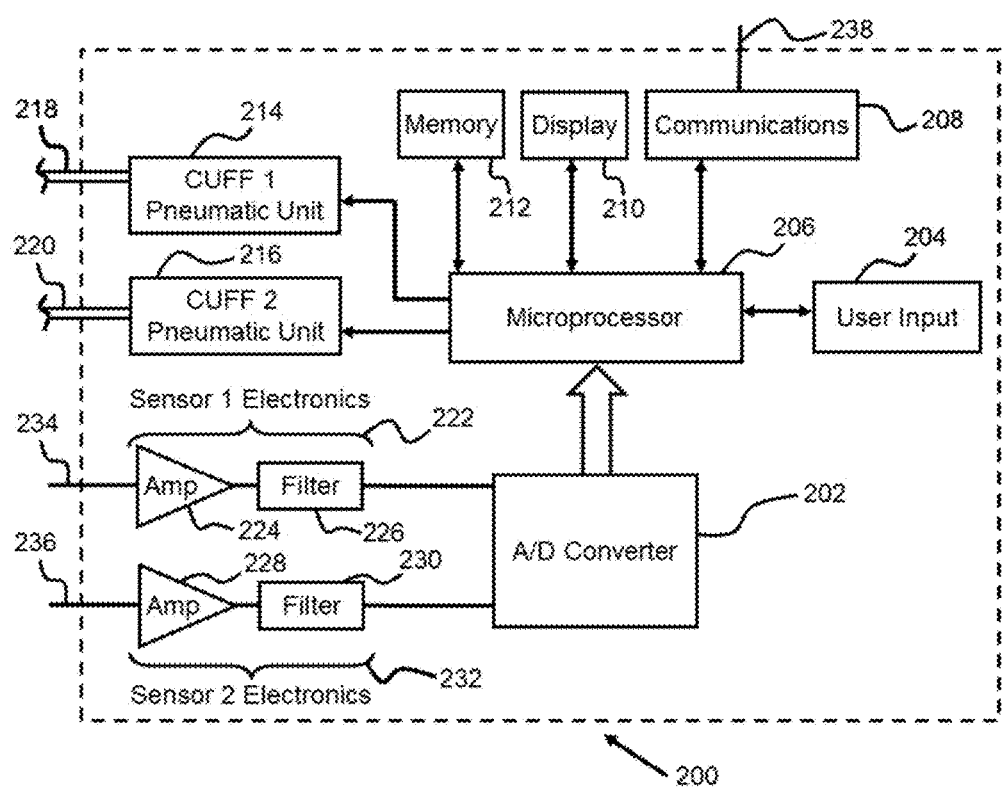
FIG. 7 provides a block diagram of a control 200 (111) in accordance with one illustrative embodiment of the present invention.

FIG. 7 provides a block diagram of a control 200 in accordance with one illustrative embodiment of the present invention. A microprocessor 206 optionally serves a central control and integration function controlling the various units/components therein. As illustrated in FIG. 7, the control unit includes, or is coupled to a pneumatic or hydraulic unit 214 (e.g., a unit comprising a pressure source 103 and/or a pressure controller 105) that operates to establish a substantially constant pressure in a cuff (cuff 1) via a hydraulic or pneumatic line 218. In certain embodiments, particularly where a pressure pulse transit time is to be determined, the control unit optionally includes, or is optionally coupled to a second pneumatic or hydraulic unit 216 (e.g., a unit comprising a pressure source 103 and/or a pressure controller 105) that operates to establish a substantially constant pressure in a second cuff (cuff 2) via a hydraulic or pneumatic line 218. It will be appreciated that the pneumatic or hydraulic control units can be used generally to inflate and/or deflate the cuffs as well.

Sensor electronics 222 are provided to send commands to sensor transducer and/or to read a signal from the pressure transducer monitoring pressure in the first cuff (cuff 1). Thus, in certain embodiments, a signal from a first pressure transducer in cuff 1 is transmitted along line 234 to sensor electronics 222, comprising for example, an amplifier 224, and/or a filter or signal conditioner 226 and/or any other electronics useful to drive, read, or transform the pressure transducer signal. An analogue to digital converter (A/D) 202 optionally converts the readings of the pressure transducer from cuff 1 and/or sensor electronics 222 into digital samples provided to microprocessor 206.

Where a second cuff is to be monitored, the control unit optionally further comprises sensor electronics 230 to send commands to sensor transducer and/or to read a signal from the pressure transducer monitoring pressure in a second cuff (cuff 2). Thus, in certain embodiments, a signal from a second pressure transducer in cuff 2 is transmitted along line 236 to sensor 1 electronics 232, comprising for example, an amplifier 228, and/or a filter or signal conditioner 230 and/or any other electronics useful to drive, read, or transform the pressure transducer signal. An analogue to digital converter (A/D) 202 optionally converts the readings of the pressure transducer from cuff 2 and/or sensor electronics 2232 into digital samples provided to microprocessor 206.

In illustrative embodiments, the pressure transducers comprise a sensor such as the Millar catheter pressure sensor (Mikro-tip, Millar Instruments, Houston, Tex.) or MEMS pressure sensor such as the NPC-1210 (GE Novasensor, Fremont, Calif.), but most low cost sensors used in automatic sphygmomanometers constitute suitable transducers.

Microprocessor 206 optionally also communicates with display 210, user input interface 204, and dynamic memory or static memory storage media 212 (e.g., disk drive, flash memory, optical memory, etc.). In some embodiments one or more communications lines 208 are used to communicate with an external computer or any other external unit. Power can be provided to the unit by an internal or external power supply that receives external power through a cable and/or through batteries.

In certain embodiments, the control unit 111/200 can be connected to a computer via Bluetooth, via a cable, and the like for configuration, control, and/or data download. In certain embodiments, the computer is integrated into the control unit and microprocessor 206 can function as the central processing unit of the computer, or another microprocessor is optionally present for such function. The computer can, for example, be dedicated for use with system 200, a personal computer in a physician's clinic, part of a hospital network and/or a remote computer connected, for example, through the internet, an intranet, or via a cell phone link. In certain embodiments, for example, a computer network connection can be used for may be used for receiving patient data and/or providing test results to remote locations. In some embodiments the computer manages a database of test results classified according to demographic and/or epidemiologic data for the purpose of determining endothelial dysfunction trends and/or for comparing current test results to previously acquired results from same or different patients. In some embodiments, the computer connects with a patient medical record system such as is maintained by a hospital, physician's office, HMO, PPO, and the like.

Figure 8:
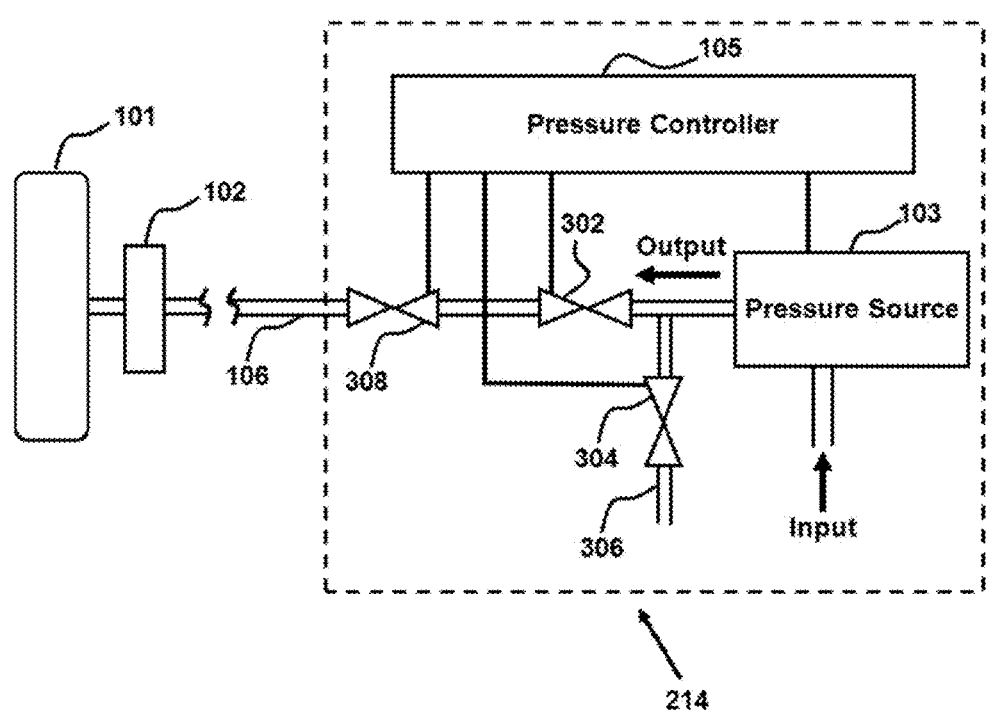
FIG. 8 provides a schematic view of one embodiment of a pneumatic/hydraulic unit 214 shown in FIG. 7.

FIG. 8 provides a schematic view of one embodiment of a pneumatic/hydraulic unit 214 shown in FIG. 7. Pneumatic unit 214 includes a pressure source 103 configured to provide output pressure up to a pressure that completely occludes blood flow through a limb or portion of a limb (or other region of a body). Typically pressures can be delivered that range up to about 200 mm Hg, up to about 250 mm Hg, up to about 300 mm Hg, up to about 350 mm Hg, up to about 380 mm Hg, or up to about 400 mm Hg or greater. Valve 302 optionally controls flow of a pressurized gas (e.g., air or other pressurized gas or gas mixture), or a pressurized fluid or gel from pressure source 103 to cuff 100. A valve 302 is optionally shut off after a desired substantially constant pressure is applied to the cuff. Another valve 304 is optionally provided to vent the cuff through outlet port/waste line 306 to reduce pressure or deflate the cuff.

An optional valve 308 can be provided to restrict flow to the cuff and thereby slow the response time of the pneumatic/hydraulic unit so that pressure regulation does not substantially attenuate pulses produced in the cuff by cardiac activity. A pressure line 106 carries the gas, fluid, or gel to the cuff whereby the cuff is inflated or deflated. In certain embodiments the pressure line 106 is a narrow line that constricts flow thereby reducing the response time of the pneumatic/hydraulic unit. A pressure controller 105 is optionally incorporated into the pneumatic/hydraulic unit to regulate flow into and out of the pressure source and/or to regulate valves 306 and/or 304, and/or 302.

Any of the foregoing systems and devices can further include units to induce an artificial arterial pressure pulse. Such units include, but are not limited to a linear actuator, as described above (see, e.g., Maltz and Budinger supra.), a disk-type and a nozzle-flapper type electro-pneumatic converter (EPC) for the cuff-pressure control (see, e.g., Tanaka et al. supra), a standard cuff, and the like.

Figure 9:
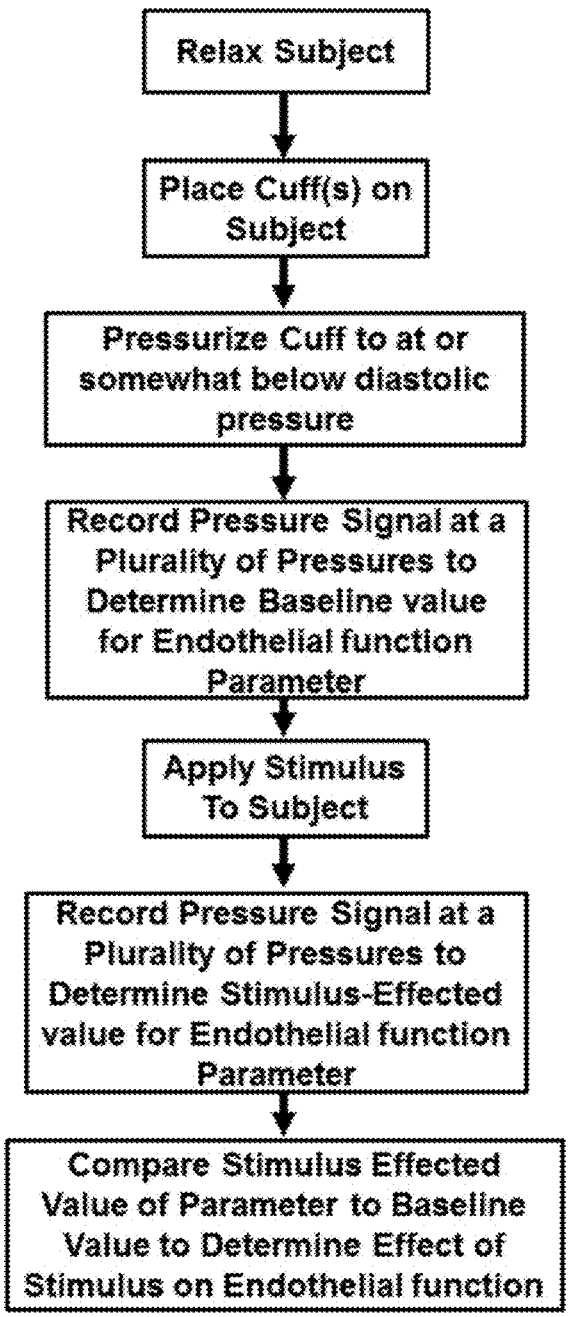
FIG. 9 provides flow chart illustrating typical acts performed in a measurement of the effect of a stimulus on endothelial function.

FIG. 9 provides flow chart illustrating typical acts performed in a measurement of the effect of a stimulus on endothelial function. The subject is typically allowed to rest (e.g., for at least 1 minute, at least 2 minutes, at least 3 minutes, at least 4 minutes, at least 5 minutes, at least 10 minutes, at least 15 minutes, etc.) to avoid the effect of transient activity of other stimulation on the measurement. The subject may be required to avoid eating, taking medicine, smoking and/or drinking coffee for certain periods of time (e.g., two hours or more before the test). The cuff or cuffs (e.g., depending on whether a transit time calculation is to be made) are affixed to the desired regions(s) of the subject (e.g., arm, leg, wrist, ankle, etc.). The blood pressure of the subject is optionally determined using any method known in the art and/or using the system itself. The cuff(s) are then inflated to a substantially continuous pressure at or below the measured diastolic pressure of the subject. Thus, in certain embodiment the cuffs are inflated to a pressure below the measured (or mean or median measured) diastolic pressure (e.g., not less than about 10 mm Hg below the diastolic pressure, or not less than about 15 mm Hg below the diastolic pressure, or not less than about 20 mm Hg below the diastolic pressure, or not less than about 25 mm Hg below the diastolic pressure, or not less than about 30 mm Hg below the diastolic pressure). A pressure pulse or series of pressure pulses resulting from one or more cardiac cycles is then recorded providing baseline pressure versus time data. The data is optionally processed to provide one or more parameters (e.g., maximum expansion, integrated pressure/time, maximum slope of pressure pulse, transit time of pulse from one cuff to a second cuff, etc.).

A stimulus is then applied to the subject. Any of a number of stimuli expected to alter endothelial function are contemplated. Such stimuli include, for example, occlusion of blood flow, and/or application of one or more drugs to the subject. Illustrative drugs include, for example, drugs that act as NO agonists (e.g. acetylcholine), β-adrenergic agonists such as albuterol, acoustic/mechanical tissue vibration, transcutaneous low frequency ultrasound (see, e.g., Iida et al. (2006)J. Amer. Coll. Cardiol., 48(3): 532-537), and the like. The contribution of basal NO release to basal vascular tone may be elicited by administering NO-synthase inhibitors such as L-NMMA and L-NAME. These agents may be administered via intra-arterial infusion (as is conventional practice) or by means of novel administration methods we have demonstrated involving nasal inhalation and ingestion. Endothelium-independent smooth muscle function may be evaluated by administration of NO-releasing drugs such as nitroglycerin and sodium nitroprusside.

In certain embodiments, the stimulus excludes occlusion and/or application of drugs. In certain embodiments the stimulus excludes occlusion and/or application of drugs that are NO agonists.

In certain embodiments the stimulus comprises acoustic/mechanical tissue vibration, or transcutaneous low frequency ultrasound.

A pressure pulse or a series of pressure pulses resulting from one or more cardiac cycles is then recorded providing stimulus-effected pressure versus time data. The data is again optionally processed to provide one or more parameters (e.g., maximum expansion, integrated pressure/time, maximum slope of pressure pulse, transit time of pulse from one cuff to a second cuff, etc.).

The baseline data or derived parameters is then compared to the stimulus-effected data or derived parameters to determine the presence, absence, and/or magnitude of the effect of the stimulus. In certain embodiments the results may be recorded in a database (e.g., in a medical record).

In certain embodiments the blood pressure can be eliminated and the cuffs simply inflated to a predetermined or arbitrary substantially constant pressure.

In certain embodiments when using occlusion as a stimulus, Alternatively to occluding the same artery on which the measurements are performed, a different artery connected to the measured artery, is occluded. For example, when the measurements are performed on the brachial artery, the occlusion may be applied to the radial and/or ulnar arteries. Ideally, when such a cuff is used to assess endothelial function, the occluding cuff is placed downstream of the points of measurement. This increases the contribution of NO-dependent mechanisms to the vasodilation that occurs, and minimizes the effects of tissue ischemia (which, are substantially mediated by other biochemical pathways not dependent on NO). The two cuffs may be integrated into a single entity containing two fillable air cavities. The upstream cavity is inflated only during the measurement intervals (to subdiastolic pressures), while the downstream cavity is used only for inducing endothelial stimulus via reactive hyperemia (inflated to suprasystolic pressures). In this way, the measurement is always obtained in an arterial segment that was not subject to ischemia.

The baseline phase measurement(s) optionally includes a plurality of rounds (e.g., 2-5 rounds), in each of which the pressure versus time data are recorded. The results of the plurality of measurement rounds can be optionally averaged to, in principle, reduce noise in the measurements. In addition to, or as an alternative, other noise reducing statistical methods can be utilized. Alternatively, in certain embodiments a single measurement is performed in order to limit the time required for the measurement session. Several of the earliest baseline measurement rounds may be discarded according to a predetermined protocol in order to minimize any initial deformation of the limb cross section that may occur during the first measurements.

In certain embodiments the stimulus-effected measurements are made a predetermined time after application of the stimulus, e.g., when the stimulus effect is expected to be maximal.

In various embodiments repeated measurement rounds can be made after periods of reduced or eliminated cuff pressure to prevent the repeated measurement rounds from inducing hyperemia which would influence the measurements and/or prevents the repeated measurement rounds from causing discomfort to the patient.

As indicated above, in certain embodiments a score or derived parameter representative of endothelial function is determined based on the effect (or absence of effect) of the stimulus (depending on the stimulus used). In certain embodiments the score is compared to a threshold and accordingly a binary diagnosis is provided (e.g., normal, abnormal). In some embodiments, the threshold depends on one or more attributes of the patient, such as gender, height, weight and/or age. Alternatively or additionally, a multi-level diagnosis is provided, for example giving a value in percentages or other units. The multi-level diagnosis is optionally determined by comparing the score to an array of thresholds or to a "standard" curve.

As mentioned above, during the test session, between the base line phase and the stimulus affected measurement, the subject preferably remains at rest, so as to minimize the difference in conditions between the measurements. Alternatively or additionally, the results are corrected for changes in the conditions between the phases.

As indicated above, in some embodiments, the difference in the baseline and stimulus effected parameters is calculated by determining an envelope of the measurements and finding a maximum value with the envelope to use as the basis of the parameter calculation. In certain embodiments the maximal difference in the value of the parameter(s) between the baseline and stimulus-effected parameters is determined. The calculation is performed using any method known in the art, such as using a fitting method which finds a maximal difference over a single cardiac cycle, or over a plurality of cardiac cycles (e.g., 2, 3, 4, 5, 6, 7, 8, 9, 10, 11, 12, 13, 14, 15, 20, 25, 30, or more cardiac cycles).

As mentioned above, the systems described herein can be used to determine the blood pressure of the subject patient, during endothelial function tests or separately. Typically, such measurements can be made by inflating the cuff to a pressure above the systolic pressure of the subject and the air pressure of the cuff is deflated to below the diastolic blood pressure of the patient. During the air pressure deflation, pressure transducer 102 registers the changes in the pressure of measurement cuff 100. The resulting data are then analyzed to find the systole (SYS), and/or diastole (DIA) pressures, using any of the methods known in the art for oscillatory blood pressure measurement.

It is noted that a poor dilatation functioning may occur due to arteriosclerosis of a specific artery. In order to prevent identification of endothelial dysfunction in subjects that have local arteriosclerosis in a single artery but do not suffer from endothelial dysfunction, in some embodiments the methods described herein are repeated on another artery of the subject, for example on the opposite arm. If dysfunction identified for one artery but not the other, the subject is identified as not having endothelial dysfunction and/or is sent for additional tests.

In some embodiments, the microprocessor 206 and/or separate computer is programmed to carry out a complete test session automatically without requiring instructions from a human operator. Optionally, control unit 200 checks that the conditions are proper and stops the test session if a problem is detected, for example when signal is detected, when pressure exceeds a threshold, or when no sensible data is produced perhaps due to erratic or significant oscillations in the blood pressure of the subject during the test.

Alternatively, the operation sequence of a test session may be partially or entirely human operated. For example, each measurement phase may be controlled automatically by microprocessor 206, while the initiation of each phase is controlled by a human operator. Optionally, an operator may program operation sequences through a computer or other device. Alternatively or additionally, required operation sequences are preprogrammed into microprocessor 206 at the time of manufacture.

Practical Low Cost Systems.

In certain embodiments the prototype illustrated in FIG. 1 may use an expensive and bulky pneumatic regulator to produce constant pressure in the cuff during measurement. In contrast, one illustrative and less expensive portable prototype is shown in the schematic diagram of FIG. 12, and photographs of FIG. 13. This illustrative, but non-limiting embodiment uses a miniature pump and solenoid valve to control cuff pressure. Since the pump and solenoid valve provide on-off control, the pressure in the cuff generally falls with time as the tissue under the cuff displaces. There are a number of compelling reasons to use on-off control: 1) There is no need for an expensive pressure regulator and compressed air source; 2) The pump preferably does not operate during measurement as it introduces noise into the signal; 3) The component count is smaller and the cost is much lower; and 4) Standard pumps and valves employed in home blood pressure measurement systems can be used. Since the pump and valve may be actuated during a measurement interval, the recorded signal may be contaminated with noise. For offline processing applications, this can be removed using low-pass filtering of the recorded time-series. For online processing, the times of actuation can be fed into a data analysis algorithm to ensure this noise does not confound the analysis.

Data Analysis for On-off Systems.

Figure 15:
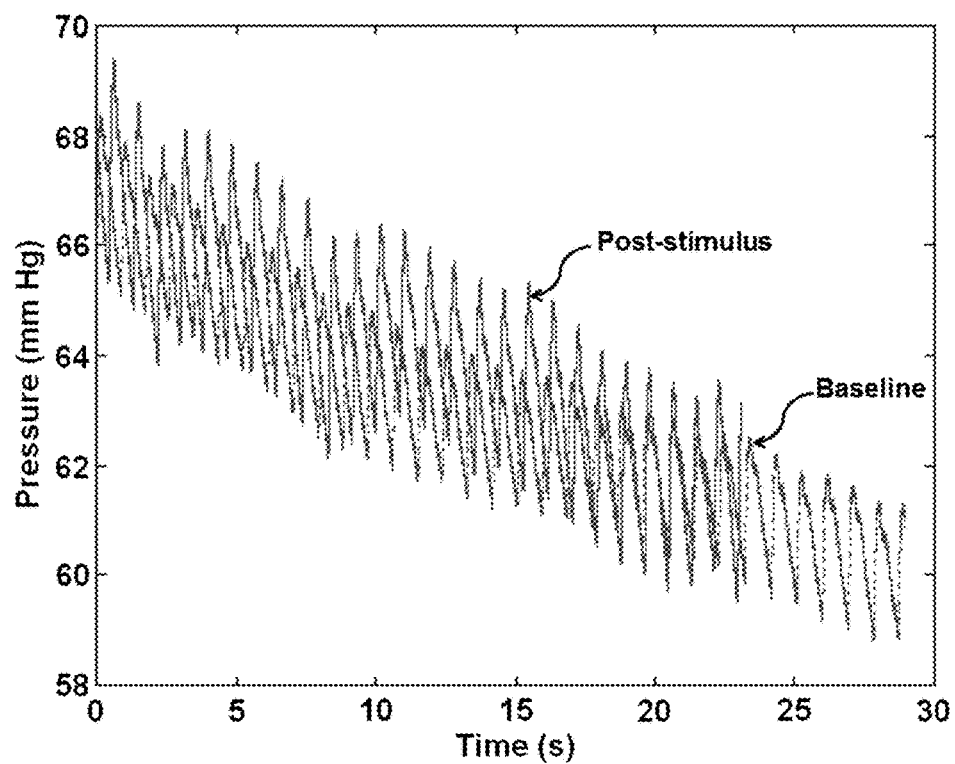
FIG. 15 shows the typical decrease in cuff pressure during the measurement interval owing to the displacement of tissue under the cuff. The analysis method preferably takes this characteristic into account.
Figure 16:
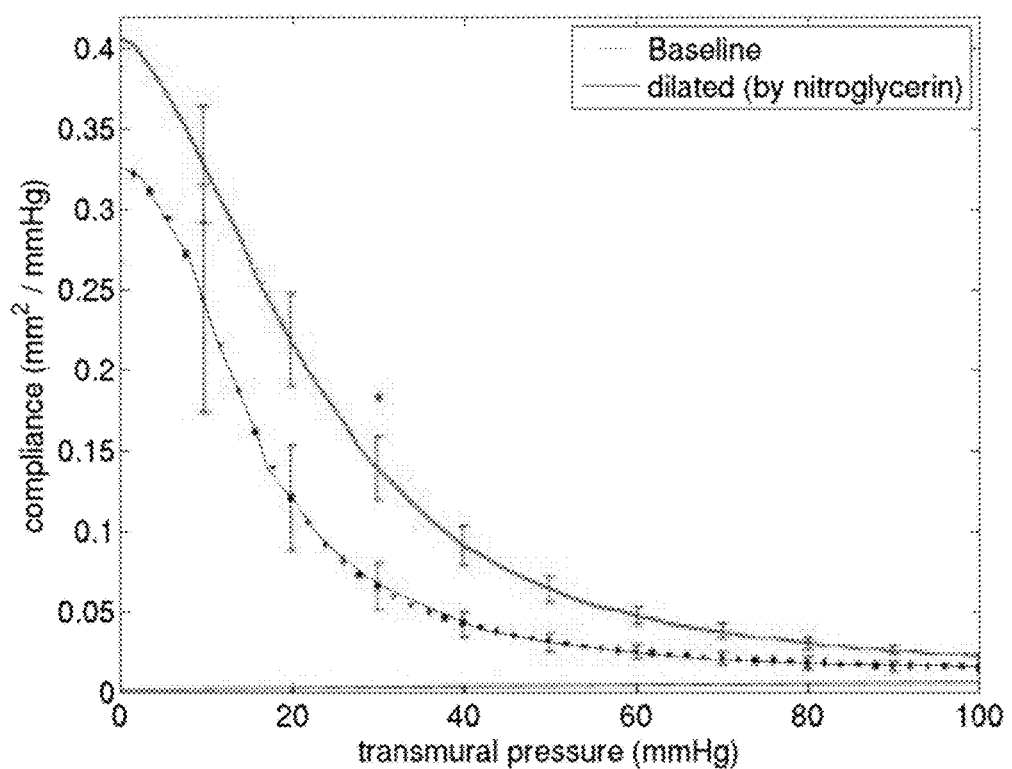
FIG. 16 illustrates the change in arterial compliance with transmural pressure (blood pressure minus cuff pressure). These data were obtained using intraarterial ultrasound and blood pressure measurement.

To address this issue, a method of data analysis was developed that improves the accuracy of a system with on-off control to the extent that impressive results such as those shown in Table 2 are possible. Consider FIG. 15, which demonstrates the typical fall in pressure during a measurement interval. The curves in FIG. 16 illustrate the effect of article unloading on arterial compliance (Bank et al. (1999) *Circulation,* 100: 41-47). A decrease in unloading pressure of 8 mm Hg (as seen in FIG. 15) can impact compliance significantly when the transmural pressure is small (10-20 mm Hg in our case at diastole). Clearly, when comparing pulse properties such as amplitude and maximum upward slope, before and after stimulus, it is preferably to compare pulses measured at like cuff pressures. For example, in FIG. 15, while it is appropriate to directly compare the post-stimulus and baseline at t=20 s, this is not the case at t=10 s. In the former case, the cuff measurement pressure is similar, but in the latter case, it is larger during the post-stimulus series than during the baseline series.

One illustrative approach to this issue is to "histogram" the pulses by pressure, using a binning statistic such as the mean, median, minimum or maximum pressure during the pulse. Pulses in each histogram bin from the baseline and response series are compared and the fractional change is computed for each bin. A weighted average of the bins is taken, where the weights are proportional to the number of pulses in each bin and the confidence in each measurement.

In cases where the ranges of pressure do not completely overlap, curves such as those shown in FIG. 16 can be used to adjust the data so all pulses can be compared.

Another method by which one may perform the analysis is to apply regression on the pressure characteristic during the measurement period. The regression curve is then used to scale the individual pulses to a certain reference pressure. Pulses obtained at different pressure values can be compared as if these were all obtained at the reference pressure.

Increasing Measurement Pressure Stability.

As described above, regression analysis can be applied to address the problem of mean measurement pressure variation following initial attainment of a pressure set point. Two additional schemes are proposed to address this issue without requiring a pneumatic feedback system such as a pressure regulator.

Figure 17:
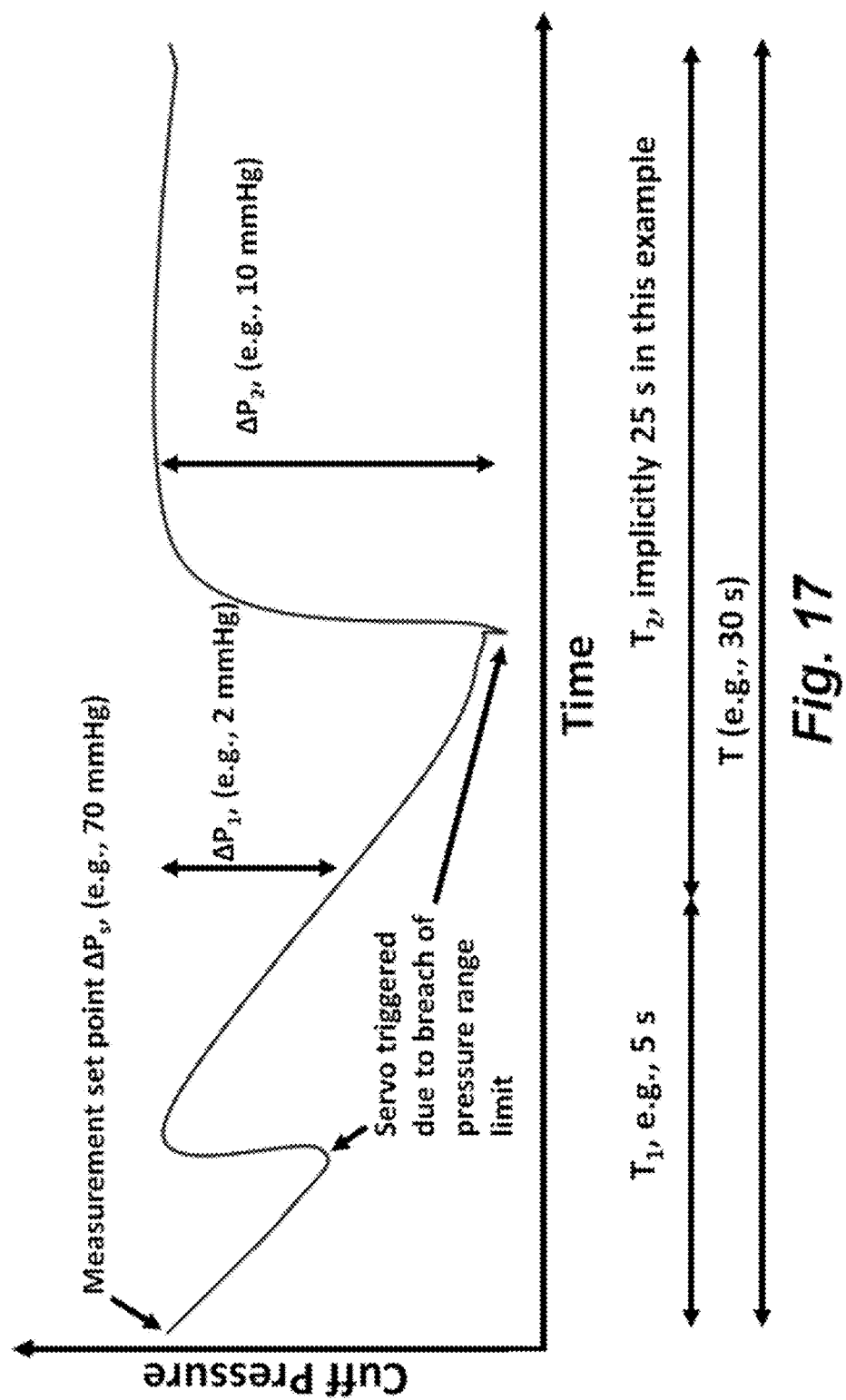
FIG. 17 illustrates various approaches to improve consistency of mean measurement pressure by addressing variations in pressure due to compression and conformation of the tissue under the cuff. The measurement interval is divided into two segments. Each is assigned a different servo range, or a different servo mechanism is employed during each.
Figure 18:
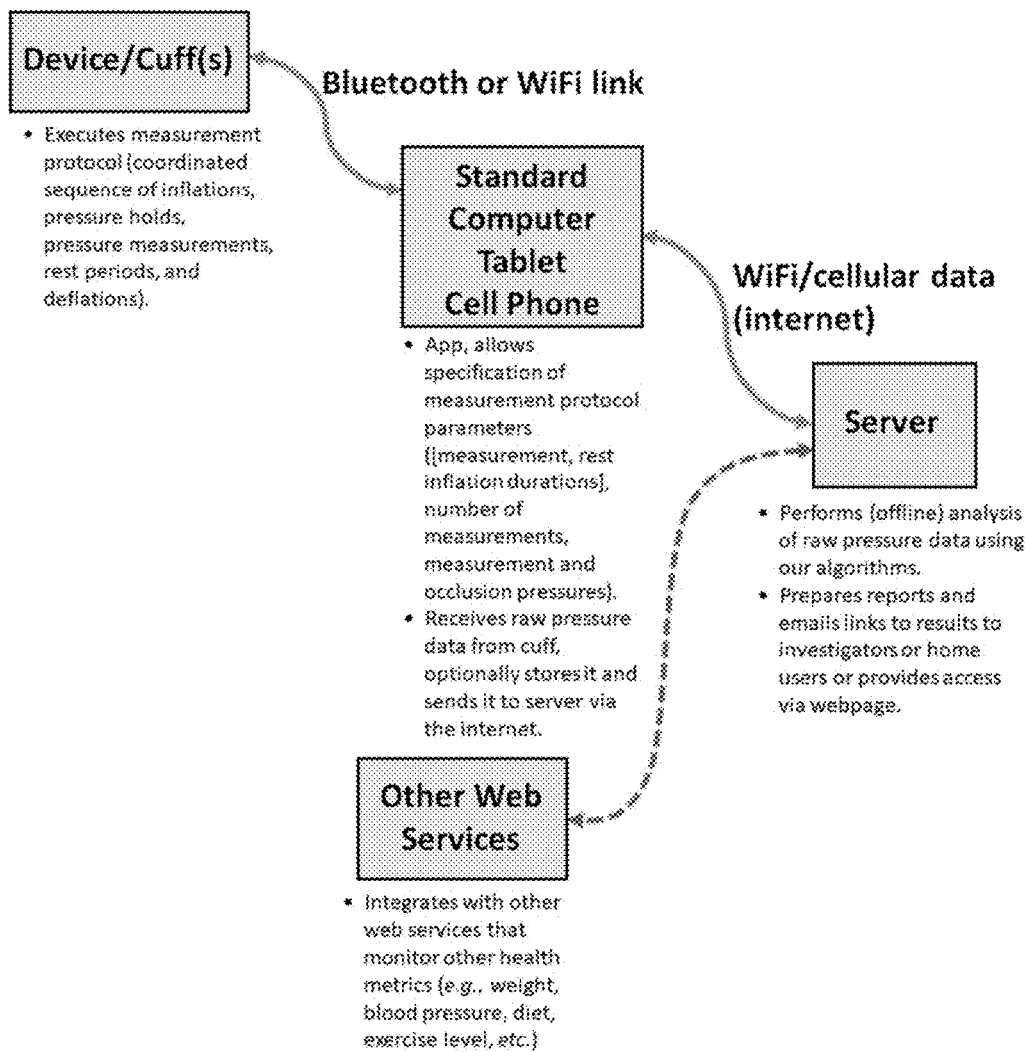
FIG. 18 illustrates components of a home health monitoring system incorporating methods and/or devices described herein.

As is illustrated in FIG. 17, divide each of the measurement intervals T can be divided into two segments, $T_1$ and $T_2$, such that $T=T_1+T_2$. The purpose of $T_1$ is to stabilize the pressure close to the measurement pressure set point during the period where tissue compression under the cuff leads to a natural pressure drop. Once the pressure has stabilized, or otherwise, $T_2$ begins, during which no control of the pressure is exercised, or the criteria for initiating pressure corrections are considerably relaxed.

Figure 12:
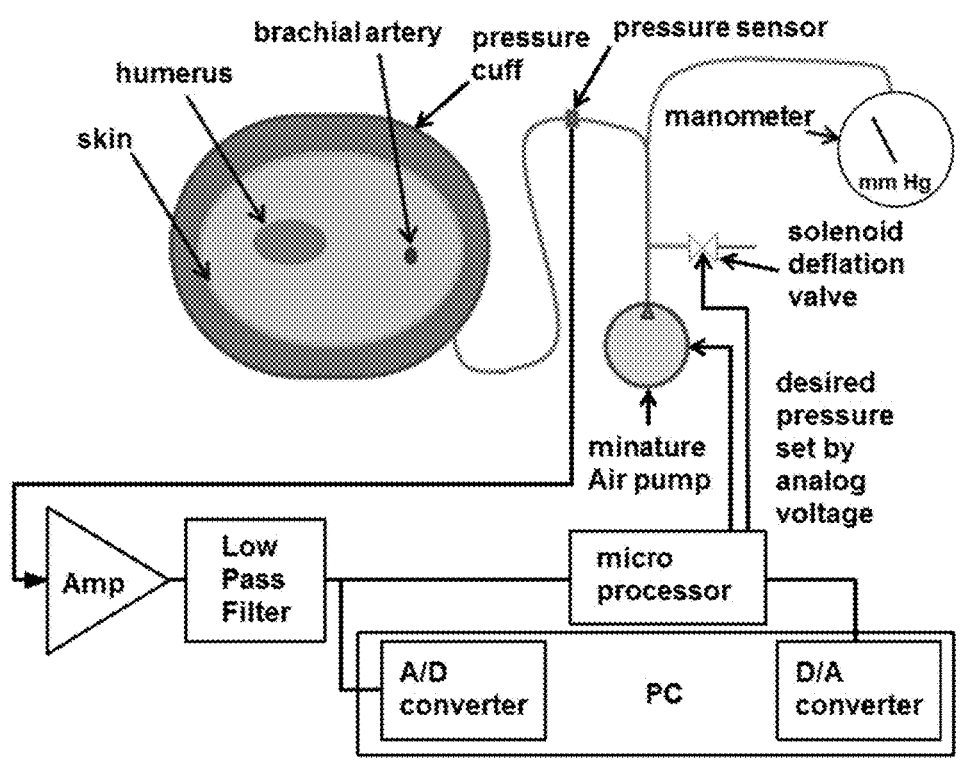
FIG. 12 illustrates one embodiment of a system that uses an on-off control system to set the cuff pressure to a constant value during measurement. This is effected by a microcontroller that actuates a pump (or other pressure source) and a valve.
Figure 14:
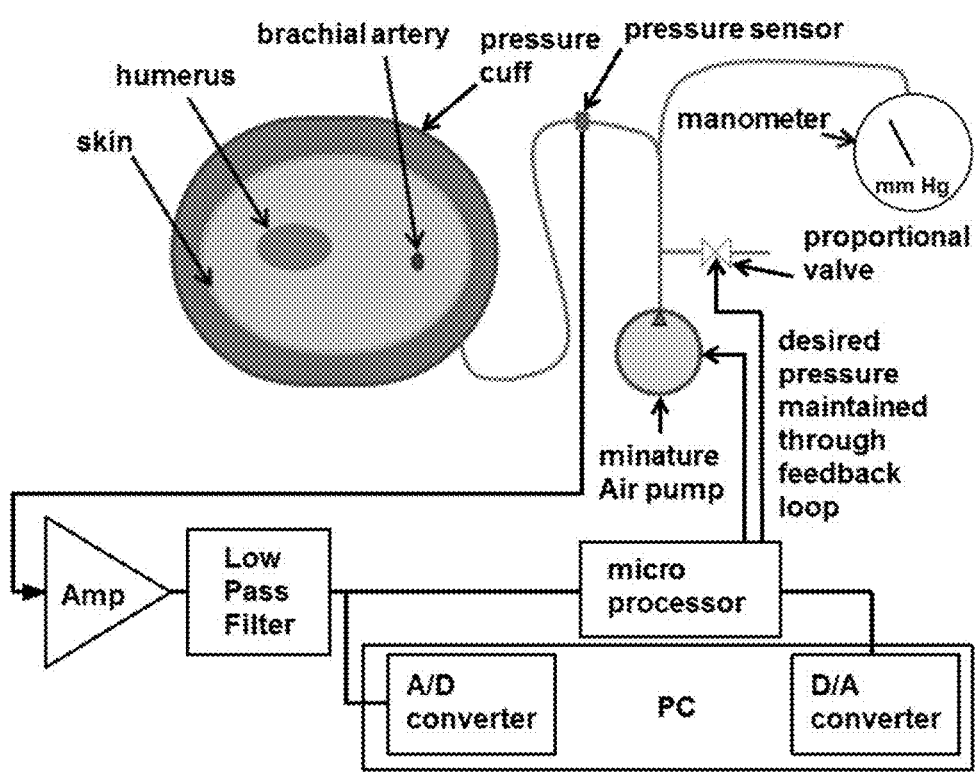
FIG. 14 illustrates one embodiment of a system that uses a variable control system to set the cuff pressure to a constant value certain periods of a measurement or pre-measurement phase. This is effected by a microcontroller that actuates a pump (or other pressure source) and a valve.

In one illustrative scheme, we substitute the solenoid on-off deflation valve in FIG. 12 with a proportional valve as illustrated in FIG. 14. A typical example of a miniature proportional valve is the VSO-MI (Parker Hannifin Corp., Cleveland Ohio). During $T_1$, the pump continues to run, while a control feedback system adjusts the proportional valve such that the desired pressure set point is maintained. An advantage of this scheme is that it is not necessary to adjust the pump output, which may not be feasible with many pump types. During $T_2$, either:

1) The pump is deactivated and the valve is shut fast; or
2) A typical on-off servo control regime is implemented.

The second scheme relies on assigning different pressure tolerances to $T_1$ and $T_2$, namely $\Delta P_1$ and $\Delta P_2$. During interval $T_n$, adjustment of the pressure is only initiated when the cuff pressure $P<P_s-\Delta P_n$ or $P>P_s+\Delta P_n$ wherein $P_s$ is the measurement pressure set point. Thus, for example, during interval $T_1$, the pressure tolerance ($P_t$) is $P_t=P_s\pm\Delta P_1$, while during interval $T_2$, the pressure tolerance is $P_t=P_s\pm\Delta P_2$. When the actual cuff pressure P goes above or below the range for $P_t$ the pressure is adjusted. By setting, for example, $\Delta P_2 > \Delta P_1$, it is possible to avoid unnecessary servoing during $T_2$ that may render measurement data unusable. FIG. 17 provides one illustrative, but non-limiting example of these ranges, and the interpretation of these quantities.

Apparatus to provide uFMD measurements.

In various embodiments an apparatus for assessment of endothelial function in a mammal is proved where the apparatus can generate uFMD results. In certain embodiments the apparatus comprises a measurement cuff adapted to apply a substantially pressure to an artery in said mammal; a measurement unit adapted to detect and quantify over one or more cardiac cycles, pressure pulses in said cuff while said pressure is applied; a controller that is adapted to apply to the cuff a different pressures within a single time period (Tm), and/or to apply substantially constant pressures that differ in different time periods ($T_m$) where the controller monitors and adjusts the pressure in the cuff and whose response time is sufficient slow so that the changes in pressure resulting from said cardiac cycles are not substantially attenuated by said system, and/or that is adapted to control a pressure source and a valve to provide on-off control of the pressure in said cuff; and a processor adapted to determine a plurality of baseline values for a parameter related to endothelial function as a function of applied pressure ($P_m$) and to determine a plurality of stimulus-effected values for a parameter related to endothelial function as a function of applied pressure ($P_m$).

In certain embodiments the processor is adapted to determine the area of the arterial lumen calculated from the baseline pressure measurements as a function of transmural pressure $P_{tm}$, where transmural pressure is determined as the difference between the baseline measured pressures and the external cuff pressure $P_m$ and fitting these data with a first non-linear model to provide a first function describing baseline arterial lumen area as function of transmural pressure; to determine the area of the arterial lumen calculated from the stimulus-effected pressure measurements as a function of transmural pressure $P_{tm}$, where transmural pressure is determined as the difference between the measured stimulus-effected pressures and the external cuff pressure $P_m$ and fitting these data with a second non-linear model to provide a second function describing stimulus-effected arterial lumen area as function of transmural pressure; to use the first function to calculate baseline arterial lumen area ($A_b$) at a transmural pressure substantially equal to the systolic blood pressure; and to use the second function to calculate stimulus-effected arterial lumen area ($A_r$) at a transmural pressure substantially equal to the systolic blood pressure. In certain embodiments the processor is configured to determine the equivalent ultrasound-based FMD (uFMD) where uFMD is proportional to the square root of the ratio $A_r/A_b$. In certain embodiments the processor is configured to determine the equivalent ultrasound-based FMD is given as $$uFMD\% = [\sqrt{(A_r/A_b)} - 1] \times 100$$

In certain embodiments the first non-linear model and/or said second non-linear model are the same type of function. In certain embodiments the first non-linear model and/or said second non-linear model are selected from the group consisting of a 2 parameter model, a 3 parameter model, a four parameter model, a 5 parameter model, and a six parameter model. In certain embodiments the first non-linear model and said second non-linear model are both arctangent models.

In certain embodiments the processor is configured to determine the pressure in the cuff as a function of time to provide a cardiac pulse waveform while the cuff inflates and/or while said cuff deflates. In certain embodiments the processor is configured to compare cardiac pulse waveforms between baseline and post-stimulus conditions either by direct comparison of pulse characteristics at corresponding pressure levels or by first fitting models to the set of baseline cardiac pulse wave forms and to the set of post-stimulus cardiac pulse waveforms and comparing parameters generated by the two models.

In certain embodiments the apparatus is configured to measure blood pressure and cFMD simultaneously. In certain embodiments the apparatus is configured to measure the systolic BP and MAP and to calculate the diastolic blood pressure (DBP) using an oscillometric analysis; and/or the apparatus is configured to measure the systolic BP and MAP are measured and to determine the DBP by analyzing Korotkoff sounds obtained using an audio sensor (e.g., stethoscope, phonocadiogram) or ultrasound probe. In certain embodiments the apparatus is configured to calculate cFMD and/or MAP, and/or DBP from measurements obtained during cuff inflation; and/or the apparatus is configured to calculate cFMD and/or MAP, and/or DBP from measurements obtained during cuff deflation. In certain embodiments the apparatus is configured to determine systolic BP and/or diastolic BP and, for cFMD determination, to provide a comparison of pulse waveform characteristics between baseline and post-stimulus intervals at transmural pressures calculated using the determined systolic and/or diastolic BP values.

In certain embodiments the apparatus is configured to perform the method for determining uFMD as described herein, except application of the stimulus.

In certain embodiments the apparatus is configured to perform the method for determining uFMD as described herein, including application of the stimulus where the stimulus comprises restricting flow of blood to the limb by occlusion of a blood vessel. In certain embodiments the apparatus is configured to restricting the flow of blood using a cuff. In certain embodiments the apparatus is configured to restrict the flow of blood and applying the pressure on the artery are using separate cuffs. In certain embodiments the apparatus is configured to use the same cuff is used to occlude the blood vessel and to apply the pressure on the artery. In certain embodiments the apparatus is configured to inflate a restricting cuff to a pressure at least 10 mm Hg above measured systolic blood pressure for the mammal. In certain embodiments the apparatus is configured to restricting flow of blood through the artery for at least 1 minute.

In certain embodiments the controller is configured to apply pressure to the cuff during one or more time periods ($T_m$) by adjusting a pump or other pressure source and/or a proportional release valve to maintain a desired pressure. In certain embodiments the controller is configured to stop adjustment of said pressure during the time period(s). In certain embodiments the controller is configured to periodically adjust said pressure using an on-off control system during the time period(s). In certain embodiments the controller is configured to maintain pressure within a pressure range (AP) around a measurement set point during a time period. In certain embodiments the pressure range (AP) ranges from about 1 mm Hg to about 6 mm Hg, or from about 1 mm Hg to about 4 mm Hg, or from about 1 mm Hg to about 3 mm Hg, or from about 1 mm Hg to about 2 mm Hg. In certain embodiments the apparatus is configured to provide a time interval duration ranging from about 1 sec, or from about 2 sec, or from about 3 sec, or from about 4 sec, or from about 5 sec, or from about 6 sec, or from about 7 sec, or from about 8 sec, or from about 9 sec, or from about 10 sec, or from about 15 sec up to about 20 sec, or up to about 30 sec or up to about 40 sec or up to about 50 sec, or up to about 1 min, or up to about 2 min, or up to about 3 min, or up to about 4 min, or up to about 5 min, or up to about 6 min, or up to about 7 min, or up to about 8 min, or up to about 9 min, or up to about 10 min, or up to about 15 min, or up to about 20 min, or up to about 25 min, or up to about 30 min.

In various embodiments the controller is configured to monitor and adjust said pressure at a response time sufficiently slow so that said pressure changes resulting from said cardiac activity are attenuated by less than 10%. In certain embodiments the controller is configured to maintain the external pressure by setting the pressure in a cuff to a value and not altering external pressure applied to the cuff during the measurements of pressure variations due to said cardiac activity. In certain embodiments the controller is configured to apply an external pressure equivalent to or below a diastolic pressure determined for said subject. In certain embodiments the controller is configured to apply an external pressure below the average diastolic pressure measured for the subject or below an expected diastolic pressure for the subject. In certain embodiments the controller is configured to apply an external pressure below the average diastolic pressure measured for said mammal, but no less than about 10 mmHg below said average diastolic pressure. In certain embodiments the controller is configured to apply a constant pressure at different levels during different measurement intervals.

In various embodiments the apparatus comprises a hydraulic or pneumatic pump adapted to apply the pressure to one or more cuffs. In certain embodiments the response time is reduced by disposing a narrow pressure line between hydraulic or pneumatic pump and a cuff. In certain embodiments the apparatus comprises a valve and a pump configured to provide on-off control of the pressure in one or more cuffs. In certain embodiments the apparatus further comprises an accelerometer disposed to detect movement or vibrations in said cuff or apparatus.

In various embodiments the cuff is pressurized with a material selected from the group consisting of a gas, a fluid, and a gel. In various embodiments the cuff is adapted to apply pressure substantially around an entire circumference of a limb including the artery. In certain embodiments the cuff is adapted to apply a local pressure that does not substantially affect other blood vessels in a same limb as the artery.

In various embodiments the processor in the apparatus is configured to determine a blood pressure. In various embodiments the processor is configured to calculate the external pressure to be applied based on one or more blood pressure measurements and to direct the controller to apply the calculated external pressure. In certain embodiments the controller is configured to induce at least one of measurement round responsive to an indication that a stimulus was administered to the artery and at least one of the measurement rounds before the indication that the stimulus was administered to the artery is received.

In certain embodiments the controller is adapted to apply the pressure continuously over at least five cardiac cycles of the patient. In certain embodiments the controller is configured to store over the course of one or more cardiac cycles, changes in pressure in said cuff resulting from cardiac activity of the mammal as a function of time.

In certain embodiments the processor is configured to integrate the value of a pressure change over time (calculate the area under a pressure/time curve) for one or for a plurality of cardiac cycles to determine an integrated pressure value.

In certain embodiments the processor is configured to determine the maximum of the derivative of the pressure versus time wave form on the rising edge of a pressure pulse for one or for a plurality of cardiac cycles to determine a compliance value. In certain embodiments the processor is configured to average said integrated pressure value and/or said compliance value over a plurality of cardiac cycles. In certain embodiments the processor is configured to determine the integrated pressure value and/or the compliance value for a single cardiac cycle. In certain embodiments the processor is configured to determine said integrated pressure value and/or said compliance value and identify a maximum change in said value between a baseline measurement and a stimulus-effected measurement.

Subject Motion

From our human subject studies, it is apparent that oscillatory subject motion such leg shaking can introduce spurious waveforms that may be interpreted as pulses. This can be addressed by means of software and/or hardware. One software approach is to perform real-time analysis of the incoming pressure signal and detect anomalies. In a hardware approach, an accelerometer can be placed on the cuff, on the cuff tube or in the instrument itself to detect vibrations that cannot be easily filtered out (e.g., those that are in the same frequency band as the signal of interest). The system can then generate an alert to the user indicate that vibration is present and may abort the measurement if vibration does not cease.

It will be appreciated that the above described methods and apparatus may be varied in many ways, including, changing the order of acts of the methods, and the exact implementation used for the apparatus. It should also be appreciated that the above described methods and apparatus are to be interpreted as including apparatus for carrying out the methods and methods of using the apparatus.

The devices and methods have been described herein using non-limiting detailed descriptions of embodiments thereof that are provided by way of example and are not intended to limit the scope of the invention. For example, rather than performing the endothelial dysfunction test on the arm, the method may be performed on a subject's leg.

In addition, while the methods are described with reference to humans, the term mammal is intended to include humans as well as non-human mammals (e.g., non-human primates, canines, equines, felines, porcines, bovines, ungulates, largomorphs, and the like).

Home Health Monitoring.

In certain embodiments the methods and devices described herein are well suited to home health monitoring. In certain embodiments the devices described herein can be provided as off-the-shelf products comprising a 1-cuff or a 2-cuff system, and typically, although not necessarily a control system to operate the cuffs. The device is typically configured to executes one or more measurement protocol(s) (e.g., coordinated sequence of inflations, pressure holds, pressure measurements, rest periods and deflations).

In certain embodiments (e.g., as illustrated in FIG. 17 the system can link to a computer, a tablet, and/or a cell phone, e.g., via a direct cable, via a wireless (e.g., wifi) link, or via a Bluetooth). In certain embodiments the computer/tablet/cell phone runs an application (e.g., an app) that allows specification of, e.g., measurement protocol parameters ([measurement, rest, inflation durations], number of measurements, measurement and occlusion pressures, etc.). The computer/tablet/cell phone can receive raw pressure data or processed data from the cuff, optionally stores the data, and can send it to a server via the Internet.

The server (e.g., provided by a healthcare providing or health monitoring service) can performs (offline) analysis of raw pressure (or processed) data using our algorithms. The server/service can prepare reports and email links to results to investigators or home users or provides access via webpage.

The server can optionally integrate with other web-based health and/or fitness monitoring services provided by the same or other providers. Such services monitor data such as weight/weight change, heart rate, blood pressure, blood sugar, exercise level, and the like. In certain embodiments, the data can be integrated into a medical record for the subject where the medical record is maintained by a health care provider, and/or an insurance provider, and/or a physician or other healthcare provider, and/or a web-based healthcare monitoring service, and/or the user. Illustrative healthcare monitoring services include, but are not limited to FITBIT®, WITHINGS®, SYNCMETRICS®, ROCKHEALTH®, HEALTHBOX®, DREAMIT HEALTH®, NY DIGITAL HEALTH ACCELERATOR®, and the like.

Use of Measures of Endothelial Function in a Clinical Context.

As explained above, devices and methods are provided herein for the assessment of endothelial function in a mammal (e.g., in a human). Although studies often report endothelial dysfunction as a loss of the vasodilatory capacity (in response to a NO stimulus, like acetylcholine), the term encompasses a generalized defect in many or all the homeostatic mechanisms maintaining/modulating vascular homeostasis. Endothelial dysfunction is a broad term that can imply diminished production of or availability of NO and/or an imbalance in the relative contribution of endothelium-derived relaxing and contracting factors (such as ET-1, angiotensin, and oxidants).

For example, endothelial dysfunction in diabetes may result from a decreased bioavailability of NO (secondary to insulin resistance) coupled with an exaggerated production of ET-1 (stimulated by hyperinsulinemia or hyperglycemia). Endothelial dysfunction has been implicated in the pathogenesis and clinical course of all known cardiovascular diseases and is associated with future risk of adverse cardiovascular events.

It is well accepted that endothelial dysfunction occurs in response to cardiovascular risk factors and precedes the development of atherosclerosis (see, e.g., Shimokawa (1999) *J. Mol. Cell Cardiol.* 31: 23-37; Ross (1999) *N. Engl. J. Med.* 340: 115-126). It is generally a prevailing paradigm that endothelial dysfunction can form a common link between risk factors and atherosclerotic burden. Endothelial dysfunction actively participates in the process of lesion formation by promoting the early and late mechanisms of atherosclerosis. These include upregulation of adhesion molecules, increased chemokine secretion and leukocyte adherence, increased cell permeability, enhanced LDL oxidation, platelet activation, cytokine elaboration, and vascular smooth muscle cell proliferation and migration. Endothelial dysfunction also plays an important role in the clinical course of atherosclerosis.

Impaired endothelium-dependent vasodilatation in coronary arteries with established atherosclerosis results in paradoxical vasoconstriction, which may result in reduced myocardial perfusion and myocardial ischemia. Additionally, endothelial dysfunction actively modulates plaque architecture and portends the vulnerability of the lesion and the likelihood of rupture. Through this vasoconstrictor and inflammatory mechanism, endothelial dysfunction in atherosclerotic vessels may lead to the development of unstable coronary syndromes (see, e.g., Verma et al. (2002) *Circulation,* 105: 546-549).

Accordingly, in various embodiments the devices and methods provided herein for assessment of endothelial function can find utility in a clinical context. Thus, in certain embodiments, particularly in the context of a differential diagnosis, the measures of endothelial function provide by the devices and methods described herein find utility in the diagnosis and/or prognosis and/or in the treatment of various cardiovascular pathologies. In certain embodiments the measure of endothelial function, particularly in the context of a differential diagnosis, is an indicator of a cardiovascular pathology (e.g., atherosclerosis, hypercholesterolemia, high LDL-C, low HDL-C, high lipoprotein (a), small dense LDL-C, oxidized LDL-C, hypertension, high homocysteine, aging, vasculitis, preeclampsia, metabolic syndrome, variant angina, diabetes, active smoking, passive smoking, ischemia-reperfusion, transplant atherosclerosis, cardiopulmonary bypass, postmenopausal, Kawasaki's disease, Chagas' disease, family history CAD, infections, depression, inactivity, obesity, renal failure, increased CRP, congestive heart failure, left ventricular hypertrophy, etc.). In certain embodiments the measure of endothelial function in said mammal is printed out and/or stored on a tangible medium which, in certain embodments can comprise a medical record (e.g. a computerized medical record, a paper medical record, a medical record chip or ID, and the like).

Also, in certain embodiments methods of treating a subject for a cardiovascular pathology are provided where the methods involve assessing endothelial function in the subject using the apparatus and/or methods described herein and, where the method(s) produce a measure indicating impaired endothelial function, evaluating the measure in the context of a differential diagnosis for a cardiovascular pathology and, where indicated, performing one or more interventions for the treatment of a cardiovascular pathology. In certain embodiments the cardiovascular pathology comprises a pathology selected from the group consisting of atherosclerosis, hypercholesterolemia, high LDL-C, low HDL-C, high lipoprotein (a), small dense LDL-C, oxidized LDL-C, hypertension, high homocysteine, aging, vasculitis, preeclampsia, metabolic syndrome, variant angina, diabetes, active smoking, passive smoking, ischemia-reperfusion, transplant atherosclerosis, cardiopulmonary bypass, postmenopausal, Kawasaki's disease, Chagas' disease, family history CAD, infections, depression, inactivity, obesity, renal failure, increased CRP, congestive heart failure, and left ventricular hypertrophy. In certain embodiments the intervention comprises one or more interventions selected from the group consisting of prescribing and/or administering ACE inhibitors, prescribing and/or administering angiotensin receptor blockers, prescribing and/or administering endothelin blockers, prescribing and/or administering statins, prescribing and/or administering tetrahydrobiopterin, prescribing and/or administering folates, improving insulin sensitivity, LDL reduction, HDL augmentation, prescribing and/or administering antioxidants, prescribing and/or administering estrogen, prescribing and/or administering L-arginine, prescribing and/or administering desferoxamine, prescribing and/or administering glutathione, homocysteine reduction, lowering CRP, and reducing free fatty acid flux.

It should be understood that the methods and apparatus described herein measure endothelial dysfunction by means of measuring the consequences of vascular smooth muscle relaxation, and that these methods may therefore be applied to measure smooth muscle function simply by substituting the endogeneous source of nitric oxide (endothelial NO release) with an exogenous source, such as sublingual nitroglycerin.

It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

EXAMPLES

The following examples are offered to illustrate, but not to limit the claimed invention.

Example 1

Validation of Measurement of Endothelial Function

One way to determine the value of a new measure is to determine to what degree it is correlated to a "gold standard" measurement. In the case of endothelial function, the gold standard is dilation of coronary arteries in response to infused acetylcholine (ACh). This procedure is invasive, expensive and suitable only for diseased patients undergoing cardiac catheterization.

In the evaluation of a previous instrument that we developed for the assessment of endothelial function, we determined the correlation between our method and ultrasound-based FMD measurements in the brachial artery. While non-invasive, FMD studies are technically difficult and produce measurements with high variance.

As described herein, it is believed that that such studies are unnecessary in order to make a determination that a method is effective in assessing endothelial function. Physical methods for arterial EF evaluation typically measure changes in the material properties of the artery. The changes that occur in response to endogenous release of NO are similar in nature and magnitude to those that occur following administration of exogenous NO via agents such as nitroglycerin (NG). As a consequence, if it is shown that a measurement method is sensitive to vasorelaxation induced by NG, it can be assumed that the technique will also be sensitive to endothelium-mediated vasorelaxation. A major advantage of this method is that response to NG is intact even in individuals with endothelial dysfunction, so there is no need to perform a correlation analysis between two measurements.

To further strengthen the case, the measurement method should demonstrate sensitivity to RH-induced vasorelaxation in individuals who would be expected to have intact endothelial response.

Three individuals in the age-range of 28-38 were examined. Table 1 lists the subject characteristics. All subjects had Framingham risk scores of 1% or less, and had no history of cardiovascular disease. Each individual was assessed at least three times before and after RH induced by five minutes of suprasystolic cuff occlusion. At least one additional measurement was made using the same protocol, except without cuff inflation. Sensitivity to a 0.4 mg dose of sublingual NG was assessed three times in two individuals.

TABLE 1

Subject characteristics. (NS: no stimulus, RH: reactive hyperemia, NG: nitroglycerin).

| Subject | Gender | Age | Framingham Score | Number of Studies NS/RH/NG |
|---|---|---|---|---|
| Subject 1 | Male | 38 | 1% | 3/6/3 |
| Subject 2 | Female | 38 | <1% | 4/3/3 |
| Subject 3 | Male | 28 | <1% | 1/3/0 |

Each individual was assessed at least three times before and after RH induced by five minutes of suprasystolic cuff occlusion. At least one additional measurement was made using the same protocol, except without cuff inflation.

Sensitivity to a 0.4 mg dose of sublingual NG was assessed three times in two individuals. In the analysis that follows, all of the datasets are pooled by stimulus. This addresses the question: Can the method measure changes in arterial tone due to vasorelaxatory stimuli and with what sensitivity?

Figure 10:
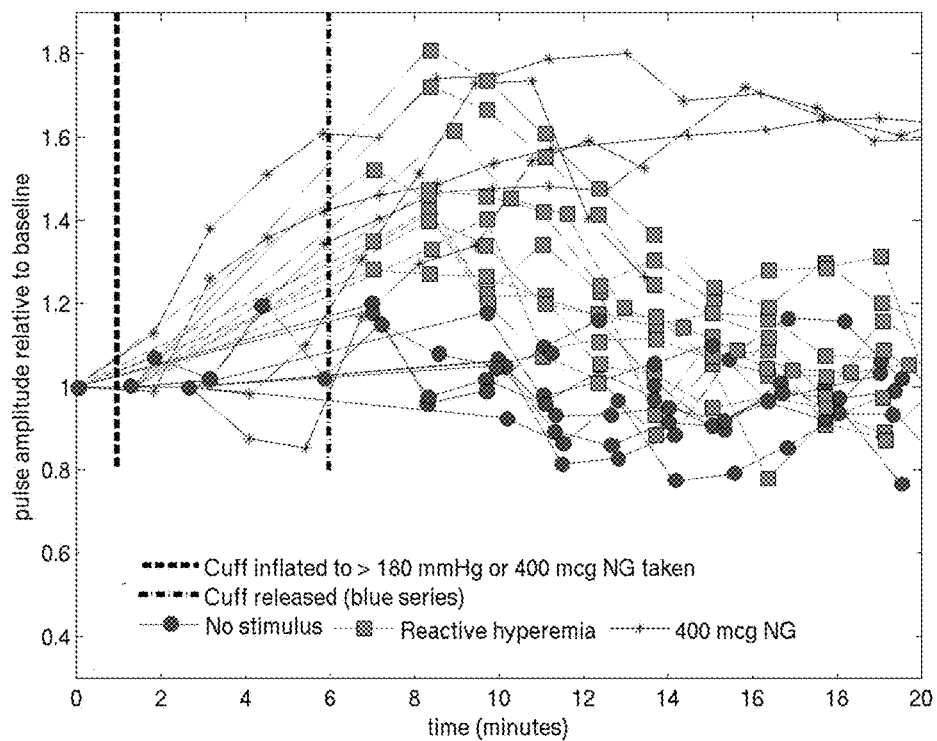
FIG. 10 shows the fractional change in pulse amplitude (proportional to area) observed relative to baseline for all studies analyzed. It is clear that the method detects much larger changes in the cases where RH or NG is used as stimulus than when no stimulus is applied. The fact that there is totally unambiguous distinction between the stimulus-present versus NS studies in all cases for the time points in the range of 8-10 minutes is extremely encouraging.

A single quantity relating to the recorded pressure data, the pulse amplitude, was studied and it was posited that this is proportional to the arterial area. During the post stimulus interval, pressure data from the cuff were recorded approximately every 80 seconds, for a period of 30 seconds. During each recording interval, the cuff was inflated to 70 mm Hg, which was always below the measured diastolic pressure of the subject. To quantify the observed response, the mean of the pulse quantity (in this case, amplitude) during the response interval was divided by the mean value of the same quantity during the baseline interval. FIG. 10 illustrates the results.

Three experiments were also performed 3 experiments on Subject 1 where dilation in the right arm was measured using ultrasound concurrently with dilation in the in the left arm measured using the device. The purpose of these studies was to examine the correlation of the response-vs-time curves.
Results FIG. 10 is strongly supportive of the hypothesis that the method is sensitive to smooth muscle relaxation for the following reasons: For the NG studies, in the time interval from 6 minutes to 20 minutes, there is a large and persistent difference between the NG responses and the NS responses. For the RH studies, there is no overlap between the RH and NS data responses during the four minutes following cuff release.

In Table 2, the maximum response for each stimulus is calculated and the statistical significance of the change relative to the NS case (one-tail Student's t test) is evaluated. Values of $p<0.05$ were considered significant.

TABLE 2

Statistical analysis of amplitude response.

| Stimulus | Mean ± SEM of maximum Response over all data sets | p-value versus NS |
|---|---|---|
| RH | 1.51 ± 0.052 | $1.19 \times 10^{-5}$† |
| NG | 1.70 ± 0.036 | $6.25 \times 10^{-6}$† |
| NS | 1.01 ± 0.068 | N/A |

Figure 11A:
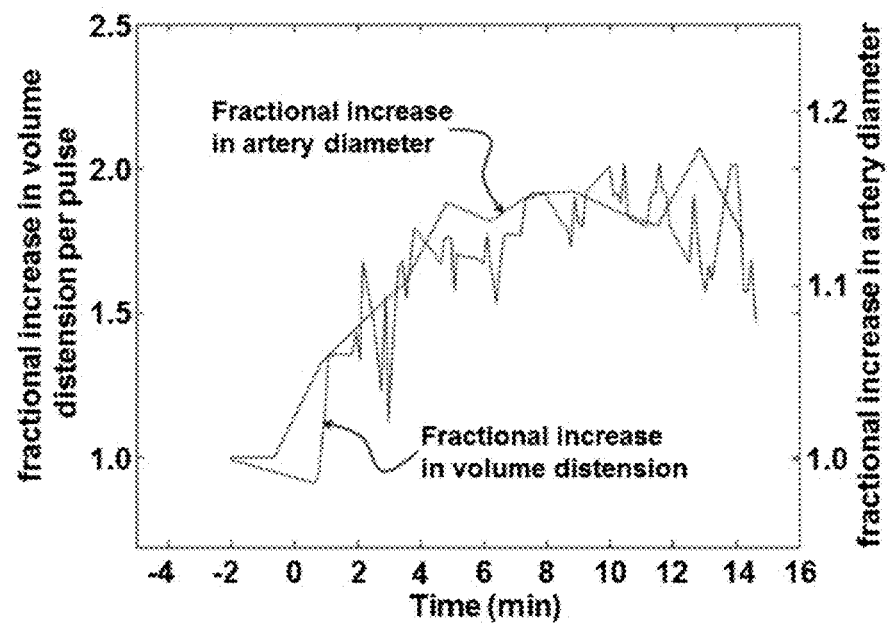
FIGS. 11A-11C show the results of concurrent measurement of artery diameter (using ultrasound imaging on right arm) and volume distention (using our method). The curves quantified by the left axes, show the fractional increase in volume distention measured using our method. The curves quantified by the right axes are arterial diameter measurements obtained using ultrasound. The stimulus at t=0 was 400 µg of sublingual nitroglycerin. The diameter measurements exhibit much higher variance, owing to the extreme sensitivity of the method to slight motion of the subject. As in other studies, these results show that our method is 5 times more sensitive to dilation than diameter measurements
Figure 11B:
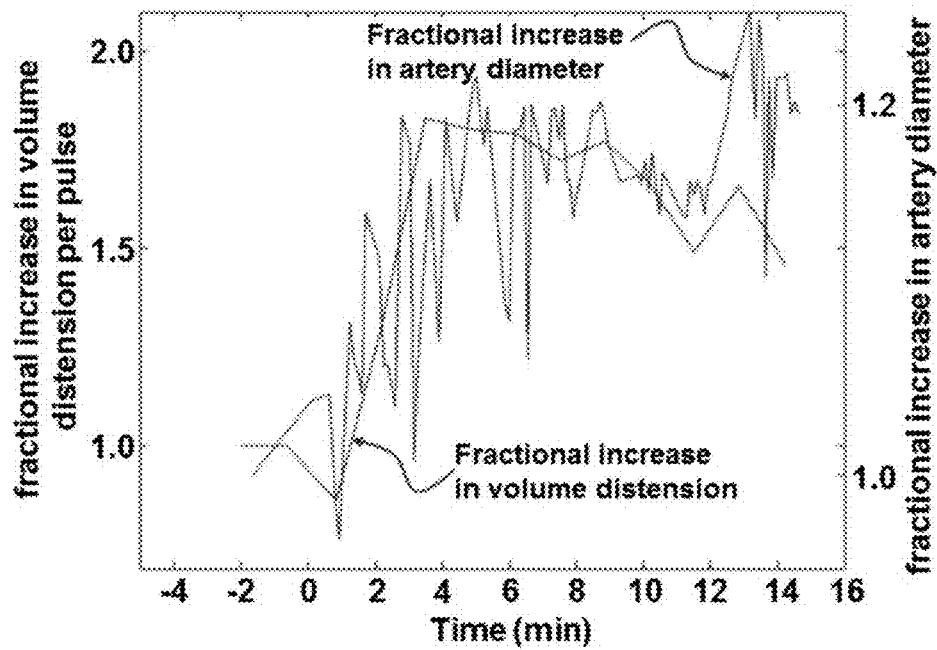
Figure 11C:
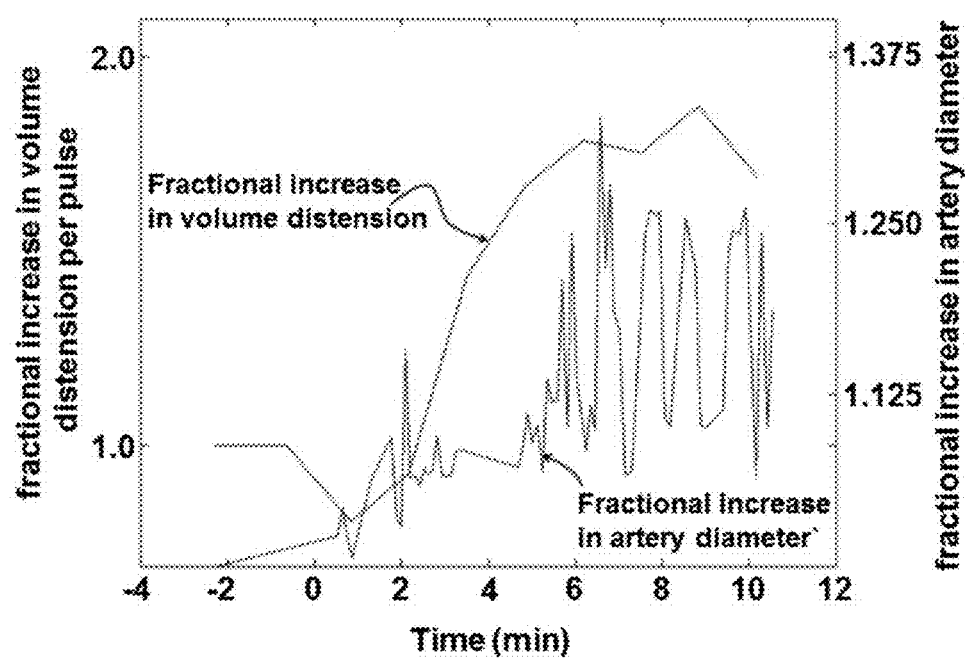

FIGS. 11A-11C provide the results of the 3 studies where measured artery diameter was measured using ultrasound and simultaneously volume distention was measured by the method described herein. The time courses of dilation are similar in all three cases. As observed in our other studies, the sensitivity of our method is≈5 times greater than diameter measurements. The diameter measurements exhibit high variance owing to the extreme sensitivity of the method to slight movement of the subject's arm
Conclusion.

While the current sample size of three subjects is small, the use of repeated measurements per subject has demonstrated with great statistical certainty that the proposed measurement device is capable of detecting changes due to RH ($p=1.19\times10^{-5}$) and NG ($p=6.25\times10^{-6}$) in all subjects on all occasions. This statistical analysis invalidates the null hypothesis that RH or NG evoke equal responses to NS in this set of subjects. The fact that there is no overlap between NS and either of the response classes in FIG. 10 is a truly impressive result.

As discussed above, since NG response is intact in almost all individuals, little is gained in examining a larger population. The results show that the sensitivity of the method is approximately 5 times greater than that of ultrasound-based imaging of arterial diameter in response to flow-mediated dilation (FMD due to RH). This is based on a comparison of the 51% mean maximum increase in pulse amplitude over baseline versus the approximate 10% brachial artery diameter change representative of an intact endothelial response in B-mode ultrasound FMD studies in the literature.

Example 2

Measurement of Brachial Artery Endothelial Function Using a Standard Blood Pressure Cuff This example presents method of measuring changes in the cross-sectional area of the brachial artery that requires neither relatively costly and bulky ultrasound equipment, nor any technical skill on the part of the operator. Instead of ultrasound, a standard blood pressure cuff is used to take the measurement. The cuff is partially inflated during the measurement process, so that changes in the area and compliance of the vessel can be calculated from tiny pressure variations in the cuff. The partially inflated cuff removes (mechanically unloads) stress from the arterial wall, and this amplifies the absolute change in area and compliance seen in response to endothelial stimulus (Bank et al. (1995) Circ. Res. 77(5): 1008-1016), allowing ensuing vasorelaxation to be measured much more easily. The same cuff may be used to occlude the artery and thus provide reactive hyperemic stimulus for FMD measurements.

We begin by explaining the physical and physiological basis of the measurement. We then describe the initial prototype of the device, and then demonstrate that the device may be realized by reprogramming a consumer-oriented electronic sphygmomanometer. The method is then evaluated on human volunteers and the results are compared to ultrasound-based FMD (uFMD) studies performed on the same limb 10 minutes following the proposed cuff FMD (cFMD) measurements. A list of abbreviations used in this paper appears in Table 3.

TABLE 3

Abbreviations used in this example.

| | |
|---|---|
| ACE | angiotensin-converting enzyme |
| A/D | analog-to-digital |
| BP | blood pressure |
| CAD | coronary artery disease |
| cD | vasodilation due to any stimulus, measured using cuff-based method |
| cFMD | flow-mediated vasodilation, measured using cuff-based method |
| CVD | cardiovascular disease |
| DC | direct current (mean signal value) |
| EDHF | endothelium-derived hyperpolarizing factor |
| EFMA | endothelial function in major arteries |
| FMD | flow-mediated vasodilation |
| NG | Nitroglycerin |
| NO | nitric oxide |
| NOS | nitric oxide synthase |
| NS | no stimulus applied |
| PC | personal computer |
| RH | reactive hyperemia |
| RH5 | reactive hyperemia after release of 5 minute occlusion |
| SD | standard deviation |
| SEM | standard error of the mean |
| uFMD | FMD, measured using ultrasound imaging |

Methods.
2.1. Principles of Operation
One key to making FMD much easier to assess is to use a cuff to measure changes in arterial cross-sectional area, instead of using ultrasound imaging to measure arterial diameter. This allows us to eventually create a subject-operated consumer-oriented measurement device that can take advantage of convenient hardware and software platforms, such as smart phones and tablets, as we will describe in Section 2.3.3.

When the cuff is partially inflated so that it fits the arm snugly, changes in cuff pressure are proportional to changes in the volume of the underlying arm (this is the basic principle of plethysmography). Since blood volume changes most rapidly in the conduit arteries, the rising edge of each pulse (diastole to systole) reflects changes in the volume of these arteries enclosed by the cuff.

FMD studies seek to measure the amount of vascular smooth muscle relaxation that occurs as a consequence of endothelial stimulus. The fundamental quantity affected by this relaxation is arterial wall compliance (uFMD measures change in vessel caliber, which is only one consequence of relaxation of vascular smooth muscle (Nichols and O'Rourke, McDonald's blood flow in arteries, 3rd ed. Edward Arnold, 1990, pp. 100-101]). We now explain how we can use the volume change measurements derived from the cuff to measure compliance.

The induction of local reactive hyperemia by means of cuff occlusion and subsequent release does not change systemic blood pressure. Under these circumstances (which should ideally be verified for each study), the pressure changes observed from diastole to systole are proportional to the concomitant volume changes. Let $\Delta V_b$ and $\Delta V_r$ denote the volume changes from diastole to systole under baseline and post-stimulus response conditions. Since the cuff is part of a sealed pneumatic system, the pressure-volume product is constant (P V=k). If the cuff snugly encloses the limb and the outer cuff sheath is non-elastic, the total volume (the volume of the enclosed limb+the volume of the cuff) maintains a constant value even as the blood volume changes. An increment in arterial pressure leads to an increase in arterial volume, which reduces the volume of the cuff by an equal amount (by compressing its contents). This, in turn, effects a pressure increase in the cuff that is proportional to the volume change in the artery.

Stating this formally:

$$V_l = V_c = V_{total} = (V_l - \Delta V) + (V_c + \Delta V) \text{ and}$$

$$P_c V_c = k = (P_c + \Delta P)(V_c + \Delta V),$$

where Pc is the cuff pressure, Vc is the cuff volume and $\Delta V$ is the change in volume of the enclosed limb, $V_1$. We now solve for the observed change in cuff pressure $\Delta P$ as:

$$\Delta P = -\frac{P_c}{V_c - \Delta V} \Delta V. \tag{1}$$

This is non-linear in $\Delta V$, but since we have $\Delta V \ll V_c$ (the perturbation in the cuff volume due to the pulse is much smaller than the cuff volume), this strongly approximates a linear relationship with a slope $-P_c/V_c$. Since the length of the artery under the cuff, l, does not change appreciably during the cardiac cycle, we may thus assume that $\Delta P \propto \Delta A$, where A is the cross-sectional area of the arterial lumen. If we denote the pre- and post-stimulus areas as $A_b = V_b/l$ and $A_r = V_r/l$, respectively, the cFMD metric is given by:

$$cFMD\ \% = \left[\frac{A_r}{A_b} - 1\right] \times 100. \tag{2}$$

This expression is an area analog of the standard FMD metric:

$$uFMD\ \% = \left[\frac{d_r}{d_b} - 1\right] \times 100, \tag{3}$$

where d represents arterial diameter. It is important to remember that that the areas are obtained during wall unloading, and are not, in general, equal to $\pi d^2/4$ (under the assumption of a circular cross section), since those diameters are measured at full transmural pressure.

The small volume changes that occur in the artery lead to very small pressure changes in the cuff, which are difficult to measure accurately. However, as the degree of cuff inflation increases and more pressure is applied to the limb, mechanical stress on the wall of the artery is relieved by the cuff. This mechanical unloading decreases the influence of stiff collagen fibers on the vessel wall properties, and this leads to a large increase in vessel distensibility (Bank et al. (1996) Circulation, 94(12): 3263-3270).

FIG. 2 illustrates diametric distension waveforms obtained using M-mode wall tracking (Wall Track System II, Pie Medical, Maastricht, Netherlands). Decreasing the transmural pressure by 80 mmHg leads to a more than twenty-fold increase in maximum distension in response to the same diastolic to systolic pressure transition. This is consistent with the very carefully executed intra-arterial ultrasound measurements of Bank and co-workers (Bank et al. (1995) Circ. Res. 77(5): 1008-1016). FIG. 16 illustrates the results of those studies, showing the change in brachial artery compliance across the full range of transmural pressure. The compliance characteristic is shown before and after the arterial smooth muscle is relaxed using nitroglycerin (NG). When the transmural pressure is reduced to ≈25 mmHg, we see that the absolute difference in vessel compliance between the baseline and relaxed state is maximized. The relevant observation is that relaxation of the artery (such as that due to FMD) is much easier to measure when the artery wall is unloaded, simply because the magnitude of the induced change is a larger quantity. A larger change in compliance means that a larger increase in arterial cross-sectional area is achieved for a given pressure rise from diastole to systole.

In the above theoretical justification of the proposed measurement method, we assume that the tissue between the cuff and artery is incompressible, and that it does not change in volume between the pre- and post-stimulus intervals. The thickness and consistency of this tissue will affect the relationship between the volume of the artery and the pressure in the cuff. However, since the cFMD metric is normalized to a baseline measurement, as long as this relationship does not change between the pre- and post-stimulus measurement intervals, the characteristics of this tissue should not influence the results. It is reasonable to expect that the vasodilatory stimulus will cause some vasodilation of resistance vessels in the surrounding tissue, and elsewhere in the limb distal to the occlusion (Nichols and O'Rourke (1998) McDonald's blood flow in arteries, 4th ed. Edward Arnold, pp. 258-259). The former effect will cause the cFMD metric to somewhat overestimate the pure arterial response. The effect of the latter is to decrease wave reflection at distal sites (owing to arteriolar dilation), and this may reduce the amplitude of the systolic peak, leading to underestimation of the arterial dilation. Since the rising edge of the distension waveform (luminal volume) is in phase with the pressure waveform (Meinders and Hoeks (2004) *Ultrasound in Med. & Biol.* 30(2): 147-154), changes in wave reflection in the distal limb will bias both uFMD and cFMD to a similar extent. We consequently can ignore this effect as a differential confounding influence.

To quantify the effect of vasodilation in intervening tissues, we compare the 5%-95% rise times of the distension waveform (obtained using M-mode wall tracking, as was used to produce the waveforms in FIG. 2) with the cuff pressure waveform. Similar rise times would imply that this part of the cuff pressure waveform (from which the cFMD metric is chiefly derived) is due to the direct effect of arterial luminal area increase. The reason for this is that low caliber collateral vessels provide much larger resistance to flow than conduit vessels and the time constant for volume change is thus much longer. For example, in the human finger, the pulse transit time over the short distance from the digital arteries to the skin of the same finger is more than 200 ms, which is longer than the rise times of both the distension and cuff pressure waveforms (Bernjak and Stefanovska (2009) *Physiol. Meas.* 30(3): 245). Examining 55 typical rising edges of the cuff pulse pressure waveform, we calculate a mean (±SD) rise time of 133±8 ms. The corresponding distension mean rise time is 122±2 ms. Since the thickness of the intervening tissue bed is much larger than that encountered in the finger, it is unlikely that the volume change in the resistance bed could appreciably contribute to the rising edge of the waveform, since the volume increase in the tissues would occur only after we have made our cFMD measurement for a particular pulse. We thus believe that the cFMD metric is chiefly affected by dilation of the artery rather than smaller colateral resistance vessels.

2.2. Study Protocol.

A typical study proceeds as follows:

(i) With the subject seated or supine, the cuff is placed around the upper arm.

(ii) Blood pressure is measured.

(iii) The cuff is inflated to a value Pm, which must be less than the mean arterial pressure, for a period Tm=30 s. During this time interval, we measure and record the pressure fluctuations in the cuff. These data constitute a pre-stimulus baseline measurement.

(iv) The cuff is deflated.

Typically, Nb=3 baseline measurement series are obtained by repeating Steps (iii)-(iv), with a waiting period of $T_w$=30 s between inflations. These rest periods allow restoration of venous return.

v) The stimulus is applied. This is either 1-5 min of cuff occlusion to suprasystolic pressure Ps (for studies of endothelial function) or a dose of sublingual NG (for studies of endothelium-independent vasodilation).

(vi) After $T_p$=45 s have elapsed following cuff release or drug administration, a series of up to Nr=10 repeat measurement intervals ensue. In each interval, the cuff is inflated to $P_m$ for $T_m$ seconds, after which it is deflated for $T_w$ seconds. This large number of repeat measurements (Nr) is required only when one wishes to record the return of the vessel toward baseline.

(vii) Blood pressure is measured again to ensure it has not changed appreciably since step (ii).

(viii) Each post-stimulus response is then compared to the average baseline response, to yield the area-based cFMD metric (Equation 2) defined above. As is the objective in uFMD studies, we seek the value of maximal vasodilation within the response time course as a fraction of the baseline condition of the artery.

It is very important to ensure that $P_m$ remains below the diastolic pressure throughout the entire study. Should $P_m$ exceed the diastolic pressure, the artery will collapse during at least part of the cardiac cycle. This "clipping" of the pressure waveform will generally reduce the measured $\Delta P$ for each pulse. Since any subsequent increases in area change will then be only partially reflected in the measurements, the quantity $A_v/A_b$ may be underestimated.

Steps (ii) through (viii) can be completely automated and ensue without the need for user intervention.

2.3. Device Prototypes

The following three prototypes implement the method. The successive prototypes evolve not in terms of measurement quality (which is superior in the first prototype), but in suitability for routine and home use.

2.3.1. Prototype I

FIG. 1 is a schematic of the first prototype. A rapid cuff inflator (E20, D.E. Hokanson, Inc., Bellevue, Wash.) is employed to set the cuff pressure to constant values for the occlusion and measurement intervals. This air source provides servo regulation that is too fast to allow its direct application to the cuff without attenuating the (desired) signal due to the expansion of the arterial lumen. Consequently, we employ a 1 m length of 2.79 mm-internal diameter intervening tubing, which serves as a pneumatic low pass filter.

The pressure in the cuff is measured using a pressure transducer. This prototype employs a Millar catheter pressure sensor (Mikro-tip, Millar Instruments, Houston, Tex.) for this purpose. The signal output of the Mikro-tip system is amplified using an instrumentation amplifier (AD627, Analog Devices, Inc., Norwood Mass.) and a low-pass filter, with a cut-off frequency of 25 Hz (8th order elliptic filter, LTC-1069-6, Linear Technology Corp., Milpitas, Calif.). It is then digitized at 1 kHz using an A/D converter card (NI-6035, National Instruments, Austin, Tex.).

A PC controls the inflation and deflation of the cuff in accordance with the protocol using a data line of its parallel printer port.

Prototype I is superior to Prototypes II and III, described below, in terms of signal quality, since the unloading pressure is maintained at a constant level throughout the measurement period.

2.3.2. Prototype II

Figure 13:
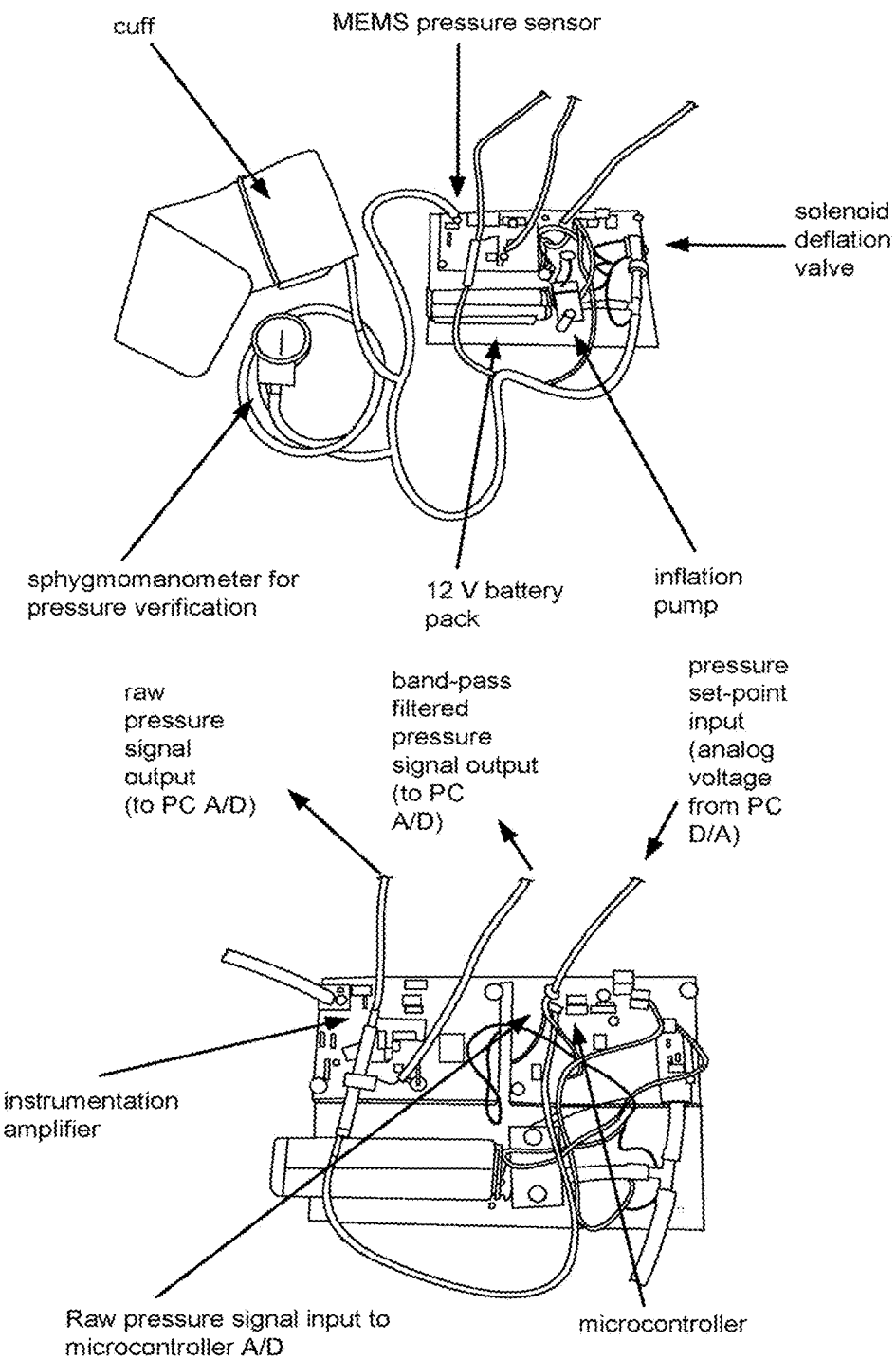
FIG. 13 shows a photograph of a portable prototype device (top) and close-up (bottom).

To make a lower cost, more compact prototype, we replace the continuously regulated air source with an on-off pressure control system, as shown in FIGS. 12 and 13. Inflation and deflation of the cuff are effected using a miniature diaphragm pump and solenoid valve (respectively, E161-11-050 and V2-20-5-PV-5-P88, Parker Hannifin Corp, Cleveland, Ohio). Cost is further reduced by employing a mass-market semiconductor pressure sensor (NPC-1210, GE Novasensor, Fremont, Calif.).

A script running on a laptop fully automates the measurement protocol. To modify the cuff pressure, the script sets a pressure-calibrated voltage on a 12-bit digital-to-analog converter on the data acquisition card. A microcontroller (PIC12F675, MicroChip Technology, Inc., Chandler Ariz.) compares this voltage to the output voltage of the pressure sensor, and it actuates the pump and valve to maintain the desired pressure within a specified tolerance.

A disadvantage of using an on-off control algorithm is that pressure tends to decrease during a measurement owing to displacement of the arm tissue under the cuff. Frequent actuation of the pump to top-up air in the cuff introduces artifacts into the acquired pulse waveform. In the description of Prototype III below, we show how the acquisition may be modified to address this issue. Section 2.4 explains an alternative post-hoc approach based on regression analysis.

2.3.3. Prototype III

A consumer-oriented electronic sphygmomanometer (Wireless Blood Pressure Monitor, iHealth Lab Inc., Mountain View, Calif.) was modified by the manufacturer, under the supervision of our group, to implement the protocol described in Section 2.2. The device operates in the same manner as Prototype II.

Figure 19:
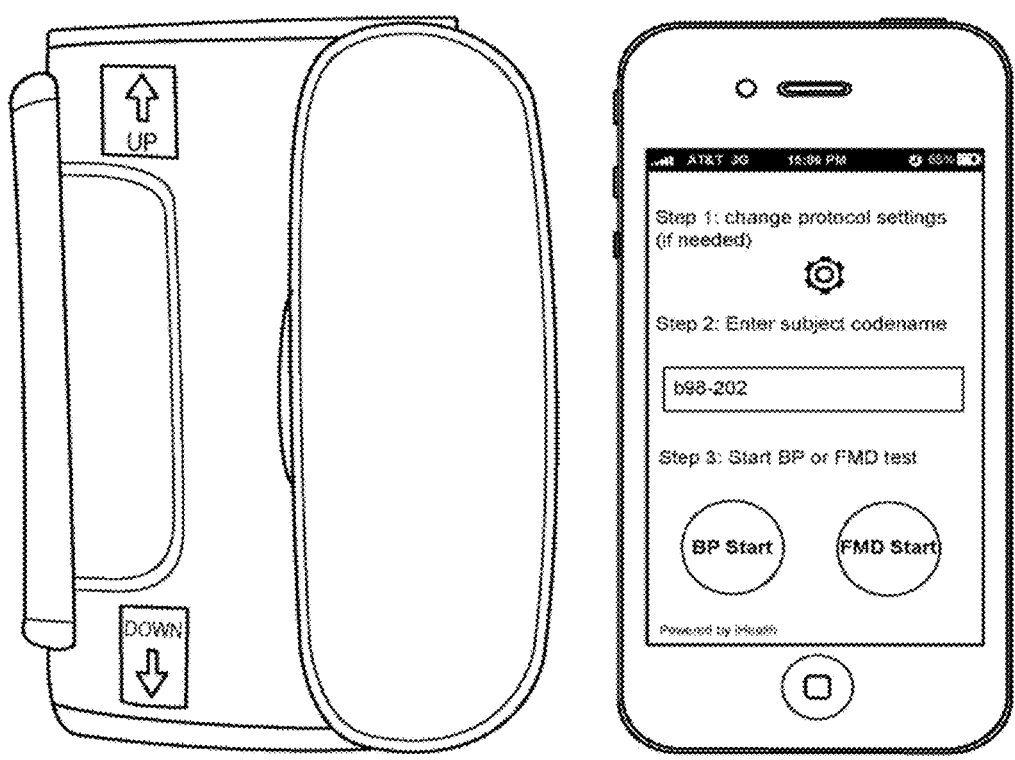
FIG. 19, left shows a photograph of an iHealth BP5 wireless blood pressure cuff. The cuff firmware is modified to allow users to execute the cFMD measurement protocol. Right: Measurement application running on an iPhone 5 that obtains the pressure waveforms from the cuff via Bluetooth.

The protocol parameters are set, and measurements are invoked, by a custom application (app) for Apple iOS handheld devices, including iPhone and iPad (Apple Inc., Cupertino, Calif.). FIG. 19 shows the wireless cuff and the running app.

Figure 6:
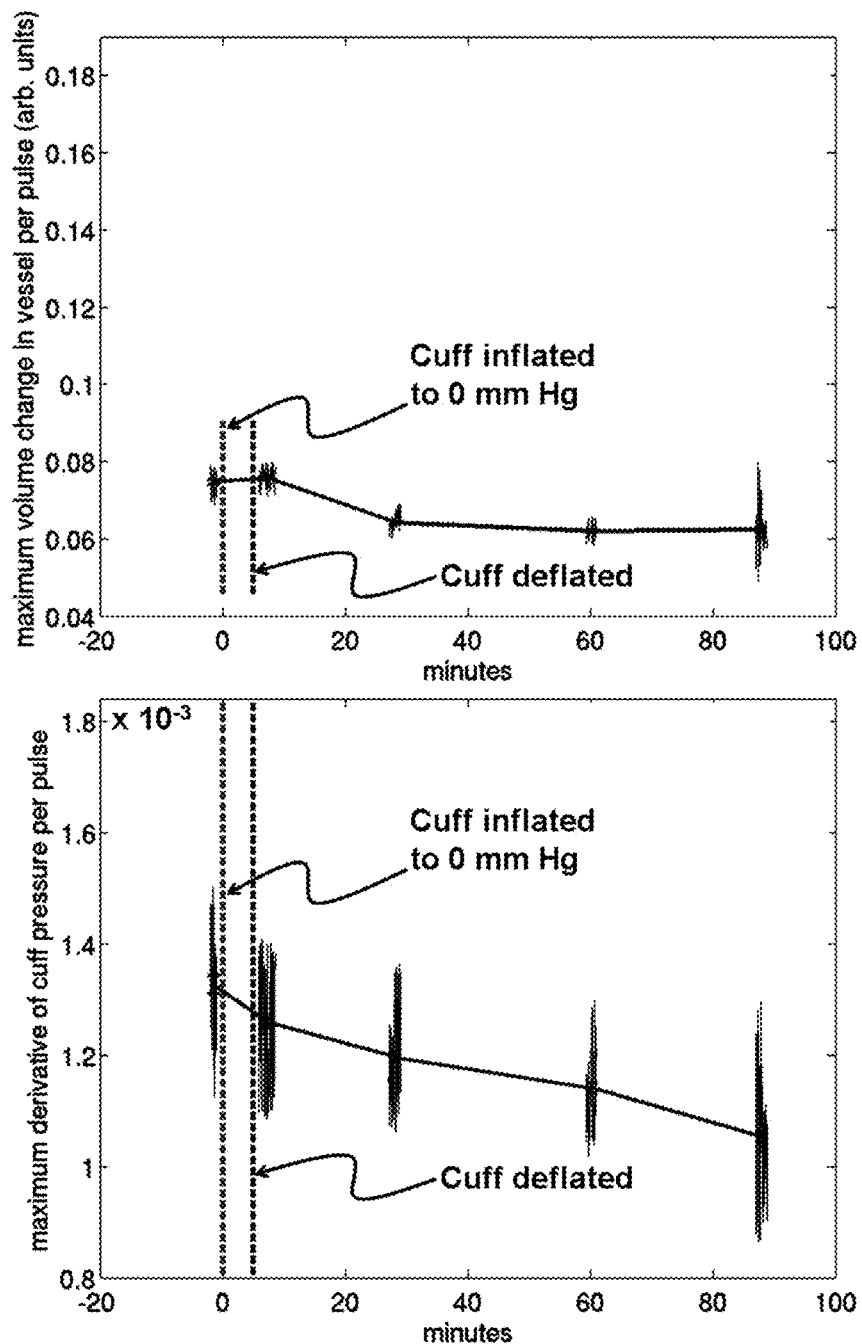
FIG. 6 shows results of a study of the same individual in which the same protocol is performed except that the cuff is not inflated to suprasystolic levels. Some natural drift in the baseline signals is evident, but the magnitude of this variation is far less than the response elicited by reactive hyperemia.

As shown in FIG. 6, a measurement interval of length T is divided into two segments, T1 and T2, such that T=T1+T2. The purpose of T1 is to stabilize the pressure close to the measurement pressure set-point during the period when tissue compression under the cuff leads to a natural pressure drop. Once the pressure has stabilized, T2 begins, during which no control of the pressure is exercised, or the criteria for initiating pressure corrections are considerably relaxed.

Figure 20:
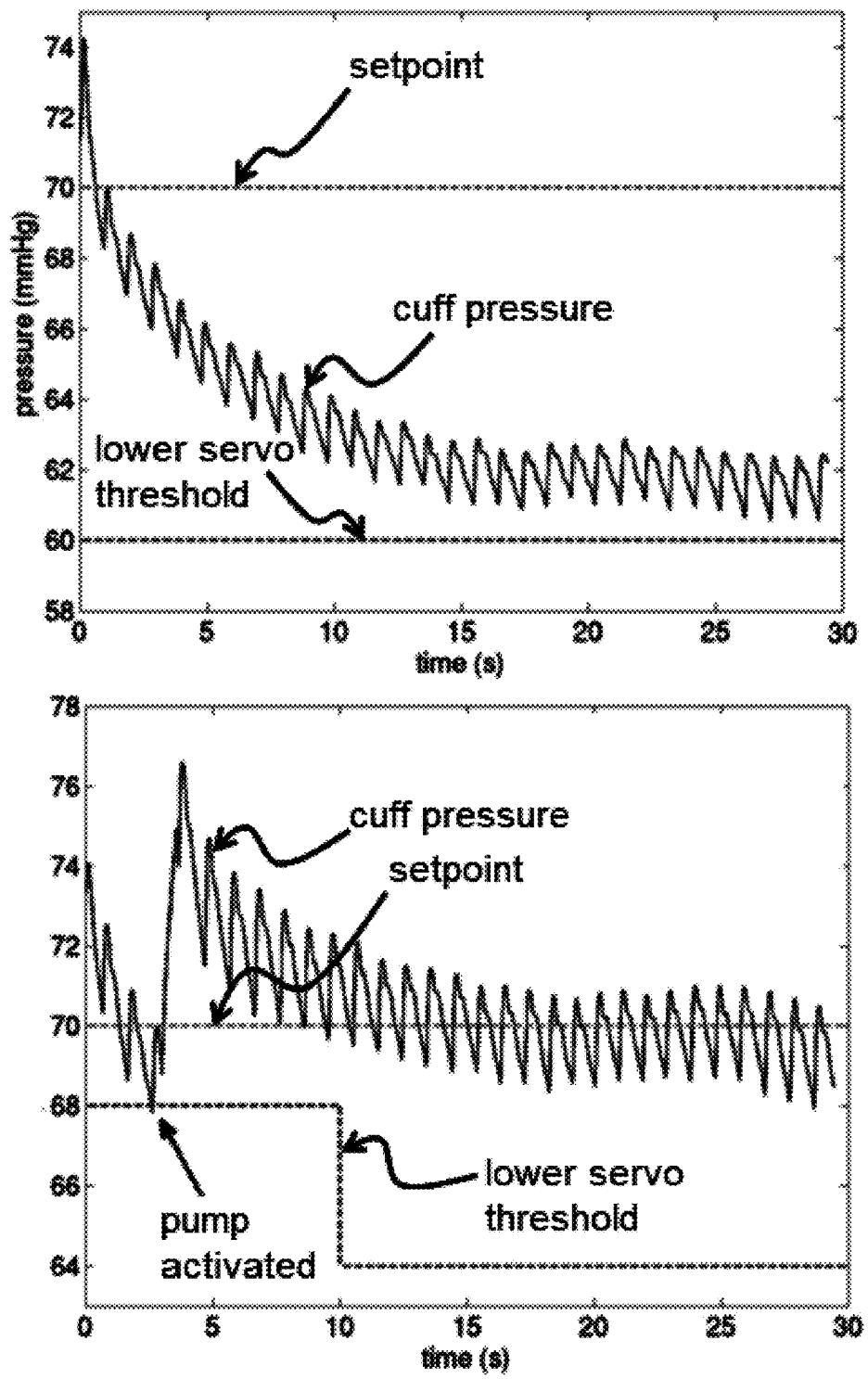
FIG. 20 shows an illustration of approaches to improve consistency of mean measurement pressure by addressing variations in pressure due to compression and conformation of the tissue under the cuff. The signal in the top panel is acquired with a large servo threshold pressure tolerances of $\Delta P_1 = \Delta P_2 = 10$ mmHg with respect to the setpoint of 70 mmHg. Subsidence of tissue under the cuff leads to a drop of over 7 mmHg below the set-point over the first 15 s. To yield the data in the bottom panel, the servo threshold is set to $\Delta P_1 = 2$ mmHg for the first $T_1 = 10$ s, and $\Delta P_2 = 4$ mmHg for the remaining $T_2 = 20$ s. These settings lead, in this case, to a stabilization of the signal close to the set-point during the first 10 s. While the relaxation of the pressure bounds during the last 20 s does not have an effect for this time series, it generally reduces signal disruption due to servo action during the later segment of the acquisition period.

Different pressure tolerances $\Delta P_1$ and $\Delta P_2$ may be applied to the respective time segments $T_1$ and $T_2$. During interval $T_n$, adjustment of the pressure is only initiated when the cuff pressure $P<P_s-\Delta P_n$ or $P>P_s+\Delta P_n$. By setting, for example, $\Delta P_2 > \Delta P_1$, it is possible to avoid unnecessary servoing during $T_2$ that may render measurement data unusable. FIG. 20 provides an example of the specification of these ranges and the interpretation of these quantities.

2.4. Signal Processing

For the $T_m$ second time record for measurement series i, p(t) is processed as follows:

(i) A 2-pole high-pass Butterworth filter with cutoff frequency of 0.5 Hz is applied to remove the DC component of the cuff pressure signal, yielding $p_{AC}(t)$.

(ii) A peak and foot detection algorithm identifies the individual pulses. Outliers in terms of pulse height, rise time, and period are discarded.

(iii) For Prototype I, in which there is continuous pressure control, the remaining pulse heights are averaged to yield a value $\overline{\Delta P_i}$ for each measurement interval. For the other prototypes, which use on-off control, linear regression is used to adjust the pulse heights to the mean cuff pressure over all intervals i. The mean of the adjusted pulse heights for each i is then taken. This reduces bias introduced by variations in unloading pressure that occur during each measurement interval when on-off control is employed. These biases are introduced by shifting the operating point along the transmural pressure axis of FIG. 16. Based on the behavior of these curves, it appears reasonable to fit a linear model around an operating point close to 20 mmHg transmural pressure.

(iv) The maximum of the cFMD metric in Equation 2, analogous to that used for uFMD, expressed directly as a function of the measurement data, is calculated as $$cFMD_{max} \% = \left[ \frac{\max_{N_s \geq k > N_b} \overline{\Delta P_k}}{1/N_b \sum_{n=1}^{N_b} \overline{\Delta P_n}} - 1 \right] \times 100 \quad (4)$$

and reported, e.g., to the user. This value reflects the ratio between the mean of all baseline measurement set means and the highest mean among the post-stimulus measurement intervals. Where this metric applies to general stimulus (e.g., reactive hyperemia or nitroglycerin), we denote it $cD_{max}\%$.

2.5. Evaluation in Human Subjects: Preliminary Studies

We seek first to establish whether the method:

(i) Is sensitive to smooth muscle relaxation due to sublingual nitroglycerin.

(ii) Is sensitive to vasodilation following reactive hyperemia in subjects with very low CVD risk.

(iii) Exhibits good repeatability.

Since the day-to-day FMD response is dependent on many factors (e.g., food, medication, menstrual state and time-of-day), the consistency of the measurement method itself is best assessed via nitroglycerin studies.

A total of three subjects are examined up to six times each for each of three stimuli:

(i) RH following 5 minutes of cuff occlusion (RH5);

(ii) 400 µg of sublingual nitroglycerin (NG); and (iii) No stimulus (NS), equivalent to no cuffination, or zero dose of drug.

Table 1, supra, provides details of the three subjects examined and the number of repeat tests performed for each stimulus. These subjects were examined at Lawrence Berkeley National Laboratory under an approved human subjects protocol.

2.6. Evaluation in Human Subjects: Correlation Between cFMD and uFMD

While our small-sample preliminary studies can potentially provide evidence of the sensitivity and repeatability of the method, more convincing validation requires an adequately powered comparison of cFMD with an accepted measure of FMD. We do this by comparing cFMD and uFMD methods in the same subjects on the same day and at the same time of day. We now describe the experimental design of this study.

2.6.1. Study Population.

We examined human volunteers currently involved in a study of the effects of omega-3 fatty acid supplementation on vascular physiological parameters in patients with peripheral artery disease (PAD). These volunteers consisted of subjects with known PAD and aged-matched, non-PAD controls. Most of the controls, however, were of advanced age and had other cardiovascular disease. This population was chosen for convenience and availability: inclusion of controls with a lower risk of CVD would enable evaluation of the correlation between cFMD and uFMD over a wider range of endothelial competency. Since uFMD has high variability, it is difficult to differentiate poor responders into multiple tiers. The scatter of uFMD measurements alone can mask correlations for such groups. We proceeded with the study notwithstanding this anticipated difficulty.

The characteristics of the subjects who participated in this study are listed in Table 4. These subjects were examined at the San Francisco VA Medical Center, under approval from the relevant ethics board.

TABLE 4

Subject characteristics for cFMD/uFMD correlation study.
Mean values are shown ± their standard deviations.

|  | All | Systolic Hypersensitives Excluded |
|---|---|---|
| Number of subjects | 27 | 16 |
| # female | 8 | 6 |
| Age (years) | 64.1 ± 10.0 | 63.3 ± 10.1 |

TABLE 4-continued

Subject characteristics for cFMD/uFMD correlation study.
Mean values are shown ± their standard deviations.

|  | All | Systolic Hypersensitives Excluded |
|---|---|---|
| Mass (kg) | 86.0 ± 18.0 | 81.8 ± 17.9 |
| BMI (kg/m$^2$) | 29.0 ± 4.6 | 28.4 ± 4.8 |
| # diabetic | 7 | 4 |
| # tobacco ever | 17 | 9 |
| # tobacco current | 6 | 3 |
| Systolic BP (mmHg) | 144.8 ± 23.1 | 130.6 ± 7.5 |
| Diastolic BP (mmHg) | 87.3 ± 9.8 | 82.2 ± 4.9 |

2.6.2. Ultrasound FMD Study Protocol uFMD measurements were performed in accordance with currently recommended guidelines and standards (Corretti et al. (2002) *J. Am. Coll. Cardiol.* 39: 257-265; Thijssen et al. (2011) *Am I Physio.-Heart Circ. Physiol.* 300(1): H2-H12) and as we describe in (Owens et al. (2009) *J. Vasc. Surg.* 50(5): 1063-1070). Before the study, subjects are required to fast for at least 8 hours and desist from nicotine products for at least 4 hours. A history of recent medications was recorded. Subjects rested for 10 minutes in a supine position in a darkened room at 23° C. The subject's arm was then extended onto a movement-constraining pillow with the palmar aspect oriented anteriorly. A 5-cm-wide tourniquet blood pressure cuff was placed on the upper arm distal to the insertion of the deltoid. The length of the brachial artery was surveyed using B-mode ultrasound (Philips HD11, Philips Healthcare, Best, Netherlands) with a broadband linear array transducer with a 3{12 MHz range (Philips L12-3) until a straight segment with a visible registration structure can be located. The probe was oriented so that the artery was at least 3 cm below the surface of the skin, and the focus is aligned with the deep boundary of the vessel. The protocol requires that the boundary between the intima and lumen be clearly visible. Prior to cuffination, the baseline diameter of the vessel and blood flow velocity were recorded for 60 seconds using electrocardiogram-gated image capture software (Brachial Imager, Medical Imaging Applications LLC, Coralville, Iowa). Baseline blood flow velocity was recorded for 60 s using an insonation angle of 60°. The Doppler sample gate was positioned to cover the center, but not the edges, of the lumen. The probe remained in a fixed position between measurements. The blood pressure cuff was then inflated to the greater of 250 mm Hg or 50 mm Hg above the subject's systolic blood pressure for a period of 5 minutes.

Recording of the B-mode images began 10 s prior to cuff release. Bloodflow velocity was assessed for a period of 30 seconds post-cuff release using the methods described above. B-mode images were recorded until 3 minutes post-cuff release. Analysis of the images was performed using continuous edge-detection software (Brachial Analyzer, Medical Imaging Applications LLC). Baseline diameter was recorded as the mean of 60 seconds of data. From recordings obtained during the reactive hyperemic phase, the exact moment of cuff release was determined. Hyperemia diameter was calculated using a pre-determined time window (55-65 s post-cuff release). uFMD % was calculated as:

$$uFMD \% = 100 \times \frac{d_{60S} - \bar{d}_b}{\bar{d}_b},$$

where $d_{60s}$ represents the diameter measured at 60 s after cuff release, and $d_b$ is the average baseline diameter.

2.6.3. Sample Size Selection

We based our sample size on that recommended for uFMD, since our preliminary data suggested that the cFMD method is less variable and much more sensitive than uFMD.

Sample sizes of 20-30 per group have been previously used in uFMD studies that attempt to compare endothelial function between two groups (Corretti et al. (2002) *J. Am. Coll. Cardiol.* 39: 257-65). With this sample size, the minimal statistically significant change that can be detected with an intervention at this group size is an absolute change in FMD of 1.5% to 2% α=0.05, β=0.2 [power of 80%]).

The statistics obtained from 399 papers that appear in the meta-analysis of (Witte et al. (2005) *J. Am. Coll. Cardiol.* 45(12): 1987-1993) were also useful for sample size selection. It is reasonable to expect that the measurement variance for a meta-analysis is higher than that for individual laboratories and will consequently lead to an overestimate of the number of subjects required. Power analysis using the G*POWER 3.03 software package (Erdfelder et al. (1996) *Behav. Res. Meth. Inst. & Comp.* 28: 1-11) for a power of 80% at a confidence level of 95% yielded a sample size of 21 subjects per group to differentiate subjects in the 1st and 3rd tertiles of Framingham risk, and 63 per group to differentiate between the 1st and 2nd tertiles. Based on the literature cited above, we chose a minimum group size of 21.

Since the purpose of this part of the study was to determine whether cFMD and uFMD are correlates, rather than investigate FMD under different disease states, we combined the data from control and PAD subjects in one group.

3. Results 3.1. Preliminary Studies of cFMD

In Table 5 we calculate the maximum response for each stimulus and evaluate the statistical significance of the change relative to the no stimulus (NS) case (one-tail Student's t-test). Values of p<0:05 are considered significant.

TABLE 5

Statistical analysis of dilation response ($cD_{max}$ %).

| Stimulus | Mean ± SEM of maximum response over all data sets | $cD_{max}$ % | p-value versus NS |
|---|---|---|---|
| RH | 1.51 ± 0.052 | 51% | 1.19 × 10$^{-5}$† |
| NG | 1.70 ± 0.036 | 70% | 6.25 × 10$^{-6}$† |
| NS | 1.01 ± 0.068 | 1% | N/A |

Figure 21:
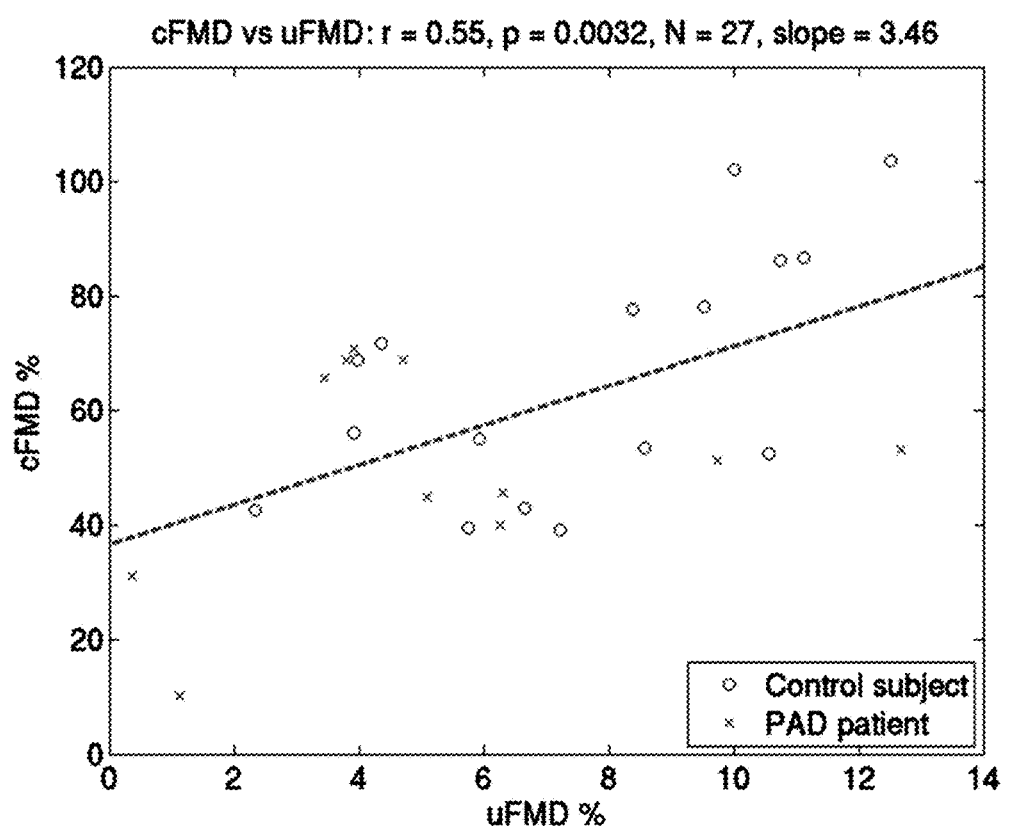
FIG. 21 shows a scatter plot of measurements of cFMD % vs. uFMD % for N=27 total subjects. We observe a correlation coefficient of r=0:55, which is statistically significant with p=0:003.

†statistically significant
SEM: standard error of the mean 3.2. Flow-mediated Dilation: Ultrasound-Versus Cuff-based Measurements FIG. 20 is a scatter plot that shows cFMD vs uFMD measurements for N=27 subjects. The slope of the regression line indicates that cFMD is 346% more sensitive to the underlying stimulus than uFMD. When systolic hypertensive subjects (those having systolic blood pressure greater than 140 mmHg) are removed from the dataset, we found an increased correlation, as shown in FIG. 21. (The rationale behind performing this particular analysis is based on the correlation between arterial stiffness and endothelial dysfunction observed in (Wallace et al. (2007) *Hypertension*, 50(1): 228-233). The relevance of those results to the present study is discussed below.)

Discussion.

A prudent first step in the evaluation of any new method or protocol for assessment of endothelial function is to establish sensitivity to endothelium-independent smooth muscle relaxation. By comparing the response of subjects to 400 μg and a zero dose of sublingual NG (no stimulus [NS]), we can establish whether the method is sensitive to the smooth muscle relaxation that is the effect of endothelial stimulus. Smooth muscle relaxation and vasodilation are the end results of NO stimulus regardless of whether NO is endogenously generated or exogenously supplied.

The data shown in FIG. 10 demonstrate with great statistical certainty that the proposed metric can detect changes due to NG vs. NS (+70%, p=6.25×10−6). Not only do the distributions for NG and NS responses differ, but there is in fact no overlap of the distributions of these data within the time interval of maximum response, spanning from 5 minutes to 15 minutes after the administration of the drug. We have previously determined that NG at this dose does not produce changes in systemic blood pressure that could confound these measurements (Maltz and Budinger (2005) *Physiol. Meas.* 26(3) 293-307). This is especially important in the case of the present method, as correct operation according to the arguments provided in Section 2.1 requires that blood pressure remain constant between baseline and post-stimulus measurement intervals.

Since a 400 μg sublingual dose of NG is reported to elicit maximal smooth muscle dilation (Feldman et al. (1979) *Am. J. Cardiol.* 43(1): 91-97; Adams et al. (1998) *J. Am. Coll. Cardiol.* 32: 123-127) the next step was to determine whether RH following 5 minutes (RH5) of cuff occlusion produces a measurable change in the metric in individuals expected to have sound endothelial function.

RH5 indeed produces a significant change vs NS (+51%, p=1.19×10−5). In the 4 minutes following cuff release, there is no overlap between the RH5 and NS distributions (during the window of maximum response) evident in FIG. 10.

Table 5 summarizes the above findings.

These preliminary studies confirm that the method is sensitive to vasorelaxatory stimuli, but comparison with an established method is needed to determine whether a proportional relationship exists between the proposed and accepted metrics of endothelial function. FIG. 21 displays a scatterplot of measurements from the established meathod of uFMD and cuff FMD. We regard the correlation of r=0:55 observed in the data depicted in FIG. 21 as moderate to strong, in view of the fact that our study population has substantially poorer uFMD than would be expected of a general population, and since our sample size limits us to differentiation of the first and third tertiles of uFMD response. Our population sample was a convenience sample, with an over-representation of individuals with cardiac risk factors. The uFMD responses that we observed in this study are typical of the first and second tertiles of endothelial response for a larger sample of the general population. We are thus not exploring the full natural \dynamic range" of FMD and this makes it more difficult to observe stronger correlations.

Figure 22:
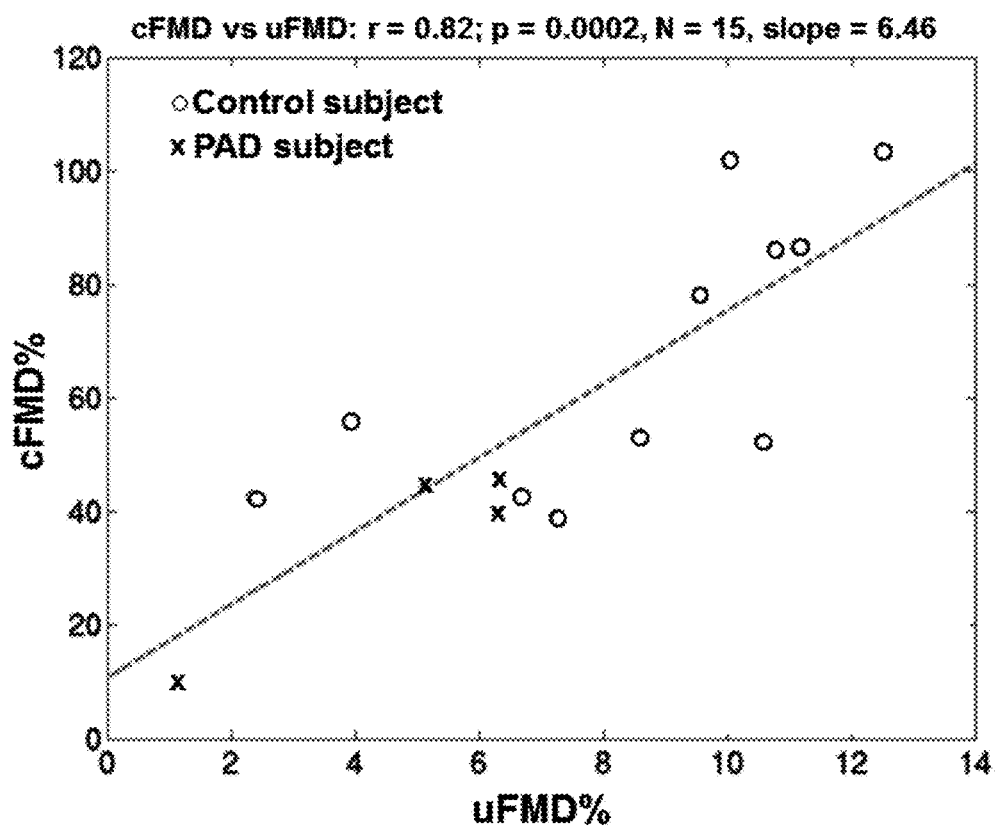
FIG. 22 shows a scatter plot of measurements of cFMD % vs. uFMD % for N=15 total subjects. We observed a correlation coefficient of r=0:82, which is statistically significant with p=0:0002. These subjects are the subset of those in FIG. 21 that exhibited systolic blood pressures of less than or equal to 140 mmHg.

Subjects with isolated systolic hypertension have been found to exhibit both high aortic pulse wave velocity (arterial stiffness) and impaired FMD (Wallace et al. (2007) *Hypertension*, 50(1): 228-233). We thus performed a subgroup analysis excluding subjects with systolic pressures above 140 mmHg, and found that the correlation between cFMD and uFMD increases to 0.82 (p<0.0002), as shown in FIG. 22. It is possible that mechanical unloading of stiff arteries allows more flow-mediated dilation to occur, since such arteries may not be as severely restricted by their collagen framework when the wall is under less stress. (Models fit to in vivo measurements indicate that collagen fibers that act in parallel with the smooth muscle are increasingly recruited as transmural pressure rises (Bank et al. (1996) *Circulation*, 94(12): 3263-3270)) If this is the case, uFMD may be systematically underestimating FMD in these subjects. This contention is further supported by reported correlations between endothelium-dependent and endotheium-independent dilations (EDD and EID) (Adams et al. (1998) *J. Am. Coll. Cardiol.* 32: 123-127. In this large study of 800 subjects, Adams et al. found a correlation of 0.41 between EDD and EID. When those subjects at higher risk of atherosclerosis were removed (diabetics as well as those with a history of tobacco smoking), the correlation coefficient fell to 0.24. It is quite possible that the impaired dilation attributed to \smooth muscle dysfunction" (Id.) is in fact due to an impaired ability of the vessel to dilate even when the smooth muscle is relaxed.

It would be interesting to conduct a similar study to compare EDD and EID in the presence of mechanical unloading. Such studies may be conducted by measuring uFMD through a water-filled cuff. It is also important to confirm this finding by performing prospective studies designed to validate this particular hypothesis on the sub-group.

Alternatively, if cFMD is overestimating dilation, the cFMD metric may need to be calibrated to systolic blood pressure in order to remove bias that may occur in cases of subjects with systolic hypertension. Our current investigations are focused on understanding this phenomenon and developing model-based calibration.

Our results show that the sensitivity of the method is between three and six times greater than that of ultrasound-based imaging of arterial diameter in response to both flow-mediated dilation and NG. Most of this sensitivity increase owes to our measurement of area rather than diameter. As is often the case, a greater fundamental sensitivity to the measured quantity makes it possible to use a simpler and lower-cost measurement system. We have realized the measurement in a device that is currently marketed to the consumer at a price of $99.00 US.

In concordance with current recommendations (Thijssen et al. (2011) *Am J. Physio.—Heart Circ. Physiol.* 300(1): H2-H12), we believe measurements of endothelial function in major arteries should ideally be based on NO-mediated FMD. In this sense, a limitation of the studies we perform here is that a single cuff is used for both measurement and occlusion. To assure that the dilation is purely NO-mediated requires a second cuff distal to the measurement cuff. This is equivalent to the case of wrist-occlusion in (Doshi et al. (2001) *Clin. Sci.* (*Lond*), 101: 629-635), where eNOS inhibition abolishes, rather than merely attenuates, FMD. The occlusion is then effected such that the measured segment of the artery is not subject to an ischemic stimulus during the occlusion interval. It is straightforward to modify the proposed method and apparatus to realize a split- or separate-cuff design.

The combination of evidence and physical arguments presented here suggests that cFMD and uFMD will remain correlated regardless of the method of stimulus used.

While we have demonstrated that endothelial function may be assessed using equipment of the same complexity as that used for blood pressure measurement, the time taken to acquire the data is considerably longer. In certain embodiments, the minimum time needed for a study is envisaged as equal to: baseline measurement time (15 s)+post-measurement recovery time (30 s)+occlusion time+post-cuff-release time (60 s)+response measurement time (15 s)=120 s+occlusion time. One way to shorten the study duration is to reduce the occlusion time. Corretti et al. (1995) *Am. J. Physiol*, 268: H1397-H1404, compared uFMD responses elicited by upper arm (proximal) occlusion times of 1, 3 and 5 minutes. Statistically significant responses were observed only in the case of 5-minute occlusions. While the mean dilations for 1- and 3-minute occlusions were substantial (respectively 2.1% and 7.8% vs 12.6% for 5-minute occlusion), the data were extremely variable. There is the possibility that owing to the sensitivity advantages of cFMD, measurements of the effects of a shorter occlusion might exhibit lower coefficients-of-variation. A three minute occlusion would allow measurement of cFMD in 5 minutes, which is attractive in comparison to conventional protocols. Whether shortening the occlusion interval changes the physiological basis of the observed response can be assessed via methods such as eNOS inhibition.

We believe the mass availability of a device for routine endothelial function assessment will prove clinically significant, since measurement of both acute and chronic changes in endothelial function could be accomplished for the first time. There are compelling reasons to believe that knowledge of acute variation in endothelial function in an individual is important. Since NO released by the endothelium is a potent inhibitor of the adhesion of platelets and leukocytes to the endothelial cell surface, and since adhesion of these cells is widely believed to be a necessary initiating event in atherogenesis (see, e.g., Deanfield et al. (2005) *J. Hypertens.* 23: 7-17), it is reasonable to infer that the proportion of time that the endothelium is dysfunctional constitutes an important indicator of disease risk. Just as dieters use a scale to measure body mass, and hypertensives use a home blood pressure monitor, portable endothelial function monitors can provide individuals with feedback regarding the impact of their lifestyle and medications on arterial health.

Example 3

Method for Obtaining Model-calibrated Arterial Endothelial and Smooth Muscle Function Measurements A vast body of literature exists relating endothelial function, as measured via the conventional ultrasound imaging method, to various states of health and disease. Also, the influences of factors such as diet, physical activity and medical interventions have been assessed via what we will refer to as uFMD (ultrasound-based flow mediated dilation) measurement methods. We have described a cuff-based method of assessing flow-mediated dilation (cFMD) that offers increased sensitivity by measuring cross sections area changes rather than diameter changes. While uFMD is based on changes in measures of an absolute quantity (arterial diameter), cFMD measures changes in a surrogate of vessel cross sectional area, namely the pressure in a cuff.

In order to relate cFMD to uFMD, and thus take full advantage of the existing research on uFMD, and to more easily interpret study results, it is desirable to calibrate the two measurements.

In addition, in our studies of uFMD vs cFMD, we have found original evidence that uFMD systematically underestimates smooth muscle response in subjects with stiffer arteries. This means that clinical interventions aimed at improving endothelial or smooth muscle function are not accurately assessed using the standard uFMD method. Our cFMD method, which performs the measurement on a mechanically unloaded method, is not only a more convenient and more sensitive method for these subjects, but produces a less biased estimate. In these cases, a calibration method that can measure the true response, and relate this to what would have been observed using uFMD is important for interpretation of results.

To perform a calibration, it is convenient to have a suitable:

1. Measurement protocol; and
2. Mathematical model of the artery that may be based on a combination of physical and empirical models.

Measurement Protocol

In order to perform a calibrated measurement, we adopt the following general protocol:

1. With the subject seated or supine, the cuff is placed around the upper arm (or other limb).
2. Blood pressure is measured.
3. The cuff is inflated to a value $P_m$, which must be less than the mean arterial pressure, for a period of time "Tm" (e.g., $T_m$=30 s). During this time interval, we measure and record the pressure fluctuations in the cuff. These data constitute a pre-stimulus baseline measurement.
4. The cuff is deflated. Typically multiple baseline measurement series ($N_b$) (e.g., $N_b$=3) series are obtained by repeating steps 3-4, with a waiting period ($T_w$) (e.g., $T_w$=30 s) between inflations. These rest periods allow restoration of venous return circulation. The key to enabling calibration is that $P_m$ is varied, either within each period $T_m$ and/or as a function of measurement interval index b. Typically, $P_m$ would be varied in the range of 20-80 mmHg. Since the intention is to fit a parametric model, a model with K parameters requires measurements of at least K different values. Typical values of K would be 2, 3, 4 or 5.
5. The stimulus is applied. In certain illustrative embodiments, this is either 1-5 min of cuff occlusion to suprasystolic pressure $P_s$ (for studies of endothelial function) or a dose of sublingual nitroglycerin (NG) (for studies of endothelium-independent vasodilation).
6. After time period $T_p$ (e.g., Tp=45 s) has elapsed following cuff release or drug administration, a series of repeat measurement intervals "Nr" (e.g., up to Nr=10) ensue. In each interval, the cuff is inflated to $P_m$ for $T_m$ seconds, after which it is deflated for $T_w$ seconds. A large number of repeat measurements (e.g., $N_r$=10) is required only when one wishes to record the return of the vessel toward baseline. Note that while it is desirable that the $P_m$ used to measure the post-stimulus responses be as close as possible to the $P_m$ used during baseline, this is not essential, since it is possible to effectively fit the parametric model even if these values differ or even do not overlap.
7. Blood pressure can be measured again to ensure it has not changed appreciably since step (2).
8. The post-stimulus responses are then compared to the baseline responses, to yield the area-based cFMD metric (Equation 1):

$$cFMD\ \% = \left[\frac{A_r}{A_b} - 1\right] \times 100. \quad (1)$$

where the the pre- and post-stimulus areas are denoted as $A_b$ and $A_r$, respectively. As is the objective in uFMD studies, the value of maximal vasodilation within the response time course as a fraction of the baseline condition of the artery is determined.

9. A calibration, such as that described in Section 3 below, can then applied to convert this value to a corresponding uFMD-equivalent value (by referencing the model to zero unloading pressure, i.e., $P_m=0$), or in order to formulate new FMD assessment metrics based directly on the model parameters. Values of the parameters $T_m$, $P_m$, $N_b$, $N_r$, $T_w$, and $T_p$ given above are examples of typical values.

Model of Arterial Wall Used for Calibration and Formulation of New Metrics

Background

Figure 23:
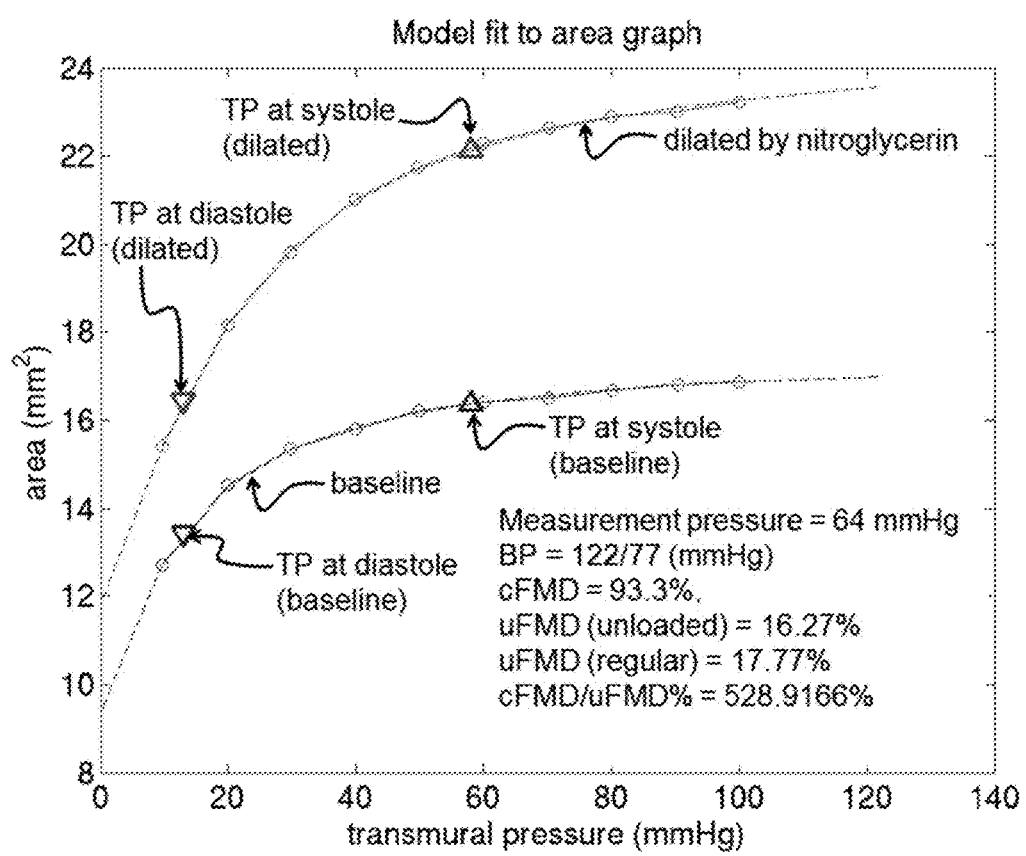
FIG. 23 illustrates an arctangent model relating artery cross sectional area to transmural pressure. These curves are applicable to an individual with a blood pressure of 122/77 mmHg.

In (Bank et al. (1999) *Circulation*, 100: 41-47), an empirical model is fit to the area versus transmural pressure curves of human arteries in baseline and dilated states. FIG. 23 illustrates such a fitted arctangent model for an individual with a blood pressure of 122/77 mmHg. Conventional uFMD is measured at a transmural pressure equal to the systolic blood pressure (no artificial mechanical unloading of the vessel wall is present). For example, to obtain uFMD from this figure, one would divide find the ratio between the rightmost value of the upper curve $A_d(122)$ and the rightmost value of the lower curve $A_b(122)$ and take its square root to convert to a ratio of diameters:

$$uFMD\% = (uFMD - 1) \times 100 = \left[\sqrt{\frac{23.57}{16.99}} - 1\right] \times 100 = 17.77\%.$$

It was a surprising discovery that that models such as these can be used as a means to convert measurements obtained under mechanically unloaded conditions to one that would be obtained under the conventional unloaded condition. The methods and devices described herein provide a protocol and measurement method for obtaining such curves that is much simpler, more sensitive, and economical than the methods used in (Bank et al. (1999) *Circulation*, 100: 41-47). Those methods involved either: 1) Ultrasound imaging through a water-filled cuff; or 2) Intra-arterial ultrasound imaging (invasive) and application of pressure via external air cuff. No attempt was made to convert measurements obtained to uFMD measurements.

The methods and devices described herein enable the measurement (typically by the averaging of many individual pulses) of the 2 samples of each of the two curves used for the demonstration above. Once the model is fit to the curves, these can be referenced to other measurement pressures than those used to acquire the data (including $P_m=0$, the case for standard uFMD studies).

One Illustrative Embodiment of cFMD-uFMD Calibration

Let $P_D$ and $P_S$ represent the diastolic and systolic pressures, respectively. The cFMD measurement can be derived from four points on the curve of FIG. 23, that are generally different from the two points used to calculate uFMD. These are $A_d(P_D-P_M)$, and $A_d(P_S-P_M)$ for the baseline curve and $A_d(P_S-P_M)$, and $A_d(P_S-P_M)$ for the curve for the dilated state. FIG. 23 illustrates these four points using the symbols Δ and ▽ depending on whether the measurements are obtained at diastole or systole. The points obtained at diastole and systole are respectively indicated using the symbols Δ and ▽. The cuff pressure at which these measurements are obtained is 64 mmHg in this case. The transmural pressures are, respectively, 77−64=13 mmHg and 122−64=58 mmHg.

To relate uFMD and cFMD, consider, for example, the empirical 3-parameter arctangent artery model employed in [1]:

$$A(P_{tm}) = a\left[\frac{1}{2} + \frac{1}{\pi}\text{atan}\left(\frac{P_{tm} - b}{c}\right)\right] \quad (2)$$

As above, let $A_b$ and $A_d$ represent the baseline and dilated arterial lumen cross sectional areas, respectively. uFMD is usually determined at systole, where the transmural pressure is equal to the systolic pressure, $P_{tm}=P_S$. uFMD % is expressed in terms of (2) as:

$$uFMD\% = (uFMD - 1) \times 100 = \left[\sqrt{\frac{A_d(P_S)}{A_b(P_S)}} - 1\right] \times 100 \quad (3)$$

In a cFMD examination, $P_{tm}$ is dependent on the systolic and diastolic blood pressures of the subject ($P_S$ and $P_D$, respectively), as well as the pressure in the measurement cuff, $P_M$:

TABLE 6

Parameters of arctangent model determined by fitting to data shown in FIG. 23.

| Parameter | Baseline | Dilated | Ratio |
|---|---|---|---|
| a | 17.59 | 24.92 | 1.57 |
| b | −1.34 | 1.66 | |
| c | 13.15 | 20.7 | |

$$cFMD\% = \quad (4)$$
$$(cFMD - 1) \times 100 = \left[\frac{A_d(P_S - P_M) - A_d(P_D - P_M)}{A_b(P_S - P_M) - A_b(P_D - P_M)} - 1\right] \times 100$$

Applying the arctangent subtraction formula to (2), we have:

$$A(P_1) - A(P_2) = \frac{a}{\pi}\text{atan}\left[\frac{\frac{1}{c}(P_1 - P_2)}{1 + \frac{1}{c}(P_1 - b)(P_2 - b)}\right],$$

which gives:

$$cFMD = \frac{a_d}{a_b} \times \frac{\text{atan}\left[\frac{\frac{1}{c_d}(P_S - P_D)}{1 + c_d^{-2}(P_S - P_M - b_d)(P_D - P_M - b_d)}\right]}{\text{atan}\left[\frac{\frac{1}{c_b}(P_S - P_D)}{1 + c_b^{-2}(P_S - P_M - b_b)(P_D - P_M - b_b)}\right]}.$$

Dimensional analysis of (2) indicates that a is in units of area, which b and c are in units of pressure. Equation (6) may thus be interpreted as the product of an area ratio (approximately proportional to the square of uFMD) and a transmural pressure dependent "gain factor".

It is instructive to examine the fitted values of a, b and c, which appear in Table 6. The value of $\sqrt{a_d/a_b}$ is 1.25. Thi is similar to the ≈20% typical dilation due to nitroglycerin observed at $P_t=P_S$.

When $P_{tm}=b$, which is a very small pressure (i.e., the artery is almost completely unloaded), $A=a/2$. In this case, $a_d/a_b$ is equal to $uFMD^2$ at large unlaoding pressure.

For the conventional case where uFMD is measured at systole with a fully loaded artery, consider an artery with $P_s=120$. At baseline:

$$A_b = a_b(\text{atan}((120+1.34)/13.15/\pi+\tfrac{1}{2}))=0.97 a_b.$$

After dilation we have:

$$A_d = a_d(\text{atan}((120+1.66)/20.7/\pi+\tfrac{1}{2}))=0.94 a_d.$$

So, $A_d/A/b=0.94/0.97 \times a_d/a_b=0.98\, a_d/a_b$ which is very close to (conventional, fully loaded) $uFMD^2$. It is therefore possible to convert a cFMD measuremnt to uFMD by calculating the 'gain factor' based on $P_M$, $P_S$, $P_D$ and this relationship between $A_d/A_b$ and $a_d/a_b$.

The above constitutes an apparently original factorization of a cFMD metric into a product of an area parameter ratio (pressure-independent) and a factor that is dependent on both blood pressure and measurement pressure.

Generalizations

The above methods were described above with respect to measurement of endothelial function. However, by changing the stimulus to nitroglycerin (for example), it is possible to assess basic smooth muscle function. Similarly, use of other stimuli (e.g., albuterol, acetylcholine, adrenergic agents, prostacyclins and endothelins) allows examination of different pathways involved in arterial dilation and constriction. The arctangent model is only one of many possible models that describe the pressure-area relationship of the vessel.

Supporting Data and Arguments.

Figure 24:
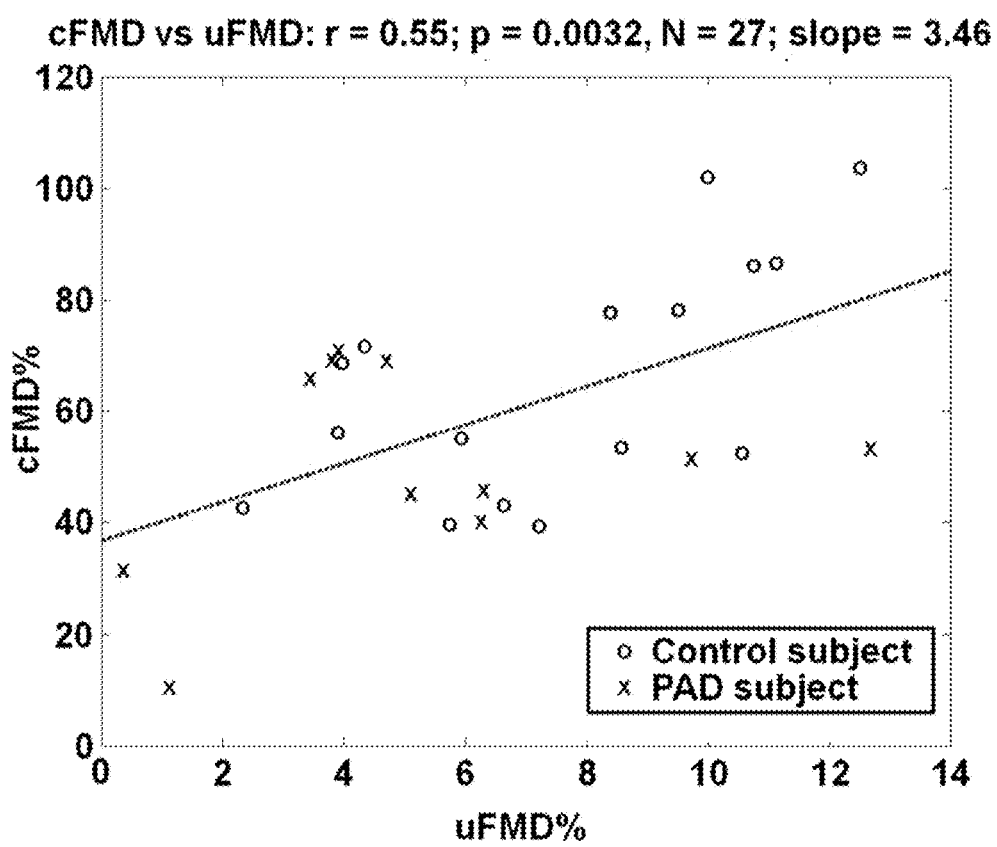
FIG. 24 shows a scatter plot of measurements of cFMD % vs. uFMD % for N=27 total subjects. We observe a correlation coefficient of r=0.55, which is statistically significant with p=0.003.

FIG. 24 is a scatter plot that shows cFMD vs uFMD measurements obtained for N=27 subjects. The characteristics of the subjects who participated in this study are listed in Table 7. These subjects had cardiovascular risk factor profiles that were less favorable than would be expected of the general population. This cohort is well-suited to demonstrate the deficiencies of uFMD in cases where arterial stiffness may confound results.

TABLE 7

Subject characteristics for cFMD/uFMD correlation study.
Mean values are shown ± their standard deviations.

|  | All | Systolic hypertensives excluded |
| --- | --- | --- |
| Number of subjects | 27 | 16 |
| # female | 8 | 6 |
| Age (years) | 64.1 ± 10.0 | 63 ± 10.1 |
| Mass (kg) | 86.0 ± 18.0 | 81.8 ± 17.9 |
| BMI (kg/m$^2$) | 29.0 ± 4.6 | 28.4 ± 4.8 |
| # diabetic | 7 | 4 |
| # tobacco ever | 17 | 9 |
| # tobacco current | 6 | 3 |
| Systolic BP (mmHg) | 144.8 ± 23.1 | 130.6 ± 7.5 |
| Diastolic BP (mmHg) | 87.3 ± 9.8 | 82.2 ± 4.9 |

Figure 25:
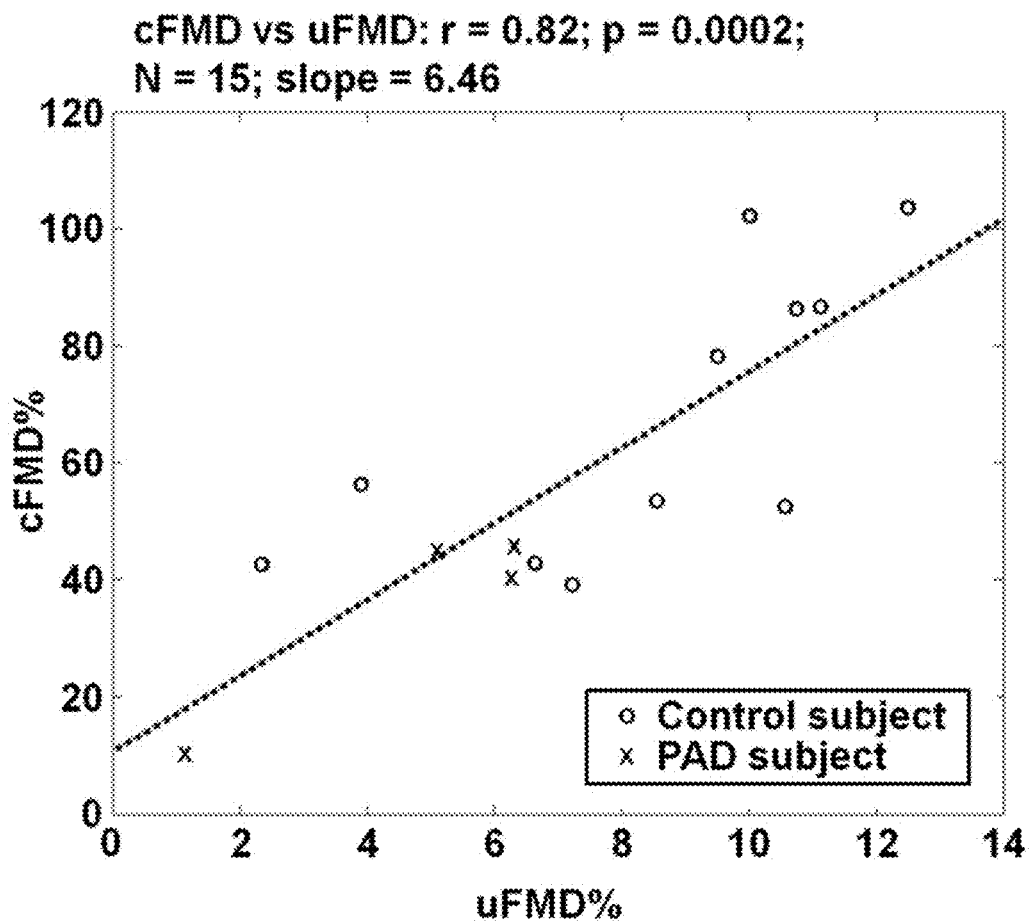
FIG. 25 shows a scatter plot of measurements of cFMD % vs. uFMD % for N=15 total subjects. We observe a correlation coefficient of r=0.82, which is statistically significant with p=0.0002. These subjects are the subset of those in FIG. 24 that exhibited systolic blood pressures of less than or equal to 140 mmHg.

When systolic hypertensive subjects (those having systolic blood pressure greater than 140 mmHg) are removed from the dataset, we find an increased correlation, as shown in FIG. 25. The rationale behind performing this particular analysis is based on the correlation between arterial stiffness and endothelial dysfunction observed in (Wallace et al. (2007) *Hypertension*, 50(1): 228-233), and is discussed further below.

Discussion.

We regard the correlation of r=0.55 observed in the data for all subjects depicted in FIG. 24 as moderate to strong, in view of the fact that our study population has substantially poorer uFMD than would be expected of a general population. This correlation is substantially higher than observed for EndoPAT, suggesting that the measurement has a different physiological basis.

Figure 26:
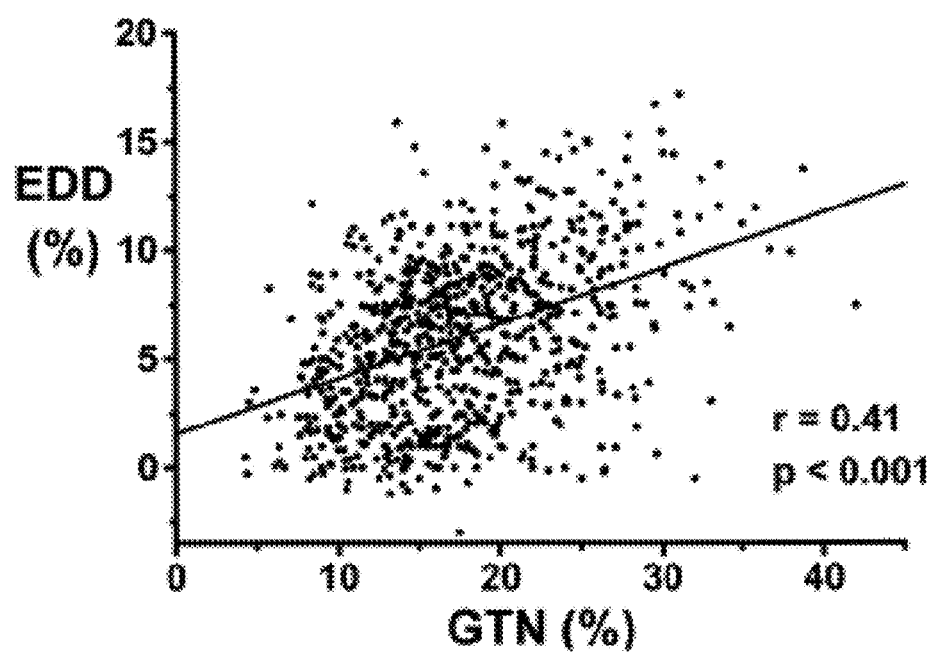
FIG. 26 Adams et al. observed a marked correlation (r=0.41) between endothelium-dependent arterial dilation (EDD) and endothelium-independent dilation (EID) in 800 subjects. When those subjects at higher risk of atherosclerosis were removed (diabetics as well as those with a history of tobacco smoking), the correlation coefficient fell to 0.24. Our results are consistent with these findings, although we do not think the attribution to smooth muscle dysfunction is correct. Rather, we think that the method used to measure EDD is confounded by arterial stiffness differences between subjects that contribute towards the correlation shown in this plot.

Subjects with isolated systolic hypertension have been found to exhibit both high aortic pulse wave velocity (arterial stiffness) and impaired FMD (Id.). We thus performed a sub-group analysis excluding subjects with systolic pressures above 140 mmHg, and found that the correlation between cFMD and uFMD increases to 0.82 (p<0.0002), as shown in FIG. 25. It is possible that mechanical unloading of stiff arteries allows more flow-mediated dilation to occur, since such arteries may not be as severely restricted by their collagen framework when the wall is under less stress. Models fit to in vivo measurements indicate that collagen fibers that act in parallel with the smooth muscle are increasingly recruited as transmural pressure rises (Bank et al. (1996) Circulation, 94(12): 3263-3270). If this is the case, uFMD may be systematically underestimating FMD in these subjects. This contention is further supported by reported correlations between endothelium-dependent and endothelium-independent dilations (EDD and EID) (Adams et al. (1998) *J. Am. Coll. Cardiol.*, 32: 123-127). In this large study of 800 subjects, Adams et al. found a correlation of 0.41 between EDD and EID. When those subjects at higher risk of atherosclerosis were removed (diabetics as well as those with a history of tobacco smoking), the correlation coefficient fell to 0.24. It is quite possible that the impaired dilation attributed to "smooth muscle dysfunction" (Id.) is in fact due to an impaired ability of the vessel to dilate even when the smooth muscle is relaxed. FIG. 26 shows the EDD-EID correlation observed in Adams et al. (1998) *J. Am. Coll. Cardiol.*, 32: 123-127.

These results support the use of cFMD rather than uFMD for endothelial function assessment, and the desirability of being able to mutually calibrate the two measurements.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of assessing cardiovascular function in a mammal, said method comprising:

a) applying external pressure $P_m$ to an artery for a period of time $T_m$, and determining, over the course of one or more cardiac cycles in said period Tm, changes in pressure in said artery resulting from cardiac activity of said mammal, or an artificially induced arterial pulse, to provide values for a baseline parameter related to endothelial function in said mammal, where said baseline parameter is provided for at least three different external pressures ($P_m$) by varying the external pressure $P_m$ during period of time $T_m$, and/or by measuring said baseline parameter over a plurality of time periods Tm having different external pressures ($P_m$), to provide a plurality of baseline values for said parameter related to cardiovascular function as a function of said external pressure ($P_m$);

b) applying a stimulus to said mammal; and c) applying external pressure $P_m$ to an said artery for a period of time $T_m$, and determining over the course of one or more cardiac cycles in said period $T_m$, changes in pressure in said artery resulting from cardiac activity of said mammal, or an artificially induced arterial pulse, to provide values for a stimulus-effected parameter related to endothelial function in said mammal, where said stimulus-effected parameter is provided for at least three different external pressures ($P_m$) by varying the external pressure $P_m$ during period of time $T_m$, and/or by determining said parameter over a plurality of time periods Tm having different external pressures ($P_m$), to provide a plurality of stimulus- effected values for said parameter related to cardiovascular function as a function of applied pressure ($P_m$);

d) determining the area, or a measure proportional to the area, of the arterial lumen calculated from the baseline measured pressures as a function of transmural pressure $P_{tm}$, where transmural pressure is determined as the difference between the baseline measured pressures and the external pressure $P_m$ and fitting these data with a first non-linear model to provide a first function describing baseline arterial lumen area as function of transmural pressure;

e) determining the area, or a measure proportional to the area, of the arterial lumen calculated from the stimulus-effected measured pressures as a function of transmural pressure $P_{tm}$, where transmural pressure is determined as the difference between the measured stimulus-effected pressures and the external pressure $P_m$ and fitting these data with a second non-linear model to provide a second function describing stimulus-effected arterial lumen area as function of transmural pressure;

f) using said first function to calculate baseline arterial lumen area ($A_b$) or a measure proportional to the area $A_b$ at a transmural pressure substantially equal to the systolic blood pressure (SBP);

g) using said second function to calculate stimulus-effected arterial lumen area ($A_r$) or a measure proportional to the area $A_r$ at a transmural pressure substantially equal to the systolic blood pressure; and h) determining the equivalent ultrasound-based flow mediated dilation (uFMD) measure where uFMD is proportional to the square root of the ratio $A_r/A_b$, and where said baseline values are determined from measurements made when said mammal is not substantially effected by said stimulus and uFMD provides a measure of cardiovascular function in said mammal.

2. The method of claim 1, comprising outputting said uFMD measure to a display, printer, or computer readable medium.

3. The method of claim 1, wherein the equivalent ultrasound-based FMD is given as $$uFMD\ \% = [\sqrt{(A_r/A_b)} - 1] \times 100.$$

4. The method of claim 1, wherein said first non-linear model and said second non-linear model are three parameter models.

5. The method of claim 1, wherein baseline values and stimulus effected values are determined for the same limb or region.

6. The method of claim 1, wherein baseline values are determined for a limb or region contralateral to a limb or region used for determining the stimulus effected values.

7. The method of claim 6, wherein said contralateral limb or region is used for monitoring blood pressure during measurement.

8. The method of claim 7, wherein monitored blood pressure is used to adjust the measurement pressure if blood pressure changes during the measurement.

9. The method of claim 1, wherein
said applying external pressure $P_m$ to said artery for a period of time $T_m$, comprises applying a substantially constant external pressure $P_m$ for a period of time $T_m$.

10. The method of claim 1, wherein said method comprises:
providing said baseline parameter for at least three different external pressures ($P_m$) by measuring said baseline parameter over a plurality of time periods $T_m$ having different external pressures ($P_m$) to provide at least three baseline values for said parameter related to cardiovascular function as a function of said external pressure ($P_m$); and
providing said values for a stimulus-effected parameter for at least three different external pressures ($P_m$) by measuring said stimulus-effected parameter over a plurality of time periods $T_m$ having different external pressures ($P_m$) to provide at least three stimulus-effected values for said parameter related to cardiovascular function as a function of applied pressure ($P_m$); or
said method comprises:
providing said baseline parameter for at least three different external pressures ($P_m$) by continuously varying the external pressure $P_m$ during period of time $T_m$ to provide at least three baseline values for said parameter related to cardiovascular function as a function of said external pressure ($P_m$); and
providing said values for a stimulus-effected parameter for at least three different external pressures ($P_m$) by continuously varying the external pressure $P_m$ during period of time $T_m$, to provide at least three stimulus-effected values for said parameter related to cardiovascular function as a function of applied pressure ($P_m$).

11. The method of claim 1, wherein:
said external pressure is less than the mean arterial pressure; or
said external pressure is less than the mean diastolic pressure.

12. The method of claim 1, wherein:
said baseline parameter and/or said stimulus-effected parameter is provided for at least three different external pressures ($P_m$) by varying the external pressure $P_m$ during period of time $T_m$; or
said baseline parameter and/or said stimulus-effected parameter is provided for at least three different external pressure points ($P_m$) by determining said baseline parameter over a plurality of time periods $T_m$ having different external pressure points ($P_m$).

13. The method of claim 1, wherein during said time interval(s) said external pressure is maintained substantially constant and held at different levels in different time intervals.

14. The method of claim 1, wherein said external pressure is adjusted to different levels during a single time period ($T_m$).

15. The method of claim 1, wherein:
said providing stimulus-effected values comprises providing values for changes in pressure from an artificially induced arterial pulse; or said providing stimulus-effected values comprises providing values for change in pressure resulting from cardiac activity of said mammal.

16. the method of claim 1, wherein said substantially external pressure is below the average diastolic pressure measured for said subject or below an expected diastolic pressure for said subject.

17. The method of claim 1, wherein the providing stimulus-effected values is performed at least about 30 seconds after stimulus up to about 5 minutes after said stimulus.

18. The method of claim 1, wherein said providing over the course of one or more cardiac cycles, changes in pressure in said cuff resulting from cardiac activity of said mammal comprises determining the pressure in said cuff as a function of time.

19. The method of claim 18, wherein:
said providing comprises integrating the value of a pressure change over time (calculating the area under a pressure/time curve) for one or for a plurality of cardiac cycles to determine an integrated pressure value; and/or
said providing comprises determining the maximum, or a certain percentile rank of the derivative of the pressure versus time wave form on the rising edge of a pressure pulse for one or for a plurality of cardiac cycles to determine a compliance value.

20. The method of claim 19, wherein said integrated pressure value and/or said compliance value is determined for a single cardiac cycle.

21. The method of claim 20, wherein
said single cardiac cycle is a cardiac cycle selected for the maximum change in said value in a plurality of cardiac cycles; or
said single cardiac cycle is a cardiac cycle selected for the maximum change in said value between a baseline measurement and a stimulus-effected measurement.

22. The method of claim 18, wherein said providing, over the course of one or more cardiac cycles, changes in pressure in said cuff resulting from cardiac activity of said mammal comprises determining the pressure in said cuff as a function of time to provide a cardiac pulse waveform.

23. The method of claim 22, wherein said providing, over the course of one or more cardiac cycles, changes in pressure in said cuff resulting from cardiac activity of said mammal comprises determining the pressure in said cuff as a function of time to provide a cardiac pulse waveform while the cuff inflates and/or while said cuff deflates.

24. The method of claim 23, wherein
the cardiac pulse waveforms are compared between baseline and post-stimulus conditions by direct comparison of pulse characteristics at corresponding pressure levels; or
the cardiac pulse waveforms are compared between baseline and post-stimulus conditions by first fitting models to the set of baseline cardiac pulse waver forms and to the set of post-stimulus cardiac pulse waveforms and comparing parameters generated by the two models.

25. The method of claim 23, wherein said external pressure is a pressure in excess of the peak of the cardiac pulse waveform.

26. The method according of claim 23, wherein: the systolic blood pressure and mean arterial pressure are measured and the diastolic blood pressure (DBP) is calculated using an oscillometric analysis; or the systolic blood pressure and mean arterial pressure are measured and the DBP is determined by analyzing Korotkoff sounds obtained using an audio sensor or ultrasound probe.

27. The method of claim 23, wherein measurements to calculate cuff-based flow-mediated vasodilation (cFMD) and/or mean arterial pressure, and/or diastolic blood pressure are obtained during inflation or deflation of a sphygmomanometer cuff.

28. The method according of claim 23, wherein: systolic blood pressure and/or diastolic blood pressure is determined and for cuff-based flow-mediated vasodilation (cFMD) determination, comparison of pulse waveform characteristics between baseline and post-stimulus intervals at corresponding pressures is a comparison made where the corresponding pressures are transmural pressures calculated using the determined systolic and/or diastolic blood pressure values; or comparison of pulse waveform characteristics between baseline and post-stimulus intervals at corresponding pressures is a comparison made based on the transmural pressure determined by the models.

29. The method of claim 1, wherein applying the stimulus comprises restricting flow of blood to the limb by occlusion of a blood vessel, or administering a drug to said mammal or applying low intensity ultrasound and/or acoustic/mechanical tissue vibration to said mammal.

30. The method of claim 1, wherein said applying external pressure $P_m$ to said artery for a period of time $T_m$ comprises applying a continuously varying external pressure $P_m$ for a period of time $T_m$.

* * * * *